(12) United States Patent
Andrieux et al.

(10) Patent No.: US 9,649,458 B2
(45) Date of Patent: *May 16, 2017

(54) BREATHING ASSISTANCE SYSTEM WITH MULTIPLE PRESSURE SENSORS

(71) Applicant: Covidien LP, Mansfield, MA (US)

(72) Inventors: Claude Andrieux, Bordes (FR); Cedric Jourdain, Lons (FR)

(73) Assignee: COVIDIEN LP, Mansfield, MA (US)

(*) Notice: Subject to any disclaimer, the term of this patent is extended or adjusted under 35 U.S.C. 154(b) by 808 days.

This patent is subject to a terminal disclaimer.

(21) Appl. No.: 13/659,190

(22) Filed: Oct. 24, 2012

(65) Prior Publication Data
US 2013/0042869 A1 Feb. 21, 2013

Related U.S. Application Data

(63) Continuation of application No. 12/241,243, filed on Sep. 30, 2008, now Pat. No. 8,302,602.

(51) Int. Cl.
*A61M 11/00* (2006.01)
*A61M 16/00* (2006.01)
*A61M 16/10* (2006.01)

(52) U.S. Cl.
CPC .... *A61M 16/0051* (2013.01); *A61M 16/0069* (2014.02); *A61M 16/1015* (2014.02);
(Continued)

(58) Field of Classification Search
CPC ........ A61M 2230/005; A61M 16/0051; A61M 2016/0027; A61M 2230/435; A61M 2016/0039; A61M 2016/0042; A61M 2016/1025; A61M 2202/0208; A61M 2205/16; A61M 2205/17;
(Continued)

(56) References Cited

U.S. PATENT DOCUMENTS 3,120,843 A 2/1964 Hyman .................... 128/202.22
3,267,935 A 8/1966 Andreasen et al. ............ 128/29
(Continued)

FOREIGN PATENT DOCUMENTS

DE 3306607 A1 2/1983 ............ A61M 16/00
DE 3732475 4/1989 ............ A61M 16/00
(Continued)

OTHER PUBLICATIONS

Clergue et al., Le Respirateur Servo Ventilator 900C, Departement d'anesthesie-reanimation (Pr P. Viars) Groupe Hospitalier Pitie, Salpetriere, Paris, pp. 417-421, 1984.
(Continued)

*Primary Examiner* — Steven Douglas

(57) ABSTRACT

A method for managing pressure in a breathing assistance system configured to provide breathing assistance to a patient via a patient connection system is provided. The method may include receiving one or more first pressure sensor signals from a first pressure sensor, and analyzing the one or more first pressure sensor signals. Based at least on the analysis of the one or more first pressure sensor signals, either the first pressure sensor or the second pressure sensor may be selected for use in controlling the breathing assistance provided to the patient, and the breathing assistance provided to the patient may be controlled based at least on signals from the selected pressure sensor.

25 Claims, 13 Drawing Sheets

(52) U.S. Cl.
CPC ............ *A61M 2016/0027* (2013.01); *A61M 2016/0039* (2013.01); *A61M 2016/0042* (2013.01); *A61M 2016/1025* (2013.01); *A61M 2202/0208* (2013.01); *A61M 2205/16* (2013.01); *A61M 2205/17* (2013.01); *A61M 2205/3368* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/505* (2013.01); *A61M 2205/8206* (2013.01); *A61M 2205/8212* (2013.01)

(58) Field of Classification Search
CPC .. A61M 2205/3368; A61M 2205/3553; A61M 2205/3561; A61M 2205/3569; A61M 2205/3584; A61M 2205/3592; A61M 2205/505; A61M 2205/8206; A61M 2205/8212; A61M 16/0069; A61M 16/101
USPC ............ 128/204.18, 204.21–204.23, 204.26, 128/204.29
See application file for complete search history.

(56) References Cited

U.S. PATENT DOCUMENTS

| | | | |
|---|---|---|---|
| 3,333,584 A | 8/1967 | Andreasen et al. | 128/202.22 |
| 3,444,857 A | 5/1969 | Godel | |
| 3,481,333 A | 12/1969 | Garrison | |
| 3,485,243 A | 12/1969 | Bird et al. | |
| 3,584,621 A | 6/1971 | Bird et al. | |
| 3,586,021 A | 6/1971 | McGuinness | |
| 3,595,228 A | 7/1971 | Simon et al. | 128/202.22 |
| 3,633,576 A | 1/1972 | Gorsuch | |
| 3,662,751 A | 5/1972 | Barkalow et al. | |
| 3,664,370 A | 5/1972 | Warnow | |
| 3,669,108 A | 6/1972 | Sundblom et al. | |
| 3,675,640 A | 7/1972 | Gatts | 128/2.05 R |
| 3,688,794 A | 9/1972 | Bird et al. | |
| 3,695,263 A | 10/1972 | Kipling | |
| 3,741,208 A | 6/1973 | Jonsson et al. | |
| 3,753,436 A | 8/1973 | Bird et al. | |
| 3,756,229 A | 9/1973 | Ollivier | |
| 3,768,468 A | 10/1973 | Cox | |
| 3,789,837 A | 2/1974 | Philips et al. | |
| 3,805,780 A | 4/1974 | Cramer et al. | |
| 3,811,400 A | 5/1974 | Smilg | 116/70 |
| 3,827,433 A | 8/1974 | Shannon | |
| 3,831,595 A | 8/1974 | Valenta et al. | 128/202.22 |
| 3,834,382 A | 9/1974 | Lederman et al. | |
| 3,848,591 A | 11/1974 | Smythe et al. | 128/204.23 |
| 3,867,934 A | 2/1975 | Ollivier | 128/202.22 |
| 3,869,771 A | 3/1975 | Bollinger | |
| 3,877,467 A | 4/1975 | Plicchi | 128/202.22 |
| 3,889,669 A | 6/1975 | Weigl | |
| 3,889,670 A | 6/1975 | Loveland et al. | |
| 3,896,800 A | 7/1975 | Cibulka | |
| 3,903,881 A | 9/1975 | Weigl | |
| 3,905,362 A | 9/1975 | Eyrick et al. | |
| 3,908,987 A | 9/1975 | Boehringer | |
| 3,910,261 A | 10/1975 | Ragsdale et al. | |
| 3,916,888 A | 11/1975 | Buck et al. | 128/204.21 |
| 3,941,124 A | 3/1976 | Rodewald et al. | |
| 3,961,627 A | 6/1976 | Ernst et al. | |
| 3,976,052 A | 8/1976 | Junginger et al. | |
| 3,976,065 A | 8/1976 | Durkan | |
| 3,981,301 A | 9/1976 | Warnow et al. | |
| 3,985,131 A | 10/1976 | Buck et al. | 128/145.8 |
| 3,991,304 A | 11/1976 | Hillsman | 235/151.34 |
| 4,003,377 A | 1/1977 | Dahl | |
| 4,020,834 A | 5/1977 | Bird | |
| 4,029,120 A | 6/1977 | Christianson | |
| 4,036,221 A | 7/1977 | Hillsman et al. | 128/145.6 |
| 4,044,763 A | 8/1977 | Bird | |
| 4,050,458 A | 9/1977 | Friend | |
| 4,056,098 A | 11/1977 | Michel et al. | |
| 4,057,059 A | 11/1977 | Reid, Jr. et al. | |
| 4,060,078 A | 11/1977 | Bird | |
| 4,077,404 A | 3/1978 | Elam | 128/145.8 |
| 4,082,093 A | 4/1978 | Fry et al. | |
| 4,096,858 A | 6/1978 | Eyrick et al. | 128/205.16 |
| 4,121,578 A | 10/1978 | Torzala | |
| 4,155,357 A | 5/1979 | Dahl | |
| 4,164,219 A | 8/1979 | Bird | |
| 4,176,617 A | 12/1979 | Pilipski | 116/70 |
| 4,197,843 A | 4/1980 | Bird | |
| 4,197,856 A | 4/1980 | Northrop | |
| 4,206,754 A | 6/1980 | Cox et al. | |
| 4,211,221 A | 7/1980 | Schwanbom et al. | |
| 4,211,239 A | 7/1980 | Raemer et al. | |
| 4,227,523 A | 10/1980 | Warnow et al. | |
| 4,232,666 A | 11/1980 | Savelli et al. | |
| 4,239,039 A | 12/1980 | Thompson | 128/205.24 |
| 4,241,756 A | 12/1980 | Bennett et al. | |
| 4,245,633 A | 1/1981 | Erceg | |
| 4,249,528 A | 2/1981 | Mathes | 128/205.13 |
| 4,265,237 A | 5/1981 | Schwanbom et al. | |
| 4,267,827 A | 5/1981 | Racher et al. | |
| 4,275,722 A | 6/1981 | Sorensen | |
| 4,281,651 A | 8/1981 | Cox | |
| 4,285,340 A | 8/1981 | Gezari et al. | |
| 4,286,589 A | 9/1981 | Thompson | 128/202.22 |
| 4,287,886 A | 9/1981 | Thompson | 128/202.22 |
| 4,302,640 A | 11/1981 | Vicenzi et al. | 200/81 R |
| 4,305,388 A | 12/1981 | Brisson | |
| 4,318,399 A | 3/1982 | Berndtsson | 128/204.23 |
| 4,320,754 A | 3/1982 | Watson et al. | |
| 4,323,064 A | 4/1982 | Hoenig et al. | |
| 4,336,590 A | 6/1982 | Jacq et al. | 364/418 |
| 4,340,044 A | 7/1982 | Levy et al. | |
| 4,351,328 A | 9/1982 | Bodai | |
| 4,351,329 A | 9/1982 | Ellestad et al. | |
| 4,351,344 A | 9/1982 | Stenzler | |
| 4,365,636 A | 12/1982 | Barker | 600/529 |
| 4,401,115 A | 8/1983 | Monnier | |
| 4,417,573 A | 11/1983 | De Vries | |
| 4,421,113 A | 12/1983 | Gedeon et al. | 128/204.23 |
| 4,436,090 A | 3/1984 | Darling | |
| 4,440,177 A | 4/1984 | Anderson et al. | 600/532 |
| 4,444,201 A | 4/1984 | Itoh | 128/716 |
| 4,448,192 A | 5/1984 | Stawitcke et al. | 128/204.26 |
| 4,457,304 A | 7/1984 | Molnar et al. | |
| 4,459,982 A | 7/1984 | Fry | |
| 4,459,983 A | 7/1984 | Beyreuther et al. | |
| 4,462,397 A | 7/1984 | Suzuki | |
| 4,466,433 A | 8/1984 | Robbins | 128/202.22 |
| 4,502,481 A | 3/1985 | Christian | |
| 4,527,557 A | 7/1985 | DeVries et al. | |
| 4,539,984 A | 9/1985 | Kiszel et al. | |
| 4,550,726 A | 11/1985 | McEwen | 128/202.22 |
| 4,554,916 A | 11/1985 | Watt | |
| 4,558,710 A | 12/1985 | Eichler | |
| 4,566,450 A | 1/1986 | Brossman, Jr. | |
| 4,596,246 A | 6/1986 | Lyall | |
| 4,598,706 A | 7/1986 | Darowski et al. | |
| 4,602,644 A | 7/1986 | DiBenedetto et al. | 128/725 |
| 4,608,976 A | 9/1986 | Suchy | |
| 4,611,591 A | 9/1986 | Inui et al. | |
| 4,612,928 A | 9/1986 | Tiep et al. | |
| 4,622,976 A | 11/1986 | Timpe et al. | |
| 4,635,631 A | 1/1987 | Izumi | 128/204.23 |
| 4,637,385 A | 1/1987 | Rusz | 128/204.21 |
| 4,637,386 A | 1/1987 | Baum | 128/204.21 |
| 4,640,277 A | 2/1987 | Meyer et al. | |
| 4,648,407 A | 3/1987 | Sackner | |
| 4,651,731 A | 3/1987 | Vicenzi et al. | |
| 4,655,213 A | 4/1987 | Rapoport et al. | 128/205.25 |
| 4,674,492 A | 6/1987 | Niemeyer | 128/202.22 |
| 4,686,974 A | 8/1987 | Sato et al. | 128/204.23 |
| 4,686,975 A | 8/1987 | Naimon et al. | 128/204.23 |
| 4,699,137 A | 10/1987 | Schroeder | |
| RE32,553 E | 12/1987 | Bennett et al. | |
| 4,712,580 A | 12/1987 | Gilman et al. | |

(56) References Cited

U.S. PATENT DOCUMENTS

| | | | |
|---|---|---|---|
| 4,723,543 A | 2/1988 | Beran | 128/207.14 |
| 4,727,871 A | 3/1988 | Smargiassi et al. | |
| 4,747,403 A | 5/1988 | Gluck et al. | |
| 4,752,089 A | 6/1988 | Carter | |
| 4,757,824 A | 7/1988 | Chaumet | |
| 4,765,326 A | 8/1988 | Pieper | 128/202.22 |
| 4,766,894 A | 8/1988 | Legrand et al. | |
| 4,782,832 A | 11/1988 | Trimble et al. | 128/207.18 |
| 4,796,618 A | 1/1989 | Garraffa | |
| 4,803,997 A | 2/1989 | Bowman | 128/723 |
| 4,811,755 A | 3/1989 | Bourdon et al. | 137/486 |
| 4,813,409 A | 3/1989 | Ismach | |
| 4,821,709 A | 4/1989 | Jensen | |
| 4,825,802 A | 5/1989 | Le Bec | 116/70 |
| 4,838,257 A | 6/1989 | Hatch | 128/204.18 |
| 4,870,393 A | 9/1989 | Snuttjer et al. | 340/611 |
| 4,877,023 A | 10/1989 | Zalkin | |
| 4,883,051 A | 11/1989 | Westenskow et al. | 128/204.21 |
| 4,889,116 A | 12/1989 | Taube | |
| 4,899,740 A | 2/1990 | Napolitano | 128/202.22 |
| 4,921,642 A | 5/1990 | LaTorraca | |
| 4,924,862 A | 5/1990 | Levinson | |
| 4,939,647 A | 7/1990 | Clough et al. | |
| 4,941,469 A | 7/1990 | Adahan | 128/205.18 |
| 4,944,310 A | 7/1990 | Sullivan | 128/848 |
| 4,954,799 A | 9/1990 | Kumar | |
| 4,957,107 A | 9/1990 | Sipin | |
| 4,967,744 A | 11/1990 | Chua | 128/204.18 |
| 4,971,049 A | 11/1990 | Rotariu | 128/204.21 |
| 4,971,052 A | 11/1990 | Edwards | |
| 4,981,295 A | 1/1991 | Belman et al. | |
| 4,982,735 A | 1/1991 | Yagata et al. | |
| 4,986,268 A | 1/1991 | Tehrani | |
| 4,990,894 A | 2/1991 | Loescher et al. | 340/573 |
| 4,991,576 A | 2/1991 | Henkin et al. | |
| 4,993,269 A | 2/1991 | Guillaume et al. | |
| 5,000,173 A | 3/1991 | Zalkin et al. | |
| 5,002,050 A | 3/1991 | McGinnis | |
| 5,007,420 A | 4/1991 | Bird | |
| 5,016,626 A | 5/1991 | Jones | |
| 5,020,532 A | 6/1991 | Mahoney et al. | |
| 5,035,239 A | 7/1991 | Edwards | 128/205.23 |
| 5,042,470 A | 8/1991 | Kanesaka | 128/202.22 |
| 5,057,822 A | 10/1991 | Hoffman | |
| 5,063,925 A | 11/1991 | Frank et al. | |
| 5,065,746 A | 11/1991 | Steen | |
| 5,065,756 A | 11/1991 | Rapoport | 128/204.18 |
| 5,067,487 A | 11/1991 | Bauman | |
| 5,072,729 A | 12/1991 | DeVries | |
| 5,072,737 A | 12/1991 | Goulding | |
| 5,094,235 A | 3/1992 | Westenskow et al. | |
| 5,097,826 A | 3/1992 | Gray et al. | 128/204.18 |
| 5,099,837 A | 3/1992 | Russel, Sr. et al. | |
| 5,107,830 A | 4/1992 | Younes | 128/204.18 |
| 5,107,831 A | 4/1992 | Halpern et al. | 128/204.26 |
| 5,109,838 A | 5/1992 | Elam | |
| 5,117,819 A | 6/1992 | Servidio et al. | 128/204.18 |
| 5,127,400 A | 7/1992 | DeVries et al. | |
| 5,129,390 A | 7/1992 | Chopin et al. | 128/204.21 |
| 5,134,995 A | 8/1992 | Gruenke et al. | |
| 5,146,092 A | 9/1992 | Apperson et al. | |
| 5,146,918 A | 9/1992 | Kallok et al. | 607/2 |
| 5,148,802 A | 9/1992 | Sanders et al. | 128/204.18 |
| 5,150,291 A | 9/1992 | Cummings et al. | |
| 5,153,436 A | 10/1992 | Apperson et al. | |
| 5,154,167 A | 10/1992 | Hepburn | |
| 5,158,569 A | 10/1992 | Strickland et al. | |
| 5,161,525 A | 11/1992 | Kimm et al. | |
| 5,161,541 A | 11/1992 | Bowman et al. | 128/724 |
| 5,165,397 A | 11/1992 | Arp | |
| 5,165,398 A | 11/1992 | Bird | |
| 5,168,868 A | 12/1992 | Hicks | |
| 5,178,155 A | 1/1993 | Mault | |
| 5,190,048 A | 3/1993 | Wilkinson | 128/724 |
| 5,199,424 A | 4/1993 | Sullivan et al. | 128/204.18 |
| 5,203,343 A | 4/1993 | Axe et al. | 600/538 |
| 5,222,491 A | 6/1993 | Thomas | |
| 5,231,979 A | 8/1993 | Rose et al. | 128/204.14 |
| 5,237,987 A | 8/1993 | Anderson et al. | |
| 5,239,995 A | 8/1993 | Estes et al. | 128/204.23 |
| 5,246,995 A | 9/1993 | Murakami et al. | 128/204.23 |
| 5,255,675 A | 10/1993 | Kolobow | |
| 5,259,373 A | 11/1993 | Gruenke et al. | |
| 5,269,293 A | 12/1993 | Loser et al. | |
| 5,269,296 A | 12/1993 | Landis | 128/207.18 |
| 5,271,389 A | 12/1993 | Isaza et al. | |
| 5,275,159 A | 1/1994 | Griebel | 128/633 |
| 5,277,175 A | 1/1994 | Riggs et al. | |
| 5,279,549 A | 1/1994 | Ranford | |
| 5,299,568 A | 4/1994 | Forare et al. | |
| 5,301,667 A | 4/1994 | McGrail et al. | |
| 5,301,921 A | 4/1994 | Kumar | |
| 5,303,698 A | 4/1994 | Tobia et al. | |
| 5,303,699 A | 4/1994 | Bonassa et al. | |
| 5,309,901 A | 5/1994 | Beaussant | |
| 5,313,937 A | 5/1994 | Zdrojkowski | 128/202.22 |
| 5,315,989 A | 5/1994 | Tobia | |
| 5,316,009 A | 5/1994 | Yamada | |
| 5,318,487 A | 6/1994 | Golen et al. | |
| 5,319,540 A | 6/1994 | Isaza et al. | |
| 5,320,092 A | 6/1994 | Ryder | 128/202.22 |
| 5,323,772 A | 6/1994 | Linden et al. | |
| 5,325,861 A | 7/1994 | Goulding | |
| 5,331,995 A | 7/1994 | Westfall et al. | |
| 5,333,606 A | 8/1994 | Schneider et al. | |
| 5,335,651 A | 8/1994 | Foster et al. | |
| 5,335,654 A | 8/1994 | Rapoport | |
| 5,339,807 A | 8/1994 | Carter | |
| 5,343,857 A | 9/1994 | Schneider et al. | |
| 5,343,858 A | 9/1994 | Winefordner et al. | |
| 5,351,522 A | 10/1994 | Lura | |
| 5,353,788 A | 10/1994 | Miles | 128/204.23 |
| 5,357,946 A | 10/1994 | Kee et al. | |
| 5,360,000 A | 11/1994 | Carter | |
| 5,365,922 A | 11/1994 | Raemer | |
| 5,368,019 A | 11/1994 | LaTorraca | |
| 5,368,021 A | 11/1994 | Beard et al. | |
| 5,369,277 A | 11/1994 | Knodle et al. | |
| 5,373,842 A | 12/1994 | Olsson et al. | |
| 5,383,449 A | 1/1995 | Forare et al. | |
| 5,385,142 A | 1/1995 | Brady et al. | |
| 5,388,575 A | 2/1995 | Taube | |
| 5,390,666 A | 2/1995 | Kimm et al. | |
| 5,398,677 A | 3/1995 | Smith | |
| 5,398,682 A | 3/1995 | Lynn | |
| 5,401,135 A | 3/1995 | Stoen et al. | |
| 5,402,796 A | 4/1995 | Packer et al. | |
| 5,404,871 A | 4/1995 | Goodman et al. | |
| 5,407,174 A | 4/1995 | Kumar | |
| 5,413,110 A | 5/1995 | Cummings et al. | |
| 5,413,111 A | 5/1995 | Wilkinson | 128/724 |
| 5,429,123 A | 7/1995 | Shaffer et al. | |
| 5,433,193 A | 7/1995 | Sanders et al. | |
| 5,438,980 A | 8/1995 | Phillips | |
| 5,443,075 A | 8/1995 | Holscher | |
| 5,452,714 A | 9/1995 | Anderson et al. | |
| 5,456,264 A | 10/1995 | Series et al. | 128/725 |
| 5,458,137 A | 10/1995 | Axe et al. | |
| 5,467,766 A | 11/1995 | Ansite et al. | |
| 5,479,920 A | 1/1996 | Piper et al. | |
| 5,484,270 A | 1/1996 | Adahan | |
| 5,487,383 A | 1/1996 | Levinson | |
| 5,490,499 A | 2/1996 | Heinonen et al. | 128/203.28 |
| 5,490,502 A | 2/1996 | Rapoport et al. | 128/204.23 |
| 5,494,028 A | 2/1996 | DeVries et al. | |
| 5,497,767 A | 3/1996 | Olsson et al. | |
| 5,503,140 A | 4/1996 | Winefordner et al. | |
| 5,503,146 A | 4/1996 | Froehlich et al. | 128/204.23 |
| 5,503,147 A | 4/1996 | Bertheau | |
| 5,507,282 A | 4/1996 | Younes | |
| 5,509,406 A | 4/1996 | Kock et al. | |
| 5,513,631 A | 5/1996 | McWilliams | |
| 5,517,983 A | 5/1996 | Deighan et al. | |
| 5,520,071 A | 5/1996 | Jones | |

(56) References Cited

U.S. PATENT DOCUMENTS

| | | | |
|---|---|---|---|
| 5,520,172 A | 5/1996 | Obermayer | 128/205.13 |
| 5,522,382 A | 6/1996 | Sullivan et al. | 128/204.23 |
| 5,524,615 A | 6/1996 | Power | |
| 5,531,221 A | 7/1996 | Power | |
| 5,535,738 A | 7/1996 | Estes et al. | |
| 5,535,739 A | 7/1996 | Rapoport et al. | 128/204.23 |
| 5,537,997 A | 7/1996 | Mechlenburg et al. | 128/204.23 |
| 5,540,220 A | 7/1996 | Gropper et al. | |
| 5,540,733 A | 7/1996 | Testerman et al. | 607/42 |
| 5,542,415 A | 8/1996 | Brody | |
| 5,542,416 A | 8/1996 | Chalvignac | |
| 5,544,674 A | 8/1996 | Kelly | |
| 5,546,933 A | 8/1996 | Rapoport et al. | 128/204.23 |
| 5,546,935 A | 8/1996 | Champeau | |
| 5,549,106 A | 8/1996 | Gruenke et al. | |
| 5,549,655 A | 8/1996 | Erickson | |
| 5,551,419 A | 9/1996 | Froehlich et al. | |
| RE35,339 E | 10/1996 | Rapoport | 128/204.18 |
| 5,564,416 A | 10/1996 | Jones | |
| 5,568,910 A | 10/1996 | Koehler et al. | |
| 5,575,283 A | 11/1996 | Sjoestrand | |
| 5,577,496 A | 11/1996 | Blackwood et al. | 128/201.25 |
| 5,582,163 A | 12/1996 | Bonassa | |
| 5,596,984 A | 1/1997 | O'Mahony et al. | |
| 5,603,315 A | 2/1997 | Sasso, Jr. | |
| 5,605,151 A | 2/1997 | Lynn | |
| 5,606,968 A | 3/1997 | Mang | |
| 5,615,669 A | 4/1997 | Olsson et al. | |
| 5,616,923 A | 4/1997 | Rich et al. | |
| 5,617,847 A | 4/1997 | Howe | |
| 5,623,923 A | 4/1997 | Bertheau et al. | |
| 5,626,129 A | 5/1997 | Klimm et al. | 128/202.22 |
| 5,630,411 A | 5/1997 | Holscher | |
| 5,632,269 A | 5/1997 | Zdrojkowski | |
| 5,632,270 A | 5/1997 | O'Mahony et al. | |
| 5,640,149 A | 6/1997 | Campbell | 340/626 |
| 5,645,048 A | 7/1997 | Brodsky et al. | |
| 5,645,053 A | 7/1997 | Remmers et al. | |
| 5,645,054 A | 7/1997 | Cotner | 128/204.23 |
| 5,647,345 A | 7/1997 | Saul | |
| 5,647,351 A | 7/1997 | Weismann et al. | |
| 5,651,360 A | 7/1997 | Tobia | |
| 5,657,750 A | 8/1997 | Colman et al. | |
| 5,660,171 A | 8/1997 | Kimm et al. | |
| 5,662,099 A | 9/1997 | Tobia et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,678,537 A | 10/1997 | Bathe et al. | |
| 5,683,232 A | 11/1997 | Adahan | |
| 5,692,497 A | 12/1997 | Schnitzer et al. | |
| 5,693,944 A | 12/1997 | Rich | |
| 5,694,926 A | 12/1997 | DeVries et al. | |
| 5,697,363 A | 12/1997 | Hart | |
| 5,697,364 A | 12/1997 | Chua et al. | |
| 5,701,883 A | 12/1997 | Hete et al. | |
| 5,701,889 A | 12/1997 | Danon | |
| 5,704,345 A | 1/1998 | Berthon-Jones | 128/204.23 |
| 5,706,799 A | 1/1998 | Imai et al. | |
| 5,715,812 A | 2/1998 | Deighan et al. | |
| 5,720,277 A | 2/1998 | Olsson et al. | |
| 5,720,709 A | 2/1998 | Schnall | 600/538 |
| 5,727,562 A | 3/1998 | Beck | |
| 5,730,122 A | 3/1998 | Lurie | |
| 5,732,696 A | 3/1998 | Rapoport et al. | 128/630 |
| 5,735,267 A | 4/1998 | Tobia | |
| 5,738,090 A | 4/1998 | Lachmann et al. | |
| 5,740,796 A | 4/1998 | Skog | |
| 5,743,253 A | 4/1998 | Castor et al. | 128/200.24 |
| 5,746,201 A | 5/1998 | Kidd | 128/206.24 |
| 5,746,697 A | 5/1998 | Swedlow et al. | 600/323 |
| 5,752,509 A | 5/1998 | Lachmann et al. | |
| 5,762,480 A | 6/1998 | Adahan | |
| 5,769,072 A | 6/1998 | Olsson et al. | |
| 5,771,884 A | 6/1998 | Yarnall et al. | |
| 5,789,660 A | 8/1998 | Kofoed et al. | |
| 5,791,339 A | 8/1998 | Winter | |
| 5,794,614 A | 8/1998 | Gruenke et al. | |
| 5,794,615 A | 8/1998 | Estes | |
| 5,794,986 A | 8/1998 | Gansel et al. | |
| 5,797,393 A | 8/1998 | Kohl | |
| 5,803,064 A | 9/1998 | Phelps et al. | |
| 5,803,066 A | 9/1998 | Rapoport et al. | |
| 5,813,399 A | 9/1998 | Isaza et al. | |
| 5,823,179 A | 10/1998 | Grychowski et al. | |
| 5,826,575 A | 10/1998 | Lall | |
| 5,829,441 A | 11/1998 | Kidd et al. | |
| 5,845,636 A | 12/1998 | Gruenke et al. | |
| 5,857,458 A | 1/1999 | Tham et al. | |
| 5,864,938 A | 2/1999 | Gansel et al. | |
| 5,865,168 A | 2/1999 | Isaza | |
| 5,865,173 A | 2/1999 | Froehlich | |
| 5,868,133 A | 2/1999 | DeVries et al. | |
| 5,873,361 A | 2/1999 | Hakala | 128/204.23 |
| 5,875,783 A | 3/1999 | Kullik | |
| 5,876,352 A | 3/1999 | Weismann | |
| 5,878,744 A | 3/1999 | Pfeiffer | 128/204.23 |
| 5,881,717 A | 3/1999 | Isaza | |
| 5,881,722 A | 3/1999 | DeVries et al. | |
| 5,881,723 A | 3/1999 | Wallace et al. | |
| 5,884,623 A | 3/1999 | Winter | |
| 5,891,023 A | 4/1999 | Lynn | |
| 5,901,704 A | 5/1999 | Estes et al. | 128/204.23 |
| 5,906,204 A | 5/1999 | Beran et al. | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,381 A | 6/1999 | Nord | |
| 5,915,382 A | 6/1999 | Power | |
| 5,918,597 A | 7/1999 | Jones et al. | |
| 5,921,238 A | 7/1999 | Bourdon | |
| 5,924,979 A | 7/1999 | Swedlow et al. | 600/300 |
| 5,927,274 A | 7/1999 | Servidio et al. | |
| 5,931,162 A | 8/1999 | Christian | |
| 5,934,274 A | 8/1999 | Merrick et al. | |
| 5,937,856 A | 8/1999 | Jonasson et al. | |
| 5,941,846 A | 8/1999 | Duffy et al. | |
| 5,950,621 A | 9/1999 | Klockseth et al. | 128/204.26 |
| 5,957,130 A | 9/1999 | Krahbichler et al. | |
| 5,970,975 A | 10/1999 | Estes et al. | |
| 5,975,081 A | 11/1999 | Hood et al. | |
| 5,983,891 A | 11/1999 | Fukunaga | |
| 6,000,396 A | 12/1999 | Melker et al. | |
| 6,003,513 A | 12/1999 | Readey et al. | |
| 6,010,459 A | 1/2000 | Silkoff et al. | |
| 6,017,315 A | 1/2000 | Starr et al. | |
| 6,024,089 A | 2/2000 | Wallace et al. | |
| 6,029,664 A | 2/2000 | Zdrojkowski et al. | |
| 6,029,667 A | 2/2000 | Lurie | |
| 6,032,065 A | 2/2000 | Brown | 600/383 |
| 6,041,777 A | 3/2000 | Faithfull et al. | |
| 6,041,780 A | 3/2000 | Richard et al. | |
| 6,042,550 A | 3/2000 | Haryadi et al. | |
| 6,044,841 A | 4/2000 | Verdun et al. | |
| 6,047,860 A | 4/2000 | Sanders | |
| 6,066,101 A | 5/2000 | Johnson et al. | |
| 6,067,022 A | 5/2000 | Laswick et al. | 340/626 |
| 6,067,984 A | 5/2000 | Piper | |
| 6,073,630 A | 6/2000 | Adahan | |
| 6,076,519 A | 6/2000 | Johnson | |
| 6,076,523 A | 6/2000 | Jones et al. | |
| 6,085,747 A | 7/2000 | Axe et al. | 128/204.23 |
| 6,095,139 A | 8/2000 | Psaros | |
| 6,095,140 A | 8/2000 | Poon et al. | |
| 6,099,481 A | 8/2000 | Daniels et al. | |
| 6,102,038 A | 8/2000 | DeVries | |
| 6,105,575 A | 8/2000 | Estes et al. | |
| 6,106,480 A | 8/2000 | Gama De Abreu et al. | |
| 6,116,240 A | 9/2000 | Merrick et al. | |
| 6,116,242 A | 9/2000 | Frye et al. | |
| 6,116,464 A | 9/2000 | Sanders | |
| 6,119,686 A | 9/2000 | Somerson et al. | |

(56) References Cited

U.S. PATENT DOCUMENTS

| | | | |
|---|---|---|---|
| 6,123,073 A | 9/2000 | Schlawin et al. | |
| 6,123,074 A | 9/2000 | Hete et al. | |
| 6,123,674 A | 9/2000 | Rich | |
| 6,131,571 A | 10/2000 | Lampotang et al. | |
| 6,135,106 A | 10/2000 | Dirks et al. | |
| 6,135,967 A | 10/2000 | Fiorenza et al. | |
| 6,138,675 A | 10/2000 | Berthon-Jones | |
| 6,142,150 A | 11/2000 | O'Mahony et al. | |
| 6,148,814 A | 11/2000 | Clemmer et al. | |
| 6,152,132 A | 11/2000 | Psaros | |
| 6,152,135 A | 11/2000 | DeVries et al. | |
| 6,155,986 A | 12/2000 | Brydon et al. | |
| 6,158,432 A | 12/2000 | Biondi et al. | |
| 6,158,433 A | 12/2000 | Ong et al. | |
| 6,161,539 A | 12/2000 | Winter | |
| 6,176,234 B1 | 1/2001 | Salter et al. | |
| 6,179,784 B1 | 1/2001 | Daniels et al. | |
| 6,192,885 B1 | 2/2001 | Jalde | |
| 6,200,271 B1 | 3/2001 | Kuck et al. | |
| 6,203,502 B1 | 3/2001 | Hilgendorf et al. | |
| 6,209,579 B1 | 4/2001 | Rowden et al. | 137/557 |
| 6,210,342 B1 | 4/2001 | Kuck et al. | |
| 6,213,119 B1 | 4/2001 | Brydon et al. | |
| 6,217,524 B1 | 4/2001 | Orr et al. | |
| 6,220,244 B1 | 4/2001 | McLaughlin | |
| 6,220,245 B1 | 4/2001 | Takabayashi et al. | |
| 6,223,064 B1 | 4/2001 | Lynn et al. | |
| 6,227,196 B1 | 5/2001 | Jaffe et al. | |
| 6,230,708 B1 | 5/2001 | Radko | |
| 6,238,351 B1 | 5/2001 | Orr et al. | |
| 6,241,681 B1 | 6/2001 | Haryadi et al. | |
| 6,258,038 B1 | 7/2001 | Haryadi et al. | |
| 6,269,811 B1 | 8/2001 | Duff et al. | 128/204.21 |
| 6,269,812 B1 | 8/2001 | Wallace et al. | |
| 6,273,444 B1 | 8/2001 | Power | |
| 6,283,119 B1 | 9/2001 | Bourdon | |
| 6,287,264 B1 | 9/2001 | Hoffman | |
| 6,295,330 B1 | 9/2001 | Skog et al. | |
| 6,295,985 B1 | 10/2001 | Kock et al. | |
| 6,299,581 B1 | 10/2001 | Rapoport et al. | 600/484 |
| 6,305,373 B1 | 10/2001 | Wallace et al. | |
| 6,305,374 B1 | 10/2001 | Zdrojkowski et al. | |
| 6,306,098 B1 | 10/2001 | Orr et al. | |
| 6,308,706 B1 | 10/2001 | Lammers et al. | |
| 6,309,360 B1 | 10/2001 | Mault | |
| 6,312,389 B1 | 11/2001 | Kofoed et al. | |
| 6,318,365 B1 | 11/2001 | Vogele et al. | |
| 6,321,748 B1 | 11/2001 | O'Mahoney | |
| 6,325,785 B1 | 12/2001 | Babkes et al. | |
| 6,325,978 B1 | 12/2001 | Labuda et al. | |
| 6,341,606 B1 | 1/2002 | Bordewick et al. | 128/206.25 |
| 6,342,039 B1 | 1/2002 | Lynn et al. | |
| 6,345,619 B1 | 2/2002 | Finn | |
| 6,347,631 B1 | 2/2002 | Hansen et al. | 128/207.11 |
| 6,349,922 B1 | 2/2002 | Rydin | |
| 6,355,002 B1 | 3/2002 | Faram et al. | |
| 6,357,438 B1 | 3/2002 | Hansen | |
| 6,358,215 B1 | 3/2002 | Ricciardelli | |
| 6,360,741 B2 | 3/2002 | Truschel | 128/202.22 |
| 6,360,745 B1 | 3/2002 | Wallace et al. | |
| 6,369,838 B1 | 4/2002 | Wallace et al. | |
| 6,371,113 B1 | 4/2002 | Tobia et al. | |
| 6,371,114 B1 | 4/2002 | Schmidt et al. | |
| 6,386,196 B1 | 5/2002 | Culton | 128/205.23 |
| 6,390,091 B1 | 5/2002 | Banner et al. | |
| 6,392,555 B1 | 5/2002 | Most, Jr. | 340/664 |
| 6,394,962 B1 | 5/2002 | Gama De Abreu et al. | |
| 6,397,845 B1 | 6/2002 | Burton | |
| 6,402,697 B1 | 6/2002 | Calkins et al. | |
| 6,402,698 B1 | 6/2002 | Mault | |
| 6,408,848 B1 | 6/2002 | Feldman et al. | |
| 6,412,483 B1 | 7/2002 | Jones et al. | |
| 6,415,788 B1 | 7/2002 | Clawson et al. | |
| 6,418,928 B1 | 7/2002 | Bordewick et al. | 128/205.25 |
| 6,419,634 B1 | 7/2002 | Gaston, IV et al. | |
| 6,427,692 B1 | 8/2002 | Hoglund | |
| 6,431,172 B1 | 8/2002 | Bordewick | 128/207.18 |
| 6,439,229 B1 | 8/2002 | Du et al. | |
| 6,443,154 B1 | 9/2002 | Jalde et al. | |
| 6,450,163 B1 | 9/2002 | Blacker et al. | |
| 6,450,968 B1 | 9/2002 | Wallen et al. | |
| 6,457,472 B1 | 10/2002 | Schwartz et al. | |
| 6,467,477 B1 | 10/2002 | Frank et al. | |
| 6,467,478 B1 | 10/2002 | Merrick et al. | |
| 6,471,658 B1 | 10/2002 | Daniels et al. | |
| 6,488,634 B1 | 12/2002 | Rapoport et al. | 600/538 |
| 6,505,623 B1 | 1/2003 | Hansen | 128/207.11 |
| 6,510,846 B1 | 1/2003 | O'Rourke | |
| 6,512,938 B2 | 1/2003 | Claure et al. | |
| 6,516,802 B2 | 2/2003 | Hansen et al. | 128/207.11 |
| 6,523,537 B1 | 2/2003 | Mas Marfany | |
| 6,523,538 B1 | 2/2003 | Wikefeldt | |
| 6,526,970 B2 | 3/2003 | DeVries et al. | |
| 6,530,373 B1 | 3/2003 | Patron et al. | 128/205.25 |
| 6,532,957 B2 | 3/2003 | Berthon-Jones | |
| 6,532,958 B1 | 3/2003 | Buan et al. | |
| 6,532,959 B1 | 3/2003 | Berthon-Jones | |
| 6,532,960 B1 | 3/2003 | Yurko | |
| 6,536,429 B1 | 3/2003 | Pavlov et al. | |
| 6,537,228 B1 | 3/2003 | Lambert | |
| 6,539,940 B2 | 4/2003 | Zdrojkowski et al. | |
| 6,540,689 B1 | 4/2003 | Orr et al. | |
| 6,543,449 B1 | 4/2003 | Woodring et al. | |
| 6,546,930 B1 | 4/2003 | Emerson et al. | |
| 6,550,479 B1 | 4/2003 | Duxbury | |
| 6,553,991 B1 | 4/2003 | Isaza | |
| 6,557,553 B1 | 5/2003 | Borrello | |
| 6,557,554 B1 | 5/2003 | Sugiura | |
| 6,560,991 B1 | 5/2003 | Kotliar | |
| 6,561,187 B2 | 5/2003 | Schmidt et al. | |
| 6,564,798 B1 | 5/2003 | Jalde | |
| 6,568,387 B2 | 5/2003 | Davenport et al. | |
| 6,571,795 B2 | 6/2003 | Bourdon | |
| 6,571,796 B2 | 6/2003 | Banner et al. | |
| 6,572,561 B2 | 6/2003 | Mault | |
| 6,575,164 B1 | 6/2003 | Jaffe et al. | |
| 6,575,165 B1 | 6/2003 | Cook et al. | |
| 6,575,918 B2 | 6/2003 | Kline | |
| 6,584,973 B1 | 7/2003 | Biondi et al. | |
| 6,588,422 B1 | 7/2003 | Berthon-Jones et al. | |
| 6,588,423 B1 | 7/2003 | Sinderby | |
| 6,591,834 B1 | 7/2003 | Colla et al. | 128/204.21 |
| 6,595,212 B1 | 7/2003 | Arnott | |
| 6,601,583 B2 | 8/2003 | Pessala et al. | |
| 6,606,994 B1 | 8/2003 | Clark | |
| 6,609,016 B1 | 8/2003 | Lynn | |
| 6,609,517 B1 | 8/2003 | Estes et al. | |
| 6,615,828 B1 | 9/2003 | Petherbridge | 128/200.28 |
| 6,616,615 B2 | 9/2003 | Mault | |
| 6,616,896 B2 | 9/2003 | Labuda et al. | |
| 6,619,289 B1 | 9/2003 | Mashak | |
| 6,622,725 B1 | 9/2003 | Fisher et al. | |
| 6,622,726 B1 | 9/2003 | Du | |
| 6,626,175 B2 | 9/2003 | Jafari et al. | |
| 6,629,527 B1 | 10/2003 | Estes et al. | 128/204.18 |
| 6,629,934 B2 | 10/2003 | Mault et al. | |
| 6,631,716 B1 | 10/2003 | Robinson et al. | |
| 6,640,806 B2 | 11/2003 | Yurko | |
| 6,644,310 B1 | 11/2003 | Delache et al. | |
| 6,644,312 B2 | 11/2003 | Berthon-Jones et al. | |
| 6,644,316 B2 | 11/2003 | Bowman et al. | 128/207.12 |
| 6,648,831 B2 | 11/2003 | Orr et al. | |
| 6,648,832 B2 | 11/2003 | Orr et al. | |
| 6,651,656 B2 | 11/2003 | Demers et al. | |
| 6,659,100 B2 | 12/2003 | O'Rourke | |
| 6,659,962 B2 | 12/2003 | Ricciardelli | |
| 6,662,032 B1 | 12/2003 | Gavish et al. | |
| 6,663,574 B2 | 12/2003 | Faram et al. | |
| 6,668,824 B1 | 12/2003 | Isaza et al. | |
| 6,668,830 B1 | 12/2003 | Hansen et al. | 128/206.21 |
| 6,671,529 B2 | 12/2003 | Claure et al. | |
| 6,675,801 B2 | 1/2004 | Wallace et al. | |
| 6,679,258 B1 | 1/2004 | Strom | |
| 6,688,307 B2 | 2/2004 | Berthon-Jones | |

(56) References Cited

U.S. PATENT DOCUMENTS

| | | |
|---|---|---|
| 6,694,978 B1 | 2/2004 | Bennarsten |
| 6,705,314 B1 | 3/2004 | O'Dea |
| 6,718,974 B1 | 4/2004 | Moberg |
| 6,722,359 B2 | 4/2004 | Chalvignac |
| 6,722,360 B2 | 4/2004 | Doshi |
| 6,723,055 B2 | 4/2004 | Hoffman |
| 6,725,447 B1 | 4/2004 | Gilman et al. |
| 6,729,331 B2 | 5/2004 | Kay |
| 6,739,334 B2 | 5/2004 | Valeij |
| 6,739,337 B2 | 5/2004 | Isaza |
| 6,745,768 B2 | 6/2004 | Colla et al. ............ 128/204.21 |
| 6,748,252 B2 | 6/2004 | Lynn et al. |
| 6,752,151 B2 | 6/2004 | Hill |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,772,762 B2 | 8/2004 | Piesinger |
| 6,776,159 B2 | 8/2004 | Pelerossi et al. |
| 6,782,888 B1 | 8/2004 | Friberg et al. |
| 6,786,216 B2 | 9/2004 | O'Rourke |
| 6,793,629 B2 | 9/2004 | Rapoport et al. ............ 600/533 |
| 6,796,305 B1 | 9/2004 | Banner et al. |
| 6,802,225 B2 | 10/2004 | Shahar et al. |
| 6,805,121 B1 | 10/2004 | Flood et al. |
| 6,810,876 B2 | 11/2004 | Berthon-Jones |
| 6,814,074 B1 | 11/2004 | Nadjafizadeh et al. |
| 6,815,211 B1 | 11/2004 | Blazewicz et al. |
| 6,820,618 B2 | 11/2004 | Banner et al. |
| 6,823,866 B2 | 11/2004 | Jafari et al. |
| 6,837,242 B2 | 1/2005 | Younes |
| 6,840,240 B1 | 1/2005 | Berthon-Jones et al. ............ 128/204.21 |
| 6,840,906 B2 | 1/2005 | Gama De Abreu et al. |
| 6,844,691 B2 | 1/2005 | Chiang et al. ............ 318/268 |
| 6,848,444 B2 | 2/2005 | Smith et al. |
| 6,854,462 B2 | 2/2005 | Berthon-Jones et al. |
| 6,863,068 B2 | 3/2005 | Jamison et al. |
| 6,863,656 B2 | 3/2005 | Lurie |
| 6,866,040 B1 | 3/2005 | Bourdon |
| 6,868,346 B2 | 3/2005 | Larson et al. |
| 6,877,511 B2 | 4/2005 | DeVries et al. |
| 6,886,558 B2 | 5/2005 | Tanaka |
| 6,896,713 B1 | 5/2005 | Eckerbom et al. |
| 6,899,103 B1 | 5/2005 | Hood et al. |
| 6,908,438 B2 | 6/2005 | Orr et al. |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,948,497 B2 | 9/2005 | Zdrojkowski et al. |
| 6,954,702 B2 | 10/2005 | Pierry et al. |
| 6,955,651 B2 | 10/2005 | Kück et al. |
| 6,960,854 B2 | 11/2005 | Nadjafizadeh et al. |
| 6,962,155 B1 | 11/2005 | Sinderby |
| 6,968,840 B2 | 11/2005 | Smith et al. |
| 6,986,347 B2 | 1/2006 | Hickle |
| 6,986,349 B2 | 1/2006 | Lurie |
| 6,988,498 B2 | 1/2006 | Berthon-Jones et al. |
| 6,990,980 B2 | 1/2006 | Richey, II |
| 7,000,612 B2 | 2/2006 | Jafari et al. |
| 7,004,168 B2 | 2/2006 | Mace et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,018,340 B2 | 3/2006 | Jaffe et al. |
| 7,032,463 B2 | 4/2006 | Misholi et al. |
| 7,032,589 B2 | 4/2006 | Kerechanin, II et al. |
| 7,036,504 B2 | 5/2006 | Wallace et al. |
| 7,040,315 B1 | 5/2006 | Strömberg |
| 7,040,317 B2 | 5/2006 | Colla et al. ............ 128/204.18 |
| 7,040,318 B2 | 5/2006 | Däscher et al. |
| 7,040,321 B2 | 5/2006 | Göbel |
| 7,043,979 B2 | 5/2006 | Smith et al. |
| 7,056,334 B2 | 6/2006 | Lennox |
| 7,066,173 B2 | 6/2006 | Banner et al. |
| 7,066,175 B2 | 6/2006 | Hamilton et al. |
| 7,066,176 B2 | 6/2006 | Jaffe et al. |
| 7,066,177 B2 | 6/2006 | Pittaway et al. |
| 7,070,570 B2 | 7/2006 | Sanderson et al. |
| 7,074,196 B2 | 7/2006 | Kück et al. |
| 7,077,131 B2 | 7/2006 | Hansen |
| 7,077,132 B2 | 7/2006 | Berthon-Jones |
| 7,080,646 B2 | 7/2006 | Wiesmann et al. |
| 7,081,095 B2 | 7/2006 | Lynn et al. |
| RE39,225 E | 8/2006 | Isaza et al. |
| 7,087,027 B2 | 8/2006 | Page |
| 7,089,930 B2 | 8/2006 | Adams et al. ............ 128/201.27 |
| 7,089,932 B2 | 8/2006 | Dodds |
| 7,089,936 B2 | 8/2006 | Madaus et al. |
| 7,089,937 B2 | 8/2006 | Berthon-Jones et al. |
| 7,092,757 B2 | 8/2006 | Larson et al. |
| 7,096,866 B2 | 8/2006 | Be'eri et al. |
| 7,100,607 B2 | 9/2006 | Zdrojkowski et al. |
| 7,100,608 B2 | 9/2006 | Brewer et al. ............ 128/204.23 |
| 7,100,609 B2 | 9/2006 | Berthon-Jones et al. |
| 7,101,341 B2 | 9/2006 | Tsukashima et al. ............ 600/532 |
| 7,104,962 B2 | 9/2006 | Lomask et al. |
| 7,117,438 B2 | 10/2006 | Wallace et al. |
| 7,118,537 B2 | 10/2006 | Baddour |
| 7,121,277 B2 | 10/2006 | Ström |
| 7,122,010 B2 | 10/2006 | Böhm et al. |
| 7,128,069 B2 | 10/2006 | Farrugia et al. |
| 7,135,001 B2 | 11/2006 | Orr et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,156,095 B2 | 1/2007 | Melker et al. |
| 7,168,597 B1 | 1/2007 | Jones et al. |
| 7,183,552 B2 | 2/2007 | Russell |
| 7,195,013 B2 | 3/2007 | Lurie |
| 7,204,251 B2 | 4/2007 | Lurie |
| 7,210,478 B2 | 5/2007 | Banner et al. |
| 7,211,049 B2 | 5/2007 | Bradley et al. |
| 7,219,666 B2 | 5/2007 | Friberg et al. |
| 7,222,623 B2 | 5/2007 | DeVries et al. |
| 7,229,430 B2 | 6/2007 | Hickle et al. |
| 7,241,269 B2 | 7/2007 | McCawley et al. |
| 7,246,618 B2 | 7/2007 | Habashi |
| 7,255,103 B2 | 8/2007 | Bassin |
| 7,267,122 B2 | 9/2007 | Hill |
| 7,267,652 B2 | 9/2007 | Coyle et al. |
| 7,270,126 B2 | 9/2007 | Wallace et al. |
| 7,270,128 B2 | 9/2007 | Berthon-Jones et al. |
| 7,275,540 B2 | 10/2007 | Bolam et al. |
| 7,276,031 B2 | 10/2007 | Norman et al. |
| 7,278,962 B2 | 10/2007 | Lönneker-Lammers |
| 7,290,544 B1 | 11/2007 | Särelä et al. |
| 7,291,115 B2 | 11/2007 | Cardona Burrul |
| 7,291,851 B2 | 11/2007 | DelFavero et al. |
| 7,296,573 B2 | 11/2007 | Estes et al. |
| 7,297,119 B2 | 11/2007 | Westbrook et al. |
| 7,297,120 B2 | 11/2007 | Tsukashima et al. ............ 600/532 |
| 7,302,949 B2 | 12/2007 | Pelerossi et al. |
| 7,308,894 B2 | 12/2007 | Hickle |
| 7,311,668 B2 | 12/2007 | Lurie |
| 7,320,321 B2 | 1/2008 | Pranger et al. |
| 7,331,343 B2 | 2/2008 | Schmidt et al. |
| 7,335,164 B2 | 2/2008 | Mace et al. |
| 7,341,563 B2 | 3/2008 | Rich et al. |
| 7,347,205 B2 | 3/2008 | Levi |
| 7,347,825 B2 | 3/2008 | Vaughan et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,390,304 B2 | 6/2008 | Chen et al. |
| 7,392,806 B2 | 7/2008 | Yuen et al. |
| 7,398,115 B2 | 7/2008 | Lynn |
| 7,406,870 B2 | 8/2008 | Seto |
| 7,427,269 B2 | 9/2008 | George et al. |
| 7,428,902 B2 | 9/2008 | Du et al. |
| 7,432,508 B2 | 10/2008 | Daniels et al. |

(56) References Cited

U.S. PATENT DOCUMENTS

| | | |
|---|---|---|
| 7,448,381 B2 | 11/2008 | Sasaki et al. |
| 7,455,583 B2 | 11/2008 | Taya |
| 7,460,959 B2 | 12/2008 | Jafari |
| 7,465,275 B2 | 12/2008 | Stenqvist |
| 7,467,012 B1 | 12/2008 | Park et al. |
| 7,472,702 B2 | 1/2009 | Beck et al. |
| 7,475,685 B2 | 1/2009 | Dietz et al. |
| 7,478,634 B2 | 1/2009 | Jam |
| 7,481,222 B2 | 1/2009 | Reissmann |
| 7,484,508 B2 | 2/2009 | Younes |
| 7,487,773 B2 | 2/2009 | Li |
| 7,487,774 B2 | 2/2009 | Acker |
| 7,487,778 B2 | 2/2009 | Freitag |
| 7,500,483 B2 | 3/2009 | Colman et al. |
| 7,509,957 B2 | 3/2009 | Duquette et al. |
| 7,520,279 B2 | 4/2009 | Berthon-Jones |
| 7,525,663 B2 | 4/2009 | Kwok et al. |
| 7,527,054 B2 | 5/2009 | Misholi |
| 7,527,058 B2 | 5/2009 | Wright et al. |
| 7,533,670 B1 | 5/2009 | Freitag et al. |
| RE40,814 E | 6/2009 | Van Brunt et al. |
| 7,547,285 B2 | 6/2009 | Kline |
| 7,552,731 B2 | 6/2009 | Jorczak et al. |
| 7,556,038 B2 | 7/2009 | Kirby et al. |
| 7,556,041 B2 | 7/2009 | Madsen |
| 7,556,042 B2 | 7/2009 | West et al. |
| 7,562,657 B2 | 7/2009 | Blanch et al. |
| 7,574,368 B2 | 8/2009 | Pawlikowski et al. |
| 7,581,708 B2 | 9/2009 | Newkirk |
| 7,588,033 B2 | 9/2009 | Wondka |
| 7,607,360 B2 | 10/2009 | Todokoro et al. |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,628,151 B2 | 12/2009 | Bassin |
| 7,634,998 B1 | 12/2009 | Fenley |
| 7,644,713 B2 | 1/2010 | Berthon-Jones |
| 7,654,802 B2 | 2/2010 | Crawford, Jr. et al. |
| 7,668,579 B2 | 2/2010 | Lynn |
| 7,672,720 B2 | 3/2010 | Heath |
| 7,682,312 B2 | 3/2010 | Lurie |
| 7,686,019 B2 | 3/2010 | Weiss |
| 7,694,677 B2 | 4/2010 | Tang |
| 7,699,788 B2 | 4/2010 | Kuck et al. |
| 7,708,015 B2 | 5/2010 | Seeger et al. |
| 7,717,113 B2 | 5/2010 | Andrieux |
| 7,717,858 B2 | 5/2010 | Massad |
| 7,721,735 B2 | 5/2010 | Hamilton et al. |
| 7,721,736 B2 | 5/2010 | Urias et al. |
| 7,722,546 B2 | 5/2010 | Madaus et al. |
| D618,356 S | 6/2010 | Ross |
| 7,730,884 B2 | 6/2010 | Sato et al. |
| 7,735,486 B2 | 6/2010 | Payne |
| 7,735,492 B2 | 6/2010 | Doshi et al. |
| 7,740,591 B1 | 6/2010 | Starr et al. |
| 7,753,052 B2 | 7/2010 | Tanaka |
| 7,758,503 B2 | 7/2010 | Lynn et al. |
| 7,775,207 B2 | 8/2010 | Jaffe et al. |
| 7,779,834 B2 | 8/2010 | Calluaud et al. |
| 7,779,840 B2 | 8/2010 | Acker et al. |
| 7,784,461 B2 | 8/2010 | Figueiredo et al. |
| 7,793,656 B2 | 9/2010 | Johnson |
| 7,798,145 B2 | 9/2010 | Weismann et al. |
| 7,798,148 B2 | 9/2010 | Doshi et al. |
| 7,802,571 B2 | 9/2010 | Tehrani |
| 7,806,120 B2 | 10/2010 | Loomas et al. |
| 7,810,496 B2 | 10/2010 | Estes et al. |
| 7,810,497 B2 | 10/2010 | Pittman et al. |
| 7,810,498 B1 | 10/2010 | Patterson |
| 7,814,908 B2 | 10/2010 | Psaros |
| 7,819,815 B2 | 10/2010 | Younes |
| 7,823,588 B2 | 11/2010 | Hansen |
| 7,828,741 B2 | 11/2010 | Kline et al. |
| 7,841,347 B2 | 11/2010 | Sonnenschein et al. |
| 7,846,739 B2 | 12/2010 | von Bahr et al. |
| 7,849,854 B2 | 12/2010 | DeVries et al. |
| 7,850,619 B2 | 12/2010 | Gavish et al. |
| 7,855,716 B2 | 12/2010 | McCreary et al. |
| 7,861,716 B2 | 1/2011 | Borrello |
| 7,866,318 B2 | 1/2011 | Bassin |
| 7,870,857 B2 | 1/2011 | Dhuper et al. |
| D632,796 S | 2/2011 | Ross et al. |
| D632,797 S | 2/2011 | Ross et al. |
| 7,883,471 B2 | 2/2011 | Aljuri et al. |
| 7,885,771 B2 | 2/2011 | Roecker et al. |
| 7,886,739 B2 | 2/2011 | Soliman et al. |
| 7,891,354 B2 | 2/2011 | Farbarik |
| 7,893,560 B2 | 2/2011 | Carter |
| 7,900,626 B2 | 3/2011 | Daly |
| 7,909,034 B2 | 3/2011 | Sinderby et al. |
| 7,913,690 B2 | 3/2011 | Fisher et al. |
| D638,852 S | 5/2011 | Skidmore et al. |
| 7,938,114 B2 | 5/2011 | Matthews et al. |
| 7,963,283 B2 | 6/2011 | Sinderby |
| 7,970,475 B2 | 6/2011 | Tehrani et al. |
| 7,971,589 B2 | 7/2011 | Mashak et al. |
| 7,975,691 B2 | 7/2011 | Cha et al. .................. 128/204.22 |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| D645,158 S | 9/2011 | Sanchez et al. |
| 8,011,363 B2 | 9/2011 | Johnson |
| 8,011,364 B2 | 9/2011 | Johnson |
| 8,011,366 B2 | 9/2011 | Knepper |
| 8,015,974 B2 | 9/2011 | Christopher et al. |
| 8,020,558 B2 | 9/2011 | Christopher et al. |
| 8,021,308 B2 | 9/2011 | Carlson et al. |
| 8,021,309 B2 | 9/2011 | Zilberg |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| 8,844,526 B2 | 9/2014 | Jafari et al. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2001/0029339 A1 | 10/2001 | Orr et al. |
| 2001/0031928 A1 | 10/2001 | Orr et al. |
| 2002/0005197 A1 | 1/2002 | DeVries et al. ......... 128/204.21 |
| 2002/0014239 A1 | 2/2002 | Chalvignac ............... 128/204.18 |
| 2002/0014240 A1 | 2/2002 | Truschel |
| 2002/0017301 A1 | 2/2002 | Lundin |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0053345 A1 | 5/2002 | Jafari et al. ............... 128/204.23 |
| 2002/0117173 A1 | 8/2002 | Lynn et al. |
| 2002/0128566 A1 | 9/2002 | Gama De Abreu et al. |

(56) References Cited

U.S. PATENT DOCUMENTS

| | | |
|---|---|---|
| 2002/0138213 A1 | 9/2002 | Mault |
| 2002/0144681 A1 | 10/2002 | Cewers et al. |
| 2002/0185126 A1 | 12/2002 | Krebs |
| 2003/0029453 A1 | 2/2003 | Smith et al. |
| 2003/0047188 A1 | 3/2003 | Mace et al. |
| 2003/0062045 A1 | 4/2003 | Woodring et al. |
| 2003/0066529 A1 | 4/2003 | Truschel ............... 128/204.12 |
| 2003/0140925 A1 | 7/2003 | Sapienza et al. |
| 2003/0168066 A1 | 9/2003 | Sallvin |
| 2003/0172929 A1 | 9/2003 | Muellner |
| 2003/0191405 A1 | 10/2003 | Rich et al. |
| 2003/0225339 A1 | 12/2003 | Orr et al. |
| 2004/0015058 A1 | 1/2004 | Besson et al. ............... 600/301 |
| 2004/0050387 A1 | 3/2004 | Younes ............... 128/204.18 |
| 2004/0087867 A1 | 5/2004 | Gama De Abreu et al. |
| 2004/0138577 A1 | 7/2004 | Kline |
| 2004/0149282 A1 | 8/2004 | Hickle |
| 2004/0186391 A1 | 9/2004 | Pierry et al. |
| 2004/0226561 A1 | 11/2004 | Colla et al. ............... 128/204.21 |
| 2004/0244804 A1 | 12/2004 | Olsen et al. |
| 2004/0256560 A1 | 12/2004 | Russell |
| 2004/0261793 A1 | 12/2004 | Stromberg et al. |
| 2005/0034724 A1 | 2/2005 | O'Dea |
| 2005/0034727 A1 | 2/2005 | Shusterman et al. |
| 2005/0039748 A1 | 2/2005 | Andrieux |
| 2005/0061321 A1 | 3/2005 | Jones |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0087187 A1 | 4/2005 | Berton-Jones et al. . 128/200.24 |
| 2005/0087190 A1 | 4/2005 | Jafari et al. ............... 128/204.21 |
| 2005/0098177 A1 | 5/2005 | Haj-Yahya et al. |
| 2005/0113668 A1 | 5/2005 | Srinivasan |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0166928 A1 | 8/2005 | Jiang |
| 2005/0172965 A1 | 8/2005 | Thulin |
| 2005/0217671 A1 | 10/2005 | Fisher et al. |
| 2005/0247311 A1 | 11/2005 | Vacchiano et al. |
| 2005/0263155 A1 | 12/2005 | Gossweiler ............... 128/205.23 |
| 2005/0279358 A1 | 12/2005 | Richey, II |
| 2005/0285055 A1 | 12/2005 | DelFavero et al. |
| 2006/0009707 A1 | 1/2006 | Daniels et al. |
| 2006/0021618 A1 | 2/2006 | Berthon-Jones et al. |
| 2006/0032499 A1 | 2/2006 | Halsnes |
| 2006/0052950 A1 | 3/2006 | Pierry et al. |
| 2006/0070624 A1 | 4/2006 | Kane et al. ............... 128/204.23 |
| 2006/0086357 A1 | 4/2006 | Soliman et al. |
| 2006/0107953 A1 | 5/2006 | Truschel et al. ......... 128/204.18 |
| 2006/0112959 A1 | 6/2006 | Mechlenburg et al. |
| 2006/0122662 A1 | 6/2006 | Tehrani et al. |
| 2006/0129054 A1 | 6/2006 | Orr et al. |
| 2006/0130839 A1 | 6/2006 | Bassovitch |
| 2006/0142815 A1 | 6/2006 | Tehrani et al. |
| 2006/0145078 A1 | 7/2006 | Russell |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0196507 A1 | 9/2006 | Bradley |
| 2006/0196508 A1 | 9/2006 | Chalvignac |
| 2006/0201507 A1 | 9/2006 | Breen |
| 2006/0235324 A1 | 10/2006 | Lynn |
| 2006/0241508 A1 | 10/2006 | Jaffe et al. |
| 2006/0241708 A1 | 10/2006 | Boute |
| 2006/0249148 A1 | 11/2006 | Younes |
| 2006/0249153 A1 | 11/2006 | DeVries et al. |
| 2006/0253038 A1 | 11/2006 | Kuck et al. |
| 2006/0264762 A1 | 11/2006 | Starr |
| 2006/0272637 A1 | 12/2006 | Johnson |
| 2006/0272642 A1 | 12/2006 | Chalvignac |
| 2006/0283451 A1 | 12/2006 | Albertelli |
| 2007/0000494 A1 | 1/2007 | Banner et al. |
| 2007/0017515 A1 | 1/2007 | Wallace et al. |
| 2007/0017518 A1 | 1/2007 | Farrugia et al. |
| 2007/0017522 A1 | 1/2007 | Be-Eri et al. |
| 2007/0017523 A1 | 1/2007 | Be-Eri et al. |
| 2007/0027375 A1 | 2/2007 | Melker et al. |
| 2007/0028921 A1 | 2/2007 | Banner et al. |
| 2007/0044798 A1 | 3/2007 | Levi |
| 2007/0044805 A1 | 3/2007 | Wedler et al. |
| 2007/0056588 A1 | 3/2007 | Hayek |
| 2007/0062531 A1 | 3/2007 | Fisher et al. |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0068530 A1 | 3/2007 | Pacey |
| 2007/0072541 A1 | 3/2007 | Daniels, II et al. |
| 2007/0073183 A1 | 3/2007 | Kline |
| 2007/0077200 A1 | 4/2007 | Baker |
| 2007/0089741 A1 | 4/2007 | Bohm et al. |
| 2007/0093721 A1 | 4/2007 | Lynn et al. |
| 2007/0095347 A1 | 5/2007 | Lampotang et al. |
| 2007/0107728 A1 | 5/2007 | Ricciardelli et al. |
| 2007/0113854 A1 | 5/2007 | Mcauliffe |
| 2007/0123792 A1 | 5/2007 | Kline |
| 2007/0125377 A1 | 6/2007 | Heinonen et al. |
| 2007/0129646 A1 | 6/2007 | Heinonen et al. |
| 2007/0129647 A1 | 6/2007 | Lynn |
| 2007/0142716 A1 | 6/2007 | Biondi |
| 2007/0144521 A1 | 6/2007 | DeVries et al. |
| 2007/0144523 A1 | 6/2007 | Bolam et al. |
| 2007/0149860 A1 | 6/2007 | Lynn et al. |
| 2007/0149891 A1 | 6/2007 | George et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0181122 A1 | 8/2007 | Mulier |
| 2007/0191697 A1 | 8/2007 | Lynn et al. |
| 2007/0199566 A1 | 8/2007 | Be'eri |
| 2007/0215154 A1 | 9/2007 | Borrello |
| 2007/0227537 A1 | 10/2007 | Bemister et al. |
| 2007/0232952 A1 | 10/2007 | Baddour |
| 2007/0255160 A1 | 11/2007 | Daly |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0277823 A1 | 12/2007 | Al-Ali et al. |
| 2007/0282214 A1 | 12/2007 | George et al. |
| 2007/0283958 A1 | 12/2007 | Naghavi |
| 2007/0284361 A1 | 12/2007 | Nadjafizadeh et al. |
| 2008/0000475 A1 | 1/2008 | Hill |
| 2008/0000479 A1 | 1/2008 | Elaz et al. |
| 2008/0011296 A1 | 1/2008 | Schatzl |
| 2008/0021339 A1 | 1/2008 | Gabriel et al. |
| 2008/0021379 A1 | 1/2008 | Hickle |
| 2008/0033304 A1 | 2/2008 | Dalal et al. |
| 2008/0041383 A1 | 2/2008 | Matthews et al. |
| 2008/0045825 A1 | 2/2008 | Melker et al. |
| 2008/0045845 A1 | 2/2008 | Pfeiffer et al. |
| 2008/0053438 A1 | 3/2008 | DeVries et al. |
| 2008/0053441 A1 | 3/2008 | Gottlib et al. |
| 2008/0058667 A1 | 3/2008 | Pierry et al. |
| 2008/0060646 A1 | 3/2008 | Isaza |
| 2008/0060656 A1 | 3/2008 | Isaza |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0072904 A1 | 3/2008 | Becker et al. |
| 2008/0078390 A1 | 4/2008 | Milne et al. |
| 2008/0078395 A1 | 4/2008 | Ho et al. |
| 2008/0081974 A1 | 4/2008 | Pav |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0110461 A1 | 5/2008 | Mulqueeny et al. |
| 2008/0110462 A1 | 5/2008 | Chekal et al. |
| 2008/0119753 A1 | 5/2008 | Ricciardelli et al. |

(56) References Cited

U.S. PATENT DOCUMENTS

| | | |
|---|---|---|
| 2008/0135044 A1 | 6/2008 | Freitag et al. |
| 2008/0163872 A1 | 7/2008 | Negele et al. |
| 2008/0168990 A1 | 7/2008 | Cooke et al. |
| 2008/0177404 A1 | 7/2008 | Bonnat ............ 700/90 |
| 2008/0178874 A1 | 7/2008 | Doshi et al. |
| 2008/0178880 A1 | 7/2008 | Christopher et al. |
| 2008/0178882 A1 | 7/2008 | Christopher et al. |
| 2008/0183057 A1 | 7/2008 | Taube |
| 2008/0183094 A1 | 7/2008 | Schonfuss et al. |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0196720 A1 | 8/2008 | Kollmeyer et al. |
| 2008/0200775 A1 | 8/2008 | Lynn |
| 2008/0200776 A1 | 8/2008 | Schermeier et al. ......... 600/301 |
| 2008/0200819 A1 | 8/2008 | Lynn et al. |
| 2008/0202517 A1 | 8/2008 | Mitton et al. |
| 2008/0202518 A1 | 8/2008 | Mitton et al. |
| 2008/0202525 A1 | 8/2008 | Mitton et al. |
| 2008/0202528 A1 | 8/2008 | Carter et al. |
| 2008/0208281 A1 | 8/2008 | Tehrani et al. |
| 2008/0214947 A1 | 9/2008 | Hunt et al. |
| 2008/0221470 A1 | 9/2008 | Sather et al. |
| 2008/0223361 A1 | 9/2008 | Nieuwstad |
| 2008/0230061 A1 | 9/2008 | Tham |
| 2008/0230062 A1 | 9/2008 | Tham |
| 2008/0236582 A1 | 10/2008 | Tehrani |
| 2008/0251079 A1 | 10/2008 | Richey |
| 2008/0255467 A1 | 10/2008 | Acker et al. |
| 2008/0257349 A1 | 10/2008 | Hedner et al. |
| 2008/0276939 A1 | 11/2008 | Tiedje |
| 2008/0283060 A1 | 11/2008 | Bassin |
| 2008/0295837 A1 | 12/2008 | McCormick et al. |
| 2008/0312519 A1 | 12/2008 | Maschke |
| 2008/0314385 A1 | 12/2008 | Brunner et al. |
| 2009/0000621 A1 | 1/2009 | Haggblom et al. |
| 2009/0007914 A1 | 1/2009 | Bateman |
| 2009/0013999 A1 | 1/2009 | Bassin |
| 2009/0020119 A1 | 1/2009 | Eger et al. |
| 2009/0038617 A1 | 2/2009 | Berthon-Jones et al. |
| 2009/0050153 A1 | 2/2009 | Brunner |
| 2009/0056708 A1 | 3/2009 | Stenzler et al. |
| 2009/0056719 A1 | 3/2009 | Newman, Jr. |
| 2009/0071478 A1 | 3/2009 | Kalfon |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0095297 A1 | 4/2009 | Hallett |
| 2009/0099621 A1 | 4/2009 | Lin et al. |
| 2009/0107982 A1 | 4/2009 | McGhin et al. |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0139522 A1 | 6/2009 | Thomson et al. |
| 2009/0145441 A1 | 6/2009 | Doshi et al. |
| 2009/0159082 A1 | 6/2009 | Eger |
| 2009/0165795 A1 | 7/2009 | Nadjafizadeh et al. |
| 2009/0165798 A1 | 7/2009 | Cong et al. |
| 2009/0171176 A1 | 7/2009 | Andersohn |
| 2009/0171226 A1 | 7/2009 | Campbell et al. |
| 2009/0183739 A1 | 7/2009 | Wondka |
| 2009/0188502 A1 | 7/2009 | Tiedje |
| 2009/0194109 A1 | 8/2009 | Doshi et al. |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0210032 A1 | 8/2009 | Beiski et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. et al. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250054 A1 | 10/2009 | Loncar et al. |
| 2009/0250058 A1 | 10/2009 | Lastow et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0266360 A1 | 10/2009 | Acker et al. |
| 2009/0270752 A1 | 10/2009 | Coifman |
| 2009/0272381 A1 | 11/2009 | Dellaca et al. |
| 2009/0277448 A1 | 11/2009 | Ahlmén et al. |
| 2009/0293872 A1 | 12/2009 | Bocke |
| 2009/0293877 A1 | 12/2009 | Blanch et al. |
| 2009/0299155 A1 | 12/2009 | Yang et al. |
| 2009/0299430 A1 | 12/2009 | Davies et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308393 A1 | 12/2009 | Luceros |
| 2009/0308394 A1 | 12/2009 | Levi |
| 2009/0308398 A1 | 12/2009 | Ferdinand et al. |
| 2009/0314297 A1 | 12/2009 | Mathews |
| 2010/0006098 A1 | 1/2010 | McGinnis et al. |
| 2010/0011307 A1 | 1/2010 | Desfossez et al. |
| 2010/0012126 A1 | 1/2010 | Gandini |
| 2010/0016694 A1 | 1/2010 | Martin et al. |
| 2010/0018531 A1 | 1/2010 | Bassin |
| 2010/0024818 A1 | 2/2010 | Stenzler et al. |
| 2010/0024820 A1 | 2/2010 | Bourdon |
| 2010/0031443 A1 | 2/2010 | Georgiev et al. |
| 2010/0031961 A1 | 2/2010 | Schmidt |
| 2010/0051026 A1 | 3/2010 | Graboi |
| 2010/0051029 A1 | 3/2010 | Jafari et al. |
| 2010/0059058 A1 | 3/2010 | Kuo |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078018 A1 | 4/2010 | Heinonen et al. |
| 2010/0078024 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0089396 A1 | 4/2010 | Richard et al. |
| 2010/0094366 A1 | 4/2010 | McCarthy |
| 2010/0099999 A1 | 4/2010 | Hemnes et al. |
| 2010/0101575 A1 | 4/2010 | Fedorko et al. |
| 2010/0101577 A1 | 4/2010 | Kaestle et al. |
| 2010/0106037 A1 | 4/2010 | Kacmarek et al. |
| 2010/0108066 A1 | 5/2010 | Martin et al. |
| 2010/0108070 A1 | 5/2010 | Kwok |
| 2010/0114218 A1 | 5/2010 | Heath |
| 2010/0116270 A1 | 5/2010 | Edwards et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0148458 A1 | 6/2010 | Ross et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |

(56) References Cited

U.S. PATENT DOCUMENTS

| | | |
|---|---|---|
| 2010/0185112 A1 | 7/2010 | Van Kesteren et al. |
| 2010/0186742 A1 | 7/2010 | Sherman et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252037 A1 | 10/2010 | Wondka et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252046 A1 | 10/2010 | Dahlström et al. |
| 2010/0258124 A1 | 10/2010 | Madaus et al. |
| 2010/0268106 A1 | 10/2010 | Johnson et al. |
| 2010/0268131 A1 | 10/2010 | Efthimiou |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282258 A1 | 11/2010 | Tailor et al. |
| 2010/0282259 A1 | 11/2010 | Figueiredo et al. |
| 2010/0286544 A1 | 11/2010 | Tanaka et al. |
| 2010/0288283 A1 | 11/2010 | Campbell et al. |
| 2010/0292544 A1 | 11/2010 | Sherman et al. |
| 2010/0292601 A1 | 11/2010 | Dompeling et al. |
| 2010/0300445 A1 | 12/2010 | Chatburn et al. |
| 2010/0300446 A1 | 12/2010 | Nicolazzi et al. |
| 2010/0307507 A1 | 12/2010 | Li et al. |
| 2010/0319691 A1 | 12/2010 | Lurie et al. |
| 2010/0324437 A1 | 12/2010 | Freeman et al. |
| 2010/0324439 A1 | 12/2010 | Davenport |
| 2010/0326442 A1 | 12/2010 | Hamilton et al. |
| 2010/0326447 A1 | 12/2010 | Loomas et al. |
| 2010/0331639 A1 | 12/2010 | O'Reilly |
| 2010/0331877 A1 | 12/2010 | Li et al. |
| 2011/0004108 A1 | 1/2011 | Peyton |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0017214 A1 | 1/2011 | Tehrani |
| 2011/0023875 A1 | 2/2011 | Ledwith |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0061650 A1 | 3/2011 | Heesch |
| 2011/0066060 A1 | 3/2011 | von Bahr et al. |
| 2011/0073112 A1 | 3/2011 | DiBlasi et al. |
| 2011/0088697 A1 | 4/2011 | DeVries et al. |
| 2011/0092841 A1 | 4/2011 | Bassin |
| 2011/0100365 A1 | 5/2011 | Wedler et al. |
| 2011/0108041 A1 | 5/2011 | Sather et al. |
| 2011/0112424 A1 | 5/2011 | Kesselman et al. |
| 2011/0112425 A1 | 5/2011 | Muhlsteff et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209706 A1 | 9/2011 | Truschel et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |

(56) References Cited

U.S. PATENT DOCUMENTS

| | | |
|---|---|---|
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2016/0045694 A1 | 2/2016 | Esmaeil-zadeh-azar |
| 2016/0114115 A1 | 4/2016 | Glenn et al. |

FOREIGN PATENT DOCUMENTS

| | | | | |
|---|---|---|---|---|
| DE | 4038871 A1 | 6/1992 | ............ | A61M 16/00 |
| DE | 197 14 644 A | 10/1998 | ............ | A61M 16/00 |
| EP | 0042321 A1 | 6/1981 | ............ | A61M 16/00 |
| EP | 0046570 | 3/1982 | ............ | A61M 16/00 |
| EP | 283141 A2 | 2/1988 | ............ | A61M 16/00 |
| EP | 0402951 A2 | 6/1990 | ............ | A61M 16/00 |
| EP | 0459647 | 12/1991 | ............ | A61M 16/00 |
| EP | 0504725 A2 | 9/1992 | ............ | A61B 5/083 |
| EP | 0504945 | 9/1992 | ............ | A61B 10/00 |
| EP | 0099743 | 2/1994 | ............ | A61M 16/00 |
| EP | 0621056 A1 | 10/1994 | ............ | A62B 18/00 |
| EP | 0661071 B1 | 7/1995 | ............ | A61M 16/00 |
| EP | 0742027 | 11/1996 | ............ | A61M 16/00 |
| EP | 0774233 A1 | 5/1997 | ............ | A61B 5/08 |
| EP | 850652 | 7/1998 | | |
| EP | 0862922 A | 9/1998 | ............ | A61M 16/00 |
| EP | 1243282 A | 9/2002 | ............ | A61M 16/00 |
| EP | 1502619 | 2/2005 | | |
| FR | 2663547 A1 | 6/1990 | ............ | A61M 16/00 |
| FR | 2695830 A1 | 9/1992 | ............ | A61M 16/00 |
| FR | 2822384 A1 | 9/2002 | ............ | A61M 16/00 |
| GB | 2054387 A | 6/1980 | ............ | A61M 16/00 |
| GB | 2215216 B1 | 9/1989 | ............ | A62B 7/10 |
| GB | 2294400 | 5/1996 | ............ | A61M 16/00 |
| GB | 2324122 A | 10/1998 | ............ | F04D 29/30 |
| JP | 2002136595 | 5/2002 | | |
| WO | WO 88/10108 | 12/1988 | ............ | A61F 5/56 |
| WO | WO 89/10768 | 11/1989 | ............ | A61M 16/00 |
| WO | WO 89/11823 | 12/1989 | ............ | A61B 5/08 |
| WO | WO 90/14121 | 11/1990 | ............ | A61M 16/00 |
| WO | WO 91/06832 | 5/1991 | ............ | G01F 1/64 |
| WO | 91/19526 | 12/1991 | ............ | A61M 16/10 |
| WO | WO 91/19526 | 12/1991 | | |
| WO | WO 9211054 | 7/1992 | ............ | A61M 16/00 |
| WO | 9215355 A1 | 9/1992 | ............ | A61M 16/00 |
| WO | WO 9321982 | 11/1993 | ............ | A61M 16/00 |
| WO | WO 9325260 | 12/1993 | ............ | A61M 16/00 |
| WO | WO 95/28874 | 11/1995 | | |
| WO | 9603174 A1 | 2/1996 | ............ | A61M 16/00 |
| WO | WO 96/08285 | 3/1996 | ............ | A61M 16/00 |
| WO | WO 96/41571 | 12/1996 | | |
| WO | 9933508 A1 | 7/1999 | ............ | A61M 16/04 |
| WO | 00/24447 | 5/2000 | ............ | A61M 16/00 |
| WO | 0027457 A1 | 5/2000 | ............ | A61M 16/00 |
| WO | 02/26305 | 4/2002 | ............ | A61M 16/00 |
| WO | WO 03055552 A1 | 7/2003 | | |
| WO | WO 04000114 | 12/2003 | | |
| WO | 2004/024053 | 3/2004 | ............ | A61M 16/00 |
| WO | WO 2004/024053 | 3/2004 | | |
| WO | 2007/035804 | 3/2007 | ............ | A61M 16/00 |
| WO | WO 2007/035804 | 3/2007 | | |
| WO | WO 2007085110 | 8/2007 | | |
| WO | WO 2007/102866 | 9/2007 | | |
| WO | WO 2007145948 | 12/2007 | | |
| WO | WO 2008/092021 | 7/2008 | | |

OTHER PUBLICATIONS

Conference Proceedings, the New Generation of Mechanical Ventilators, Respiratory Care, vol. 32 No. 6, pp. 403-418, Jun. 1987.

International PCT Search Report with Written Opinion, PCT/US2007/077195, 3 pages, Feb. 14, 2008.

International PCT Search Report and Written Opinion, PCT/US2009/055280, 22 pages, Mar. 24, 2010.

"GoodKnight® 425 GoodKnight® 425ST Clinician and Home Care Provider Manual", Puritan Bennett, Revision G, p. 25, referring to breathing circuits having an "internal pressure sensor line", Mar. 2010.

"Puritan Bennett CPAP / BiLEVEL Tubing with Internal Pressure Sensor Line", Printout of page from website www.cpapxchange.com, 2 pages, Printed Jun. 9, 2010.

Ballard, Robert, et al., "Sleep Apnea—Diagnosis and Treatment", Topics in Primary Care Medicine, The Western Journal of Medicine, 145:249-250, Aug. 1986.

Guilleminault, C. et al.; "Unattended CPAP Titration: Toward a Smart Machine"; 1992; pp. 342 [Sleep Research, vol. 21].

Miles, L.E. et al.; "Development and Application of an Automatic Nasal CPAP Calibration Procedures for Use in the Unsupervised Home Environment"; pp. S118-S119 [Supplemental Issue: Sleep and Breathing, vol. 16.], Dec. 1993.

Miles, L.E. et al.; "Different Roles for an Automatic Nasal CPAP Calibration Procedure and Smart Pap", Sleep Research 21, p. 238, 1993.

Remmers, et al.; "Mechanics of the Pharynx in Patients With Obstructive Sleep Apnea"; pp. 261-271 [Sleep and Respiration], 1990.

Miles, L.E. et al.; "Development and Application of an Automatic Nasal CPAP Calibration Procedure for Use in the Unsupervised Home Environment"; p. 352 [Sleep Research, vol. 21], 1992.

(56) References Cited

OTHER PUBLICATIONS

Dupuis, Yvon G., "Ventilators—Theory and Clinical Application", The C.V.Mosby Co., pp. 107-117, 1986.
Sullivan et al., Reversal of Obstructive Sleep Apnea by Continuous Positive Airway Pressure Applied Through the Nares, The Lancet, vol. 1, No. 8225, pp. 862-865, 1981.
International Preliminary Examination Report for Relating International Application PCT/FR93/00902, Jun. 9, 1994.
Rapapart et al., "Reversal of the Pickwickian Syndrome by Long-term use of Nocturnal Nasal-Airway Pressure", New England Journal of Medicine, vol. 307, No. 15, pp. 931-933, 1982.
Operating Manual for Siemens Servo ventilator 300, May 1993.
Service Manual for Siemens Servo Ventilator 300, Feb. 1994.
Schwartz et al., "Induction of Upper Airway Occlusion in Sleeping Individuals with Subatmospheric Nasal Pressure", Journal of Applied Physiology, pp. 535-542, 1988.
Southworth et al., "Digital Computation and Numerical Methods", McGraw-Hill, Inc., pp. 6-10, 1965.
Rapoport, "Techniques for Administering Nasal CPAP", Respiratory Management, pp. 18-21, 1987.
Garay, "Therapeutic Options for Obstructive Sleep Apnea", Respiratory Management, pp. 11-15, 1987.
Technical Brochure of the SV300, Mar. 1992.
Siemens News Letter, Nov. 1992.
Jager, "Microprocessor Based Disconnect Monitor in Surgery", The UBC Engineer, pp. 28-31, 1982.
MacIntyre, "Clinically Available New Strategies for Mechanical Ventilatory Support", Chest/104/2 (Duke University Medical Center, Durham, NC), pp. 560-565, 1993.
Pocket Guide for Siemens System Servo Ventilator, Nov. 1993.
Search Report Corresponding International Appln. No. PCT/FR95/01158, Nov. 23, 1995.
Preliminary Examination Report for Corresponding International Appln. No. PCT/Fr95/01158, Oct. 22, 1996.
Notification of Opposition to Corresponding European Appln. Ser. No. 95/930565.70782462, Apr. 13, 2000.
The Future Begins . . . with Puritan-Bennett's 7200 Microprocessor Ventilator, May 1983.
Puritan-Bennett, 7200 Microprocessor Ventilator Service Manual, Figure 2-1 Electro-Pneumatic System, Jun. 1983.
Puritan-Bennett, 7200 Microprocessor Ventilator Operator's Manual, Mar. 1986.
Puritan-Bennett Brochure, Flow-By, Option 50, pp. 1-6, Oct. 1986.
French Search Report for Relating French Application No. 9211131, Jun. 29, 1993.
Search Report Corresponding to French (priority Appln. Ser. No. FR9410839, Jun. 2, 1995.
A First Opposition Brief Against the Relating European Patent 0 662 009 B1, Feb. 15, 1999.
Response to Opposition Relating to European Patent 0 662 009 B1, Oct. 8, 1999.
A Second Opposition Brief Against the Relating European Patent 0 662 009 B1, Jan. 19, 2000.
Response to Second Notice of Opposition Relating to European Patent 0 662 009 B1, Apr. 21, 2000.
European Patent Office's Decision on the Opposition Corresponding to European Patent 0 662 009, Sep. 27, 2001.
Non-Final Office Action, U.S. Appl. No. 09/307,511, filed May 7, 1999, 6 pages, Mailed Jun. 6, 2001.
Response to Office Action dated Jun. 6, 2001, in U.S. Appl. No. 09/307,511, filed May 7, 1999, 5 pages, filed Sep. 6, 2001.
Non-Final Office Action, U.S. Appl. No. 09/307,511, filed May 7, 1999, 9 pages, Mailed Nov. 29, 2001.
Response to Non-Final Office Action dated Nov. 29, 2001, in U.S. Appl. No. 09/307,511, filed May 7, 1999, 4 pages, filed Feb. 28, 2002.
Non-Final Office Action, U.S. Appl. No. 09/307,511, filed May 7, 1999, 10 pages, Mailed Jul. 2, 2002.
Opposition Filed by SIEMENS Corresponding to European Appln. Ser. No. 95/930565.7, Feb. 22, 2000.
Grounds of Decision of Revocation Corresponding to European Appln. Ser. No. 95/930565.7 (with English translation), Oct. 16, 2001.
Response to Non-Final Office Action dated Jul. 2, 2002, in U.S. Appl. No. 09/307,511, filed May 7, 1999, 10 pages, filed Oct. 2, 2002.
Final Office Action, U.S. Appl. No. 09/307,511, filed May 7, 1999, 12 pages, Mailed Dec. 31, 2002.
Response to Final Office Action dated Dec. 31, 2002, filed concurrently with Request for Continued Examination for U.S. Appl. No. 09/307,511, filed May 7, 1999, 6 pages, filed Apr. 30, 2000.
Non-Final Office Action, U.S. Appl. No. 09/307,511, filed May 7, 1999, 11 pages, Mailed Jul. 3, 2003.
Response to Non-Final Office Action dated Jul. 3, 2003, in U.S. Appl. No. 09/307,511, filed May 7, 1999, 13 pages, filed Oct. 3, 2003.
Final Office Action, U.S. Appl. No. 09/307,511, filed May 7, 1999, 12 pages, Mailed Dec. 23, 2003.
Response to Final Office Action dated Dec. 23, 2003, in U.S. Appl. No. 09/307,511, filed May 7, 1999, 10 pages, filed Feb. 23, 2004.
Notice of Appeal to the Board of Patent Appeals and Interferences, U.S. Appl. No. 09/307,511, filed May 7, 1999, 2 pages, filed Mar. 23, 2004.
Non-Final Office Action, U.S. Appl. No. 09/307,511, filed May 7, 1999, 12 pages, Mailed Apr. 28, 2004.
U.S. Appl. No. 12/140,095, filed Jun. 16, 2008.
U.S. Appl. No. 11/781,013, filed Jul. 20, 2007.
Response to Non-Final Office Action dated Apr. 28, 2004, in U.S. Appl. No. 09/307,511, filed May 7, 1999, 11 pages, filed Jul. 28, 2004.
U.S. Appl. No. 11/469,677, filed Sep. 1, 2006.
U.S. Appl. No. 12/238,607, filed Sep. 26, 2008.
7200 Series Ventilator, Options, and Accessories: Operator's Manual, Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual, Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Hari, "Flow Sensor Fault Causing Ventilator Malfunction", ANAESTHESIA, 2005, 60, pp. 1042-2052; http://onlinelibrary.wiley.com/doi/10.1111/j.1365-2044.2005.04396.x/pdf; Accessed Jan. 16, 2015).
PCT International Search Report and Written Opinion in International Application PCT/US2009/055280, mailed Mar. 24, 2010, 18 pgs.

BREATHING ASSISTANCE SYSTEM WITH MULTIPLE PRESSURE SENSORS

CROSS-REFERENCE TO RELATED APPLICATIONS

This application is a continuation of U.S. patent application Ser. No. 12/241,243, filed Sep. 30, 2008, now issued U.S. Pat. No. 8,302,602, the contents of which application is hereby incorporated in its entirety by reference.

TECHNICAL FIELD

The present disclosure is related to breathing assistance systems, and more particularly to a breathing assistance system with multiple pressure sensors.

BACKGROUND

Breathing assistance systems are used to provide various types of breathing assistance to patients. For example, a ventilator provides mechanical ventilation to a patient by delivering pressurized gas (e.g., air and/or supplemental oxygen) to the patient through a breathing circuit connected to the patient by a connection device, e.g., an endrotracheal tube or a nose or face mask. A ventilator may provide ventilation according to any of a variety of well-known ventilation modes, e.g., assist/control (A/C) ventilation, volume controlled ventilation, pressure controlled ventilation, and synchronous intermittent mandatory ventilation (SIMV) ventilation. Each of such modes may provide or allow for one or more types of breaths, including mandatory breaths, assisted breaths, and/or spontaneous breaths.

Another example breathing assistance system is a continuous positive airway pressure (CPAP) system. CPAP therapy has become a common prescription for individuals suffering from sleep apnea and/or other breathing ailments. Such therapy may involve placement of a nose or face mask on the subject during sleeping, while positive pressure air is continuously delivered from a CPAP box to the patient through a breathing circuit connected to the patient by a connection device, e.g., a nose or face mask. In this manner, positive pressure air may be delivered to the patient's upper airway in order to prevent the upper airway tissues from collapsing during sleep, thus reducing the occurrence and/or severity of sleep apnea.

SUMMARY

According to one embodiment of the present disclosure, a method for managing pressure in a breathing assistance system configured to provide breathing assistance to a patient via a patient connection system is provided. The method may include receiving one or more first pressure sensor signals from a first pressure sensor, and analyzing the one or more first pressure sensor signals. Based at least on the analysis of the one or more first pressure sensor signals, either the first pressure sensor or the second pressure sensor may be selected for use in controlling the breathing assistance provided to the patient, and the breathing assistance provided to the patient may be controlled based at least on signals from the selected pressure sensor.

According to another embodiment of the present disclosure, a breathing assistance system configured to provide breathing assistance to a patient via a patient connection system is provided. The breathing assistance system includes a first pressure sensor, a second pressure sensor, and a control system. The control system may be configured to receive first pressure sensor signals from the first pressure sensor and second pressure sensor signals from the second pressure sensor; analyze one or more first pressure sensor signals; based at least on the analysis of the one or more first pressure sensor signals, select either the first pressure sensor or the second pressure sensor for use in controlling the breathing assistance provided to the patient; and control the breathing assistance provided to the patient based at least on signals from the selected pressure sensor.

According to another embodiment of the present disclosure, a method is provided for managing pressure in a breathing assistance system including a gas delivery system for delivering gas toward a patient via a patient connection system between the gas delivery system and the patient. The method may include receiving first pressure sensor signals from a first pressure sensor configured to measure gas pressure at a first location relative to the patient connection system; receiving second pressure sensor signals from a second pressure sensor configured to measure gas pressure at a different, second location relative to the patient connection system; controlling the gas de system based on at least one of the first pressure sensor signals and the second pressure sensor signals; automatically detecting an over-pressure condition in the patient connection system based on one or more first pressure sensor signals and one or more second pressure sensor signals; and in response to detecting the over-pressure condition in the patient connection system, automatically controlling the gas delivery system to reduce the pressure in the patient connection system.

According to another embodiment of the present disclosure, a breathing assistance system for providing breathing assistance to a patient is provided. The breathing assistance system may include a gas delivery system for delivering gas toward a patient via a patient connection system between the gas delivery system and the patient; a first pressure sensor configured to measure gas pressure at a first location relative to the patient connection system; a second pressure sensor configured to measure gas pressure at a different, second location relative to the patient connection system; and a control system. The control system may be configured to: receive first pressure sensor signals from the first pressure sensor; receive second pressure sensor signals from the second pressure sensor; control the gas delivery system based on at least one of the first pressure sensor signals and the second pressure sensor signals; automatically detect an over-pressure condition in the patient connection system based on one or more first pressure sensor signals and one or more second pressure sensor signals; and in response to detecting the over-pressure condition in the patient connection system, automatically control the gas delivery system to reduce the pressure in the patient connection system.

BRIEF DESCRIPTION OF THE DRAWINGS

Some embodiments of the disclosure may be understood by referring, in part, to the following description and the accompanying drawings, in which like reference numbers refer to the same or like parts and wherein.

DETAILED DESCRIPTION

Selected embodiments of the disclosure may be understood by reference, in part, to FIGS. 1-13B, wherein like numbers refer to same and like parts.

Figure 1:
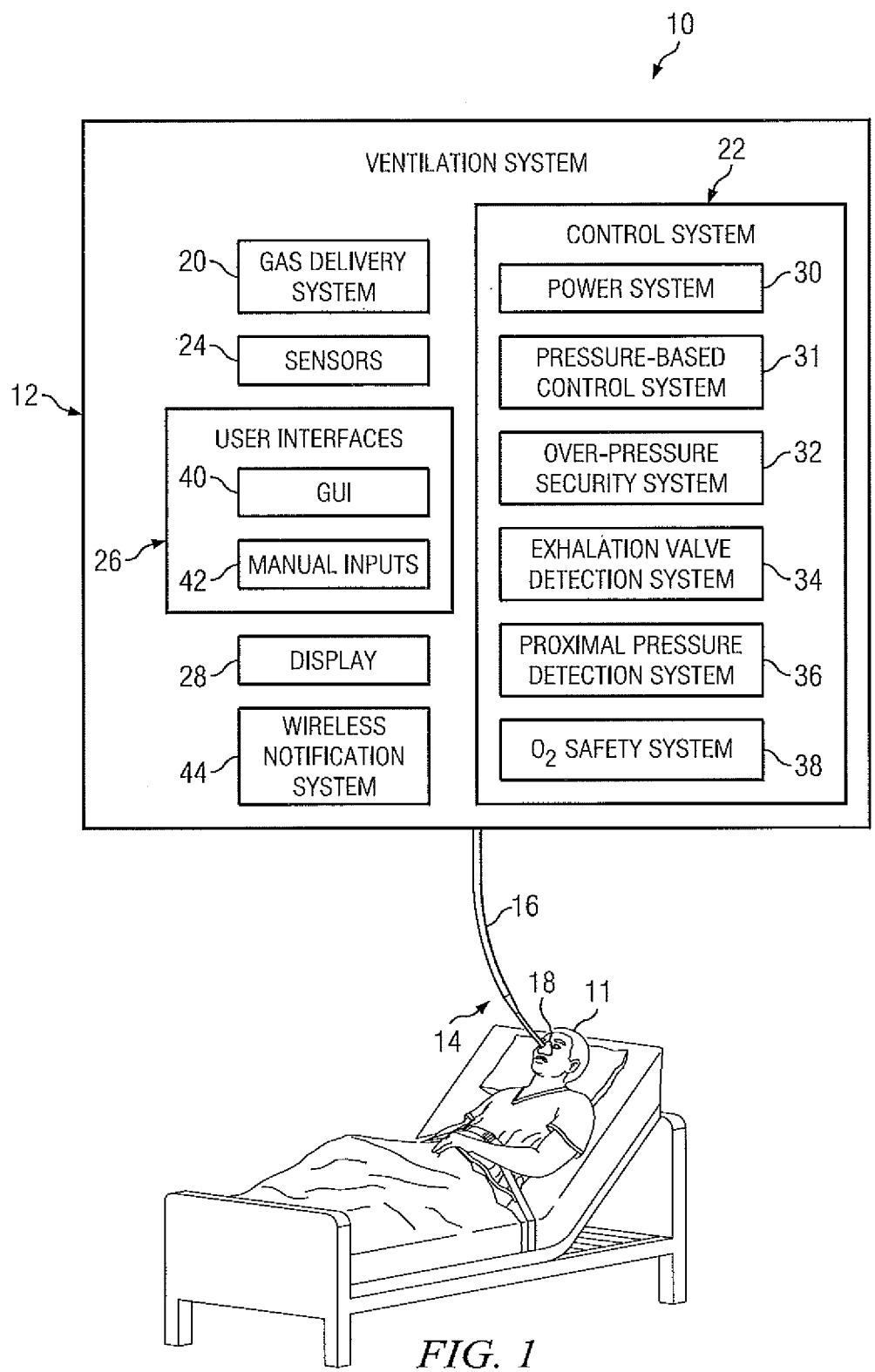
FIG. 1 illustrates an example breathing assistance system for providing breathing assistance to a patient, according to one embodiment of the disclosure.

FIG. 1 illustrates an example breathing assistance system 10 for providing breathing assistance to a patient, according to one embodiment of the disclosure. Breathing assistance system 10 may be generally configured to provide one or more types of ventilation to the patient. As used herein, "ventilation" means communicating gas to and/or from a patient 11 to provide any type of breathing assistance to the patient 11, including, e.g., mechanically ventilating the patient and/or treating an apnea or other breathing condition of the patient. "Ventilation" includes breathing assistance typically provided by a ventilator, as well as breathing assistance typically provided by CPAP device. Thus, as discussed below, breathing assistance system 10 may provide any or all of the following:

Positive Pressure ventilation;
Assist/Control, SIMV, and/or CPAP modes of ventilation;
Breath types including Volume, Pressure Control, and Pressure Support;
Other types or modes of ventilation and/or other breath types.

In example embodiments, breathing assistance system 10 may provide some or all of the following user-selectable ventilation modes:
Assisted Controlled Volume (VOLUME A/C);
Assisted Controlled Pressure (PRESSURE A/C);
Synchronous Intermittent Mandatory Ventilation Volume (V SIMV);
Synchronous Intermittent Mandatory Ventilation Pressure (P SIMV);
Continuous Positive Airway Pressure (CPAP); and
Pressure Support Ventilation (PSV).

Breathing assistance system 10 may be configured for use by both adult and pediatric patients 11. In addition, in certain embodiments, breathing assistance system 10 may be configured for use in institutional, home, and/or portable settings.

As shown in FIG. 1, breathing assistance system 10 may include a ventilation system 12 and a connection system 14 for connecting ventilation system 12 to patient 11.

Ventilation system 12 may comprise any device, apparatus, or system for providing ventilation to a patient 11 via connection system 14. Connection system 14 may be generally configured to deliver gas from ventilation system 12 to patient 11 and/or to communicate exhaust gas away from patient 11. For example, connection system 14 may comprise any suitable type of breathing circuit 16 (e.g., a single-limb or dual-limb breathing circuit) and/or a patient connection apparatus 18. For instance, connection system 14 may include a 6-foot (single-limb or dual-limb) breathing circuit 16. In embodiments using a dual-limb breathing circuit 16, both limbs (the inspiratory limb and the expiratory limb) may be connected to ventilation system 12, as discussed below with reference to FIG. 2.

A patient connection apparatus 18 may include any device or devices configured to connect breathing circuit 16 to one or more breathing passageways of patient 11. For example, patient connection apparatus 18 may include a patient connection tube directly connected to the patient's trachea, an artificial airway (e.g., an endotracheal tube or other device) inserted in the patient's trachea, and/or a mask, cushion or nasal pillows positioned over the patient's nose and/or mouth.

Ventilation system 12 may include a gas delivery system 20, a control system 22, sensors 24, user interfaces 26, a display system 28, and a wireless notification module 44.

Gas delivery system 20 may include any device or devices configured to generate, supply, and/or deliver gas (e.g., pressurized air) toward patient 11 via connection system 14. For example, gas delivery system 20 may comprise a device capable of generating pressurized air (e.g., a motorized turbine-based blower or piston-based device), a wall outlet through which pressurized air may be supplied (e.g., in a hospital or clinic), valves configured to control the supply of gas to the patient (e.g., a PSOL or other solenoid valve), one or more tanks of compressed gas, a compressor, or any other suitable source of pressurized or non-pressurized gas. In some embodiments, gas delivery system 20, in cooperation with other components of ventilation system 12 (e.g., an exhalation valve) may generate both positive and negative gas flows toward patient 11. For example, a positive gas flow may be generated as gas is delivered to patient 11 during inhalation, while a negative gas flow may be generated as exhaust gas is communicated from patient 11 during exhalation.

In some embodiments, gas delivery system 20 may be configured to deliver a gas mixture toward patient 11, e.g., a mixture of air and supplemental oxygen or other supplemental gas. Depending on the particular embodiment, the point of mixture for the multiple gasses may be upstream or downstream of gas delivery system 20. For example, a supplemental oxygen stream may be connected to mix with a primary air stream at a point upstream or downstream of gas delivery system 20.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Control system 22 may include any sub-systems for controlling any aspect of the operation of ventilation system 12, including, e.g., a power system 30, a gas delivery control system 31, an over-pressure security system 32, an exhalation valve detection system 34, a proximal pressure detection system 36, and an oxygen safety system 38.

Each sub-system 30, 31, 32, 34, 36, and 38 of control system 22, may include, or have access to, any suitable controllers, processors, memory devices, and any other suitable hardware, software, and/or firmware for performing any of the function associated with such systems. In particular, each system 30, 31, 32, 34, 36, and 38 may include or have access to any instructions (e.g., software, firmware, algorithms, or other logic or instructions) stored in any suitable tangible storage media and executable by a processor for performing any of the functions associated with that system.

Any one or more sensors 24 may be provided for sensing, detecting, and/or monitoring one or more parameters related to the ventilation of patient 11, e.g., parameters regarding the ventilation provided by ventilation system 12 and/or physiological parameters regarding patient 11. For example, sensors 24 may include one or more devices for measuring various parameters of gas flowing to or from patient 11 or ventilation system 12, e.g., the pressure, flow rate, flow volume, temperature, gas content, and/or humidity of such gas flow.

In certain embodiments, sensors 24 may include one or more pressure sensors and one or more flow sensors for measuring the pressure and flow, respectively, of gas through various components of system 10. Such pressure and flow sensors 24 may be located at any suitable location in system 10. For example, each sensor 24 may be integrated with or coupled to ventilation system 12, integrated with or coupled to connection system 14, coupled to patient 11, or otherwise associated with system 10.

Figure 5:
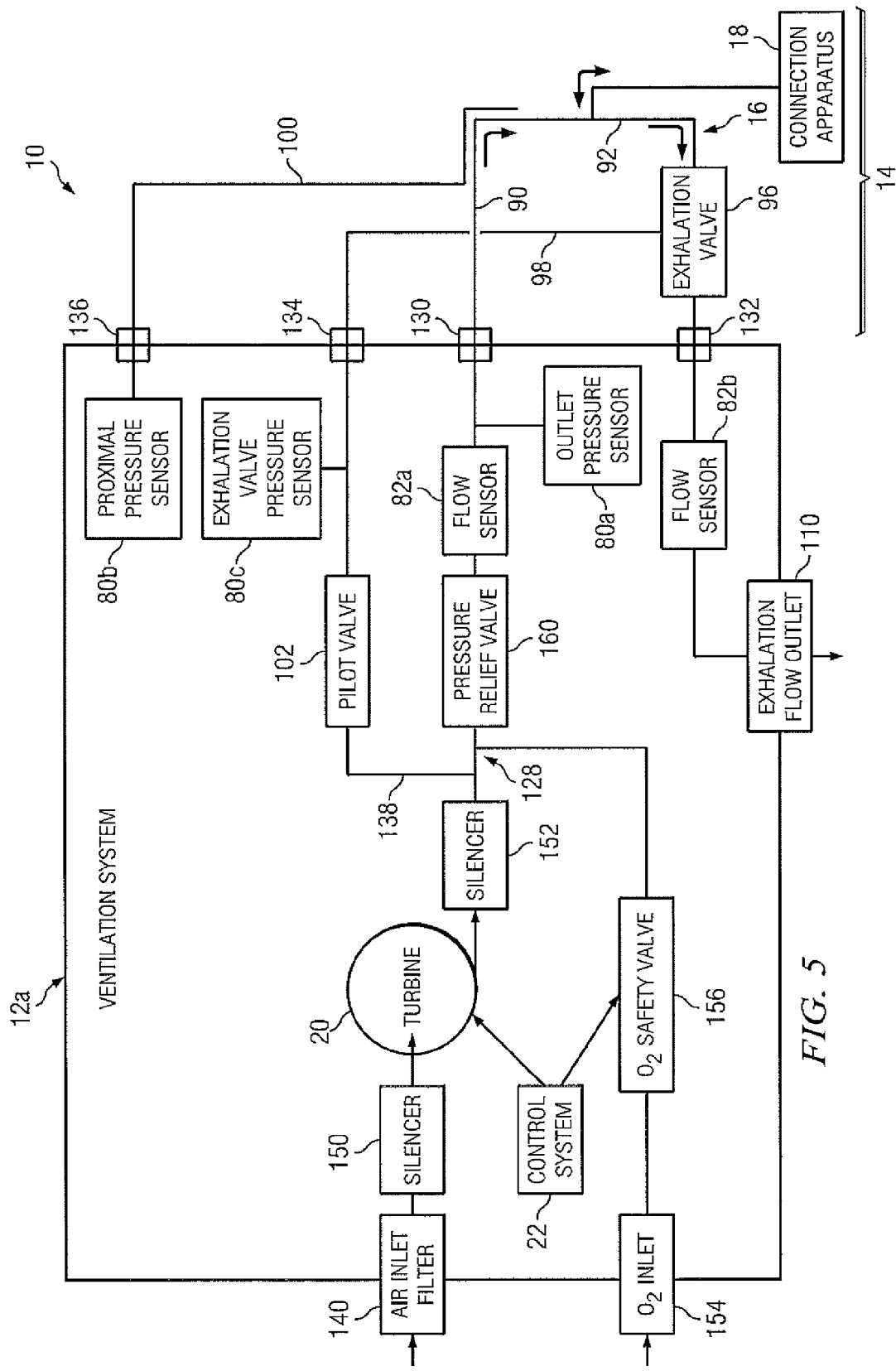
FIG. 5 illustrates a flow path diagram showing various components and gas flow paths in an example embodiment of a ventilation system, according to one embodiment of the present disclosure.
Figure 6:
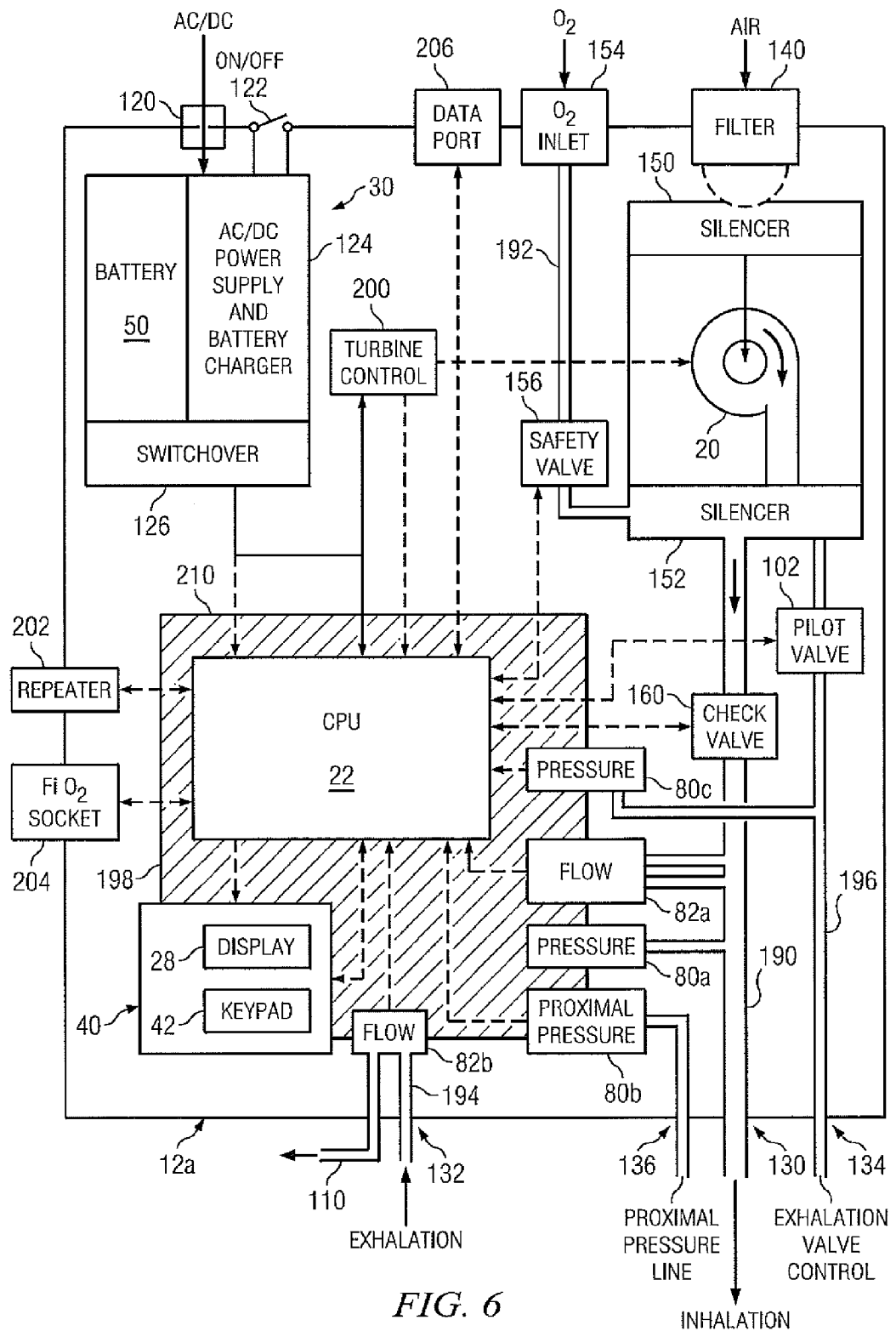
FIG. 6 illustrates an example arrangement of various components of an example ventilation system, according to one embodiment of the present disclosure.

In some embodiments (e.g., as shown in FIGS. 5 and 6), system 10 may include any or all of the following:

(a) a main pressure sensor for measuring the pressure of gas flow exiting ventilation system 12 or gas delivery system 20, or the pressure of gas flow entering connection system 14;

(b) a proximal pressure sensor for measuring pressure at or near the patient end of connection system 14, referred to as the "proximal pressure";

(c) an exhalation valve pressure sensor for measuring pressure in a conduit used for controlling an exhalation valve of system 10;

(d) an inhalation flow sensor for measuring the flow rate of gas flowing toward patient 11 (e.g., via an inhalation limb of breathing circuit 16);

(e) an exhalation flow sensor for measuring the flow rate of gas exhaled by patient 11 (e.g., via an exhalation limb of breathing circuit 16); and/or (f) any other pressure and/or flow sensors.

The main pressure sensor, proximal pressure sensor, and/or exhalation valve pressure sensor may be used to provide various functions of ventilation system 12. For example, as discussed below regarding FIG. 2, signals from the main pressure sensor and the proximal pressure sensor may be used in a first technique for detecting and managing over-pressure of gas in connection system 14 (e.g., in breathing circuit 16). As another example, as discussed below regarding FIG. 2, signals from the exhalation valve pressure sensor may be used in a second technique for detecting and managing over-pressure of gas in connection system 14 (e.g., in breathing circuit 16). As another example, as discussed below regarding FIG. 2, signals from the exhalation valve pressure sensor may be used to detect whether an exhalation valve is present in the current configuration of system 10 (e.g., whether the currently connected breathing circuit 16 includes an exhalation valve). As yet another example, as discussed below regarding FIG. 2, signals from the main pressure sensor and/or the proximal pressure sensor may be used to determine whether proximal pressure may be measured and used by ventilation system 12 (e.g., if a proximal pressure line is properly connected and the proximal pressure sensor is working properly).

User interfaces 26 may include any suitable device or devices allowing a user to interface with breathing assistance system 10, e.g., to control ventilation system 12, to navigate through various display screens, to make selections, and/or to set, modify, or otherwise control various parameters regarding system 10. For example, user interfaces 26 may allow a user to input desired performance parameters (e.g., pressure or flow rate) that may be communicated to control system 22 to control the operation of gas delivery system 20 and/or other components of system 10.

User interfaces 26 may include a graphic user interface (GUI) 40, one or more manual input devices 42 separate from the GM, and/or any other input devices. In some embodiments, GUI 40 may include a touch screen configured to display various information and provide an interface for accepting input from user (e.g., to navigate through various screens, to make selections, to set or modify various parameters, to change or configure the display, etc.). In embodiments in which GUI 40 does not include a touch screen, manual input devices 42 may be used to make selections and navigate through various screens or menus displayed on GUI 40. Manual input devices 42 may include any physical buttons, knobs, dials, switches, levers, or any other devices that may be manipulated by a user.

Display system 28 may comprise a screen or any other device suitable for visually displaying medical data. For example, display system 28 may include a monitor, an LCD screen, LEDs, or any other visual device. In some embodiments, display system 28 and user interfaces 26 may be at least partially integrated, e.g., where ventilation system 12 includes a touch screen or other GUI 40.

Power system 30 may include or facilitate the connection of one or more sources of power for ventilation system 12, e.g., an external AC power source, an external DC power source, and/or one or more rechargeable batteries, for example. In embodiments including a battery 50, power system 30 may include a battery security system 52 for ensuring that only approved batteries may be used in ventilation system 12 and/or a battery age management system 70 for recording and displaying age data regarding a battery 50, e.g., the number of charge and discharge cycles the battery 50 has experienced. Battery security system 52 and battery age management system 70 are illustrated and discussed in greater detail below with reference to FIG. 3.

Gas delivery control system 31 is generally operable to control the delivery of gas to and/or from patient 11 based on various input, e.g., input received from a user (e.g., via a touch screen and/or other user interfaces provided by ventilation system 12), data received from one or more sensors 24, and/or data received from other components of ventilation system 12 (e.g., power system 30, over-pressure security system 32, exhalation valve detection system 34, and proximal pressure detection system 36). As discussed below, in some embodiments, gas delivery control system 31 may control gas delivery to patient 11 based on input from one of two sensors 24: (a) a proximal pressure sensor generally configured to measure pressure in the breathing circuit 16 near patient 11, and (b) an outlet pressure sensor generally configured to measure pressure exiting ventilation system 12 and entering breathing circuit 16.

Over-pressure security system 32 is generally operable to detect and facilitate the management of over-pressure of gas in connection system 14 (e.g., in breathing circuit 16) based on pressure signals received from one or more pressure sensors 24.

Exhalation valve detection system 34 is generally operable to determine whether an exhalation valve is present in the current configuration of system 10 (e.g., whether the currently connected breathing circuit 16 includes an exhalation valve) based on pressure signals received from one or more pressure sensors 24.

Proximal pressure detection system 36 is generally operable to determine whether proximal pressure may be measured and used by ventilation system 12 (e.g., if a proximal pressure line is properly connected and the proximal pressure sensor is working properly) based on pressure signals received from one or more pressure sensors 24.

Over-pressure security system 32, exhalation valve detection system 34, and proximal pressure detection system 36, are discussed in greater detail below with reference to FIG. 2.

Oxygen safety system 38 is generally operable to slow or stop the flow of a supplemental oxygen supply in particular circumstances, e.g., when gas delivery system 20 is not running and/or overheating. Oxygen safety system 38 is discussed in greater detail below with reference to FIGS. 4A and 4B.

Wireless notification module 44 is generally configured to communicate wireless notifications (e.g., alarms generated by control system 22) from ventilation system 12 to any suitable receiving device, e.g., a remote monitor or a mobile alarm unit carried by a user (e.g., a caretaker). In some embodiments, wireless notification module 44 may communicate to such receiving device(s) via one or more wireless repeaters, which may increase the physical range of wireless communications from ventilation system 12.

Sensor Systems

Figure 2:
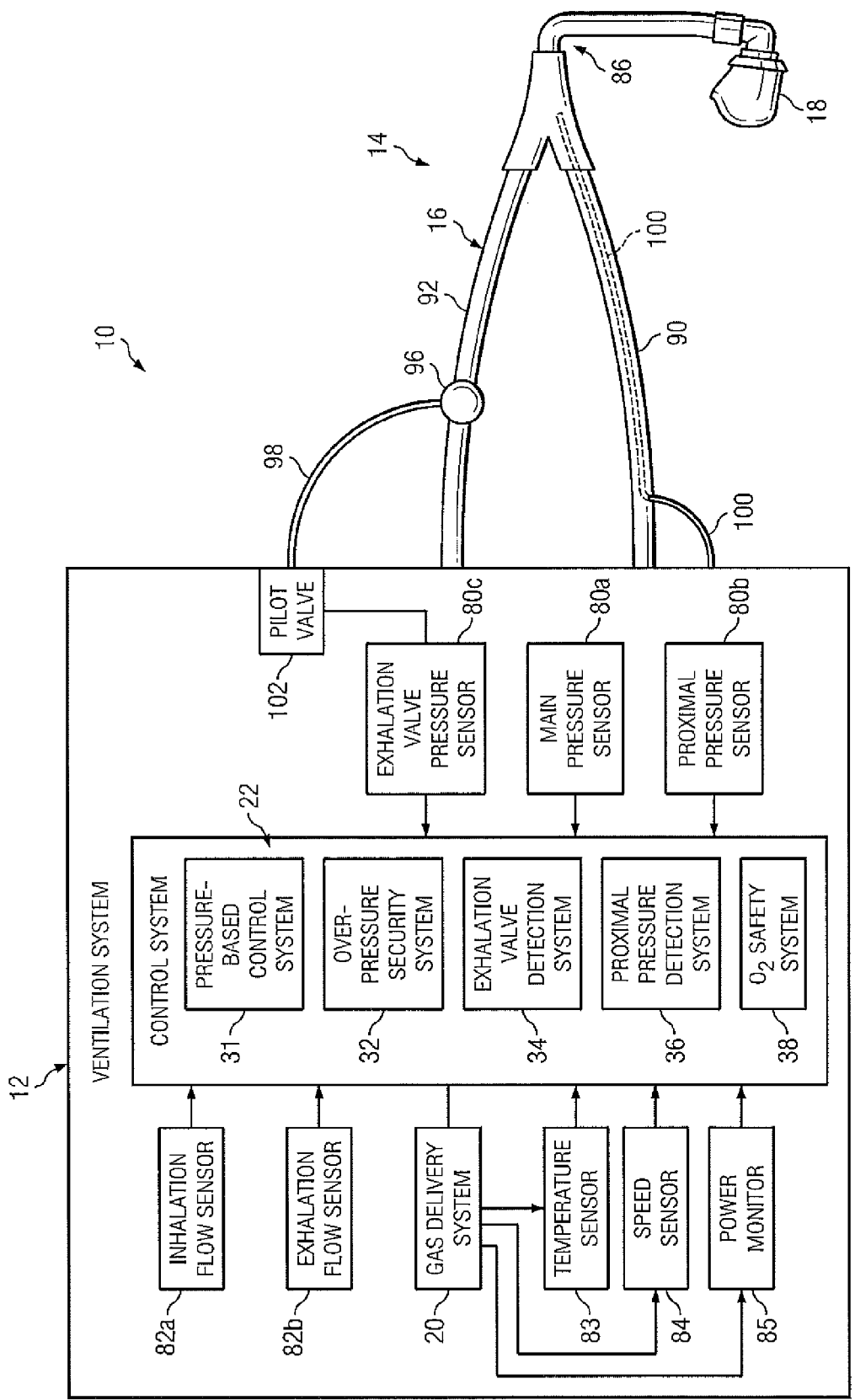
FIG. 2 illustrates an example ventilation system including an over-pressure security system, exhalation valve detection system, proximal pressure detection system, and an O2 safety system, according to certain embodiments of the present disclosure.

FIG. 2 illustrates an example ventilation system 12 including an over-pressure security system 32, exhalation valve detection system 34, proximal pressure detection system 36, and an O2 safety system 38, according to certain embodiments of the present disclosure. FIG. 2 illustrates systems 31, 32, 34, 36, and 38, various sensors 24 for providing input to systems 31, 32, 34, 36, and 38, and/or control system 22, and an example connection system 14 connected to ventilation system 12. The example connection system 14 includes a dual-limb breathing circuit 16 including an inspiratory limb 90, exhalation limb 92, exhalation valve 96, exhalation valve control line 98, and a proximal pressure line 100 running along a length of inspiratory limb 90 or exhalation limb 92.

Breathing assistance system 10 may include one or more pressure sensors 80 for providing input to systems 31, 32, 34, and 36. For example, system 10 may include any or all of the following pressure sensors:

(a) An outlet pressure sensor 80a located at or near a main gas outlet of ventilation system 12 (e.g., at or near an outlet of gas delivery system 20) to measure the pressure of gas flow exiting ventilation system 12 or gas delivery system 20, or the pressure of gas flow entering connection system 14. For example, outlet pressure sensor 80a may be located inside or just outside a housing or enclosure of ventilation system 12.

(b) A proximal pressure sensor 80b configured to measure pressure at or near the patient end of connection system 14 (indicated in FIG. 2 generally at 86), referred to as the "proximal pressure." Proximal pressure sensor 80b may be located at any suitable location. For example, proximal pressure sensor 80b may be located in ventilation system 12 and connected to a proximal pressure line 100 (e.g., a tube or other conduit) that extends along a limb 90 or 92 of breathing circuit 16 and opens near the patient end 86 of connection system 14. Thus, proximal pressure sensor 80b may measure the gas pressure at the open end (i.e., the patient end) of proximal pressure line 100. As another example, proximal pressure sensor 80b may be located at or near the open, patient end of the proximal pressure line 100 and may be configured to communicate pressure measurement signals back to ventilation system 12 (e.g., via an embedded wire in connection system 14).

Typically, the pressure measured by proximal pressure sensor 80b is lower than the pressure measured by outlet pressure sensor 80a in positive flow situations (flow toward patient 11), and greater than the pressure measured by outlet pressure sensor 80a in negative flow situations (flow away patient 11). The difference between the measurements of sensors 80a and 80b is largely or completely due to pressure drop inherent in the breathing circuit 16. Proximal pressure sensor 80b typically provides a more accurate measure of the pressure experienced by the patient, referred to as the "patient pressure."

(c) An exhalation valve pressure sensor 80c configured to measure pressure in a conduit used for controlling an exhalation valve of system 10. In some embodiments, breathing circuit 16 may include an exhalation valve 96 and an exhalation valve control line 98. Gas may be delivered from gas delivery system 20 through exhalation valve control line 98 to control exhalation valve 96. Measurements taken by exhalation valve pressure sensor 80c may be used (e.g., by control system 22) for controlling exhalation valve 96.

For example, in some embodiments, a pilot valve 102 (e.g., controlled by control system 22) may control the pressure in exhalation valve control line 98, thus controlling the operation of exhalation valve 96. Exhalation valve pressure sensor 80c may be configured to measure the pressure in exhalation valve control line 98 between the pilot valve 102 and exhalation valve 96, which measured pressure may then be used (e.g., by control system 22) for controlling the pilot valve 102 in order to control exhalation valve 96. Exhalation valve pressure sensor 80c may be located at any suitable location, e.g., within or attached to ventilation system 12 (e.g., near the pilot valve 102) or breathing circuit 16 (e.g., near exhalation valve 96).

Pilot valve 102 may comprise any type of valve operable to control gas flow through exhalation valve control line 98 in order to control exhalation valve 96. For example, pilot valve 102 may comprise a solenoid valve, a pneumatic valve, or a piezoelectric valve. In an example embodiment, pilot valve 102 is an electro valve and exhalation valve pressure sensor 80c is connected to a command port of the electro valve. In other embodiments, ventilation system 12 may not include a pilot valve.

In operation, any or all of main pressure sensor 80a, proximal pressure sensor 80b, and exhalation valve pressure sensor 80c may take and communicate pressure measurements for use by sub-systems 31, 32, 34, and/or 36 of control system 22. For example, pressure measurements taken by any or all of sensors 80a, 80b, and 80c may be communicated to control system 22 and used by the various sub-systems 31, 32, 34, and/or 36 for controlling various aspects of the operation of system 12, e.g., the delivery of gas by gas delivery system 20. Sensors 80a, 80b, and/or 80c may take and/or communicate pressure measurements according to any time schedule, e.g., periodically or substantially continuously, for example.

In addition to pressure sensors 80, breathing assistance system 10 may also include one or more flow sensors 82 for measuring gas flows and providing input to control system 22. For example, system 10 may include at least (a) an inhalation flow sensor 82a configured to measure the flow rate of gas flow delivered toward patient 11 via connection system 14, and (b) an exhalation flow sensor 82b configured to measure the flow rate of gas flow exhaled by or otherwise communicated away from patient 11 via connection system 14.

Like pressure sensors 80, each flow sensor 82 may be located at any suitable location. For example, inhalation flow sensor 82a may be located at or near a gas outlet of ventilation system 12 connected to inhalation limb 90 of breathing circuit 16, and exhalation flow sensor 82b may be located at or near a gas inlet of ventilation system 12 connected to exhalation limb 90 of breathing circuit 16.

It should be understood that ventilation system 12 includes various other components (e.g., a power system, user interfaces, a display, etc.) not shown in FIG. 2 for the sake of simplicity.

Gas Delivery Control System 31

As discussed above, gas delivery control system 31 may control the delivery of gas to and/or from patient 11 based on various input, e.g., input received from a user (e.g., via a touch screen and/or other user interfaces provided by ventilation system 12), data received from one or more sensors 24, and/or data received from other components or sub-systems of ventilation system 12. Gas delivery control system 31 may control the communication of gas to and/or from patient 11 by controlling, for example, the operation of gas delivery system 20 and/or the operation of one or more valves in order to control the pressure and/or flow rate of gas delivered to and/or communicated from patient 11.

For example, gas delivery control system 31 may regulate the pressure and/or flow rate of gas communicated to and/or from patient 11 based on pressure and/or flow data received from pressure and/or flow sensors 24. As another example, gas delivery control system 31 may shut down or reduce the pressure and/or flow rate of gas delivered to patient 11 based on signals received from over-pressure security system 32 indicating an over-pressure situation. As another example, gas delivery control system 31 may control the pressure and/or flow rate of gas communicated to and/or from patient 11 based on signals received from exhalation valve detection system 34 indicating whether or not an exhalation valve is being used in the current system configuration. As another example, gas delivery control system 31 may control the pressure and/or flow rate of gas communicated to and/or from patient 11 based on signals received from proximal pressure detection system 36 indicating whether or not a proximal pressure sensor is currently connected and operational. Example implementations of each of these techniques for controlling system 10 are discussed below.

Gas delivery control system 31 may include or have access to any instructions (e.g., any suitable software, algorithms, or other logic or instructions that may be executed by one or more processors) for automatically controlling the operation of ventilation system 12 (e.g., controlling the pressure and/or flow rate output by gas delivery system 20 and/or controlling one or more valves) based on any of the various input data discussed herein.

Gas delivery control system 31 may control gas delivery system 20 directly, or by controlling another system or device configured to control gas delivery system 20. For example, in embodiments including a turbine-based blower 20, gas delivery control system 31 may control a turbine control device 200 (e.g., see FIG. 6), which in turn controls the turbine.

In some embodiments, gas delivery control system 31 may control gas delivery to patient 11 based on input from (a) outlet pressure sensor 80a (for measuring the pressure of gas exiting ventilation system 12 or entering connection system 14) and/or (b) proximal pressure sensor 80b (for measuring the pressure of gas in connection system 14 near patient 11). For example, as discussed below in the "Dual-Sensor System and Proximal Pressure Detection" section, system 12 may default to using proximal pressure sensor 80b for controlling ventilation, but switch to outlet pressure sensor 80a as a backup when proximal pressure line 100 is not connected to system 12 or the proximal pressure cannot effectively be used for some other reason.

As another example, gas delivery control system 31 may use readings from both outlet pressure sensor 80a and proximal pressure sensor 80b for controlling ventilation. For example, control system 31 may calculate an average, or weighted average, of readings from sensor 80a and sensor 80b to determine effective pressure values for use in controlling ventilation. As another example, control system 31 may calculate effective pressure values using any other algorithm(s) incorporating readings from both sensors 80a and 80b. One example algorithm provides:

$$P_E = A^*(P_{proximal}) + B^*(P_{outlet}) \tag{1}$$

where:

$P_E$ = the effective pressure that may be used for controlling ventilation;

$P_{proximal}$ = pressure measured by proximal pressure sensor 80b;

$P_{outlet}$ = pressure measured by outlet pressure sensor 80a; and

A and B are coefficients (e.g., positive values having a sum of 1.0).

Another example algorithm provides:

$$P_E = A*(P_{proximal}) + B*(P_{outlet} + P_{drop}) \quad (2)$$

where $P_{drop}$ = a pressure drop compensation value. $P_{drop}$ may be an estimate of the pressure drop inherent in connection system 14 between outlet pressure sensor 80a and patient 11, which pressure drop may be a function of the flow rate through connection system 14. $P_{drop}$ may be determined in any known or suitable manner, e.g., using techniques described in co-pending EP Patent Application EP 08006240.9, filed on Mar. 31, 2008, and entitled "Systems and Methods for Compensating for Pressure Drop in a Breathing Assistance System."

Dual-Sensor System and Proximal Pressure Detection

As discussed above, proximal pressure detection system 36 may be generally operable to determine whether proximal pressure may be effectively used by ventilation system 12 (e.g., if a proximal pressure line 100 is properly connected and the proximal pressure sensor 80b is providing useful readings) based on pressure signals received from one or more pressure sensors 24.

Gas delivery control system 31 may control the pressure and/or flow of gas delivered toward patient 11 based on one or both of (a) outlet pressure measured by outlet pressure sensor 80a and (b) proximal pressure measured by proximal pressure sensor 80b. As discussed above, proximal pressure measured by proximal pressure sensor 80b typically provides a more accurate measure of the patient pressure than outlet pressure measured by outlet pressure sensor 80a. Thus, it may be desirable to use proximal pressure for controlling the pressure and/or flow of delivered gas, assuming that proximal pressure may be effectively used for controlling ventilation (e.g., if a proximal pressure line 100 is properly connected and the proximal pressure sensor 80b is working properly). If proximal pressure cannot be effectively used for controlling ventilation (e.g., if a proximal pressure line 100 is not connected or is blocked, or if proximal pressure sensor 80b is not working properly), gas delivery control system 31 may use outlet pressure sensor 80a as a backup for measuring pressure for controlling ventilation; however, as such pressure measurements may be less accurate, the ventilation control may be less than optimal in certain ventilation modes or applications.

Therefore, proximal pressure detection system 36 may determine whether proximal pressure may be effectively used, e.g., by gas delivery control system 31 for controlling ventilation pressure and/or flow. Proximal pressure detection system 36 may compare measurements from outlet pressure sensor 80a with measurements from proximal pressure sensor 80b, and determine whether or not proximal pressure can be effectively used based on the results of such comparison. For example, proximal pressure detection system 36 may determine that proximal pressure can be effectively used if the outlet pressure (measured by sensor 80a) is greater than the proximal pressure (measured by sensor 80b), but not if the outlet pressure is less than or equal to the proximal pressure (during positive direction flow, i.e., toward patient 11). As another example, proximal pressure detection system 36 may determine that proximal pressure can be effectively used if the outlet pressure is greater than the proximal pressure, but not by more than a predetermined threshold value. The preceding examples assume positive direction flow (i.e., toward patient 11); for negative direction flow (i.e., away from patient 11), the analysis would be reversed.

As another example, proximal pressure detection system 36 may compare a proximal pressure measurement taken at a particular flow rate to a predetermined expected pressure value for the particular flow rate, and determine that proximal pressure can be effectively used if the measured proximal pressure does not differ from the expected pressure value by more than a predetermined threshold value.

In other embodiments, proximal pressure detection system 36 may separately determine (a) whether a proximal pressure line 100 is not connected to system 12 and (b) whether readings from proximal pressure sensor 80b are effective, or usable, and use both determinations for controlling various aspects of the operation of ventilation system 12.

Based on the results of any of such analyses discussed above, proximal pressure detection system 36 may communicate a notification to gas delivery control system 31 indicating whether proximal pressure cannot be effectively used. If proximal pressure cannot be effectively used, gas delivery control system 31 may subsequently use outlet pressures (measured by sensor 80a) for controlling ventilation, and/or may trigger an alarm or notification to the user that the proximal pressure system is not connected or not working properly. The alarm may comprise any notification that may be sensed by a user, e.g., an audible alarm or a visible alarm displayed to the user, e.g., via display 28 or separate device (e.g., an LED). If proximal pressure can be effectively used, no alarm is triggered (although gas delivery control system 31 may notify the user that proximal pressure is being used) and ventilation may begin, or continue, using proximal pressure to control ventilation pressure and/or flow.

Proximal pressure detection system 36 may determine whether or not proximal pressure can be effectively used at any suitable time. For example, system 36 may perform such analysis prior to, or during, the initiation of ventilation in order to establish the most accurate control system. In addition, system 36 may perform such analysis periodically or substantially continuously during ventilation of patient 11, e.g., such that system 36 may adjust to a disconnection (or connection) of proximal pressure line 100 during ventilation. If gas delivery control system 31 is using proximal pressure to control ventilation, and system 36 determines that proximal pressure can no longer be effectively used (e.g., upon disconnection of proximal pressure line 100 from system 12), system 36 may notify gas delivery control system 31 such that gas delivery control system 31 can switch to using outlet pressure (measured by sensor 80a) and trigger an alarm that the proximal pressure system has been disconnected or is not working properly. Similarly, if gas delivery control system 31 is using outlet pressure to control ventilation, and system 36 determines that proximal pressure can now be effectively used (e.g., upon connection of proximal pressure line 100 to system 12), system 36 may notify gas delivery control system 31 such that gas delivery control system 31 can switch to using proximal pressure (measured by sensor 80b) to control ventilation. Thus, gas delivery control system 31 can automatically switch between using outlet pressure sensor 80a and proximal pressure sensor 80b, depending on whether proximal pressure can currently be used (e.g., depending on whether a pressure line 100 is currently connected).

In addition, in some embodiments, control system 22 may allow or disallow certain ventilation modes or settings based on whether gas delivery control system 31 is currently using outlet pressure or proximal pressure to control ventilation (e.g., based on whether or not a pressure line 100 is currently connected). For example, certain ventilation modes or settings may require accurate patient pressure readings that may be provided by proximal pressure sensor 80b but not by outlet pressure sensor 80a. Thus, control system 22 may disallow user selection of, and/or automatic switching to, such ventilation modes or settings while outlet pressure is being used to control ventilation (e.g., when pressure line 100 is not connected to system 12). An alarm or notification indicating that such ventilation modes or settings are not available due to pressure line 100 not being connected may be displayed to the user, e.g., via display 28. If a pressure line 100 is then connected/re-connected to system 12, control system 22 may allow user selection or switching to such disallowed ventilation modes or settings.

In some embodiments, if proximal pressure line 100 becomes disconnected while operating according to a ventilation mode or settings that requires proximal pressure readings (from sensor 80b), proximal pressure detection system 36 may detect the disconnection and gas delivery control system 31 may automatically adjust the ventilation (e.g., by switching to a different ventilation mode or adjusting one or more settings) to be compliant with operation based on outlet pressure readings (from sensor 80a). Gas delivery control system 31 may also generate an alarm or notification to the user that the proximal pressure line is disconnected and/or that the ventilation mode or settings have been automatically changed. If proximal pressure line 100 is then re-connected while operating according to the changed ventilation mode or settings based on outlet pressure readings, proximal pressure detection system 36 may detect the re-connection and gas delivery control system 31 may automatically switch back to the previous ventilation mode or settings, or may automatically display to the user a selectable option to return to such previous ventilation mode or settings.

Proximal pressure detection system 36 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Proximal pressure detection system 36 may be partially or fully integrated with, or may be distinct from, gas delivery control system 31, Over-Pressure Security As discussed above, over-pressure security system 32 is generally operable to detect and facilitate the management of over-pressure of gas in connection system 14 (e.g., in breathing circuit 16) based on pressure signals received from one or more pressure sensors 24. For example, over-pressure security system 32 may provide either or both of the levels of over-pressure security discussed below.

A first level of ever-pressure security is based on redundancy of pressure measurements from outlet pressure sensor 80a and proximal pressure sensor 80b. As discussed above, outlet pressure sensor 80a may measure pressure at or near a main gas outlet of ventilation system 12 (i.e., the pressure of gas flow entering connection system 14), and proximal pressure sensor 80b may measure "proximal pressure" at or near the open end (i.e., the patient end) of a proximal pressure line 100 extending along a limb of breathing circuit 16. The two sensors 80a and 80b may produce different results due to pressure drop inherent in breathing circuit 16.

The first level of over-pressure security involves monitoring both outlet pressure sensor 80a and proximal pressure sensor 80b to detect an over-pressure condition in connection system 14. For example, over-pressure security system 32 may compare pressure measurements received from sensors 80a and 80b to one or more threshold pressure values to automatically detect an over-pressure condition. Pressure measurements from both sensors 80a and 80b may be compared to a single pressure threshold value, or each sensor's measurements may be compared to a separate corresponding pressure threshold value. Such pressure threshold value(s) may be determined in any suitable manner, and may vary over time.

If some embodiments, the determination of pressure threshold values depends on the selected ventilation mode and/or breath type. For example, in one embodiment:

For Volume modes, the pressure threshold value is set by a user via GUI 40 as a "high pressure" alarm threshold.

For Pressure modes, the pressure threshold value is automatically calculated on the basis of the ventilation pressure set by the user via GUI 40, e.g., according to the equation:

$$\text{Pressure threshold} = P_{control}(\text{or } P_{support}) + X\%$$

where:

$P_{control}$ represents the pressure setting in a Control mode;
$P_{support}$ represents the pressure setting in a Support mode; and X is a preset coefficient, e.g., 10% or 20%.

If over-pressure security system 32 detects an over-pressure condition, system 32 may generate an over-pressure signal to gas delivery control system 31 (and/or to an alarm system) indicating details of the over-pressure condition (e.g., relevant pressure measurement(s) and threshold value(s)). In response, gas delivery control system 31 may control gas delivery system 20 in order to end the over-pressure condition, for example by reducing the pressure or flow rate produced by gas delivery system 20 (e.g., to a pressure at or just below a threshold pressure value, or to a lower pressure) or by shutting down gas delivery system 20. For example, in embodiments in which gas delivery system 20 includes a blower (e.g., a turbine-based blower), gas delivery control system 31 may reduce the speed of the blower.

Monitoring signals from both sensors 80a and 80b may provide redundancy to account for situations in which 80a or 80b is not providing useful data, e.g., where one of sensors 80a and 80b is damaged or not working properly, or where a proximal pressure line 100 is not used or is blocked.

A second level of over-pressure security is based on pressure measurements from exhalation valve pressure sensor 80c used for detecting the presence of an exhalation valve 96 and controlling the operation of such exhalation valve 96 (e.g., by generating pressure signals used to control a pilot valve 102 that controls exhalation valve 96, as discussed above). For certain exhalation valves 96, the effective surface area upon which gas pressure acts from the command side of the valve (i.e., the side facing exhalation valve control line 98) is larger than the effective surface area upon which gas pressure acts from the breathing circuit side of the valve (i.e., the side facing exhalation valve control line 98). Such configuration may provide the desired sealing of exhalation valve 96.

In normal operation, exhalation valve pressure sensor 80c may be automatically controlled to maintain an internal pressure inside exhalation valve 96 substantially equal to the pressure inside breathing circuit 16 near valve 96, based on pressure measurements from pressure sensors 80a, 80b, and/or 80c. However, in an over-pressure situation, the internal pressure inside exhalation valve 96 may be automatically maintained at a maximum setting level (e.g., an IPAP setting if operating in a barometric mode or a "high pressure" setting if operating in a volumetric mode) based at least on pressure measurements from exhalation valve pressure sensor 80c. In such situation, the pressure inside breathing circuit 16 may exceed the internal pressure inside exhalation valve 96, and exhalation valve 96 may leak, thus reducing and/or limiting the pressure in breathing circuit 16.

Thus, in embodiments or situations in which the first level of over-pressure security is not provided or not effective (e.g., where both sensors 80a and 80b fail, or where gas delivery control system 31 fails to correct an over-pressure situation), the internal pressure inside exhalation valve 96 may be limited based on measurements from exhalation valve pressure sensor 80c, providing leakage through exhalation valve 96, thus reducing and/or limiting the pressure in breathing circuit 16. In this manner, exhalation valve pressure sensor 80c may facilitate the second level of over-pressure security.

Over-pressure security system 32 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Over-pressure security system 32 may be partially or fully integrated with, or may be distinct from, gas delivery control system 31.

Exhalation Valve Detection

As discussed above, exhalation valve detection system 34 is generally operable to determine whether an exhalation valve 96 is present in the current configuration of system 10 (e.g.; whether the currently connected breathing circuit 16 includes an exhalation valve 96) based on pressure signals received from one or more pressure sensors 24.

In some embodiments, exhalation valve pressure sensor 80c may be used to detect whether an exhalation valve 96 is present. For example, gas may be delivered through an outlet configured for connection to an exhalation valve control line 98. If an exhalation valve control line 98 leading to an exhalation valve 96 is present, pressure in exhalation valve control line 98 increases, which increased pressure may be detected by exhalation valve pressure sensor 80c. However, if an exhalation valve control line 98 leading to an exhalation valve 96 is not present, pressure in exhalation valve control line 98 remains low, which low pressure may be detected by exhalation valve pressure sensor 80c. The pressure measured by exhalation valve pressure sensor 80c may thus be compared against an appropriate threshold value to determine whether an exhalation valve 96 is present. Such threshold value may be determined in any suitable manner, and may depend upon various factors, e.g., the current ventilation mode, a flow rate setting, or a pressure setting.

In one embodiment, exhalation valve pressure sensor 80c is connected to a command port of a pilot valve 102 (e.g., an electro valve) that controls exhalation valve 96 on breathing circuit 16 via exhalation valve control line 98. At the beginning of ventilation, pilot valve 102 opens in order to fill exhalation valve 96 via an exhalation valve control line 98 that may be connected to ventilation system 12. If an exhalation valve control line 98 with exhalation valve 96 is connected to ventilation system 12, pressure in exhalation valve control line 98 increases, which is detected by sensor 80c. However, if an exhalation valve control line 98 with exhalation valve 96 is not connected to ventilation system 12, pressure in exhalation valve control line 98 remains low, which is detected by sensor 80c.

Exhalation valve detection system 34 may communicate a notification to gas delivery control system 31 indicating whether system 10 includes an exhalation valve 96. Gas delivery control system 31 may automatically select between different ventilation styles or modes or otherwise control one or more ventilation parameters (e.g., flow and/or pressure) based on such notification, e.g., by controlling gas delivery system 20.

For example, in some embodiments, ventilation system 12 can provide either leakage ventilation or exhalation valve ventilation. Gas delivery control system 31 may automatically control ventilation parameters (e.g., ventilation flow and pressure) to provide either leakage ventilation or exhalation valve ventilation, based on whether or not system 10 includes an exhalation valve 96. If system 10 includes an exhalation valve 96 (e.g., a dual-limb breathing circuit 16 is connected to system 12), gas delivery control system 31 may automatically adapt to provide exhalation valve ventilation; alternatively, if system 10 does not include an exhalation valve 96 (e.g., a single-limb breathing circuit 16 is connected to system 12), gas delivery control system 31 may automatically adapt to provide leakage ventilation. However, if selected ventilator settings or ventilation mode are incompatible with the relevant ventilation type (leakage ventilation or exhalation valve ventilation), gas delivery control system 31 may trigger an alarm and wait for the user to adjust the selected settings to become compatible before beginning ventilation of patient 11. The alarm may comprise any notification that may be sensed by a user, e.g., an audible alarm or a visible alarm displayed to the user, e.g., via display 28 or separate device (e.g., an LED).

Exhalation valve detection system 34 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Exhalation valve detection system 34 may be partially or fully integrated with, or may be distinct from, gas delivery control system 31.

Power System/Battery

Figure 3:
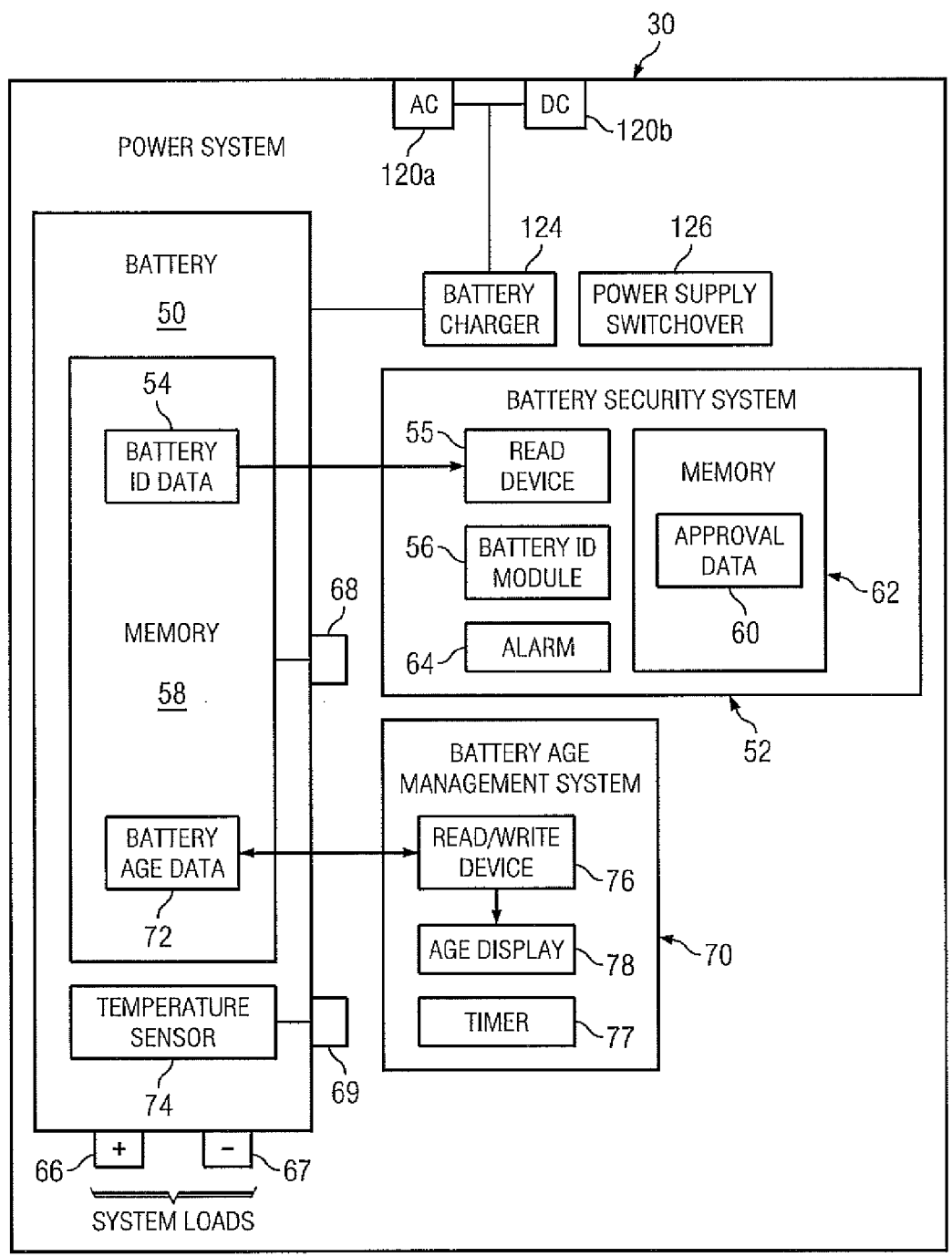
FIG. 3 illustrates details of an example power system for a ventilation system, according to certain embodiments of the present disclosure.

FIG. 3 illustrates details of an example power system 30 for ventilation system 12, according to certain embodiments of the present disclosure. Power system 30 may include or facilitate the connection of one or more sources of power for ventilation system 12, such as an external AC power source, an external DC power source, and/or one or more rechargeable batteries 50, for example. In some embodiments, power system 30 may include one or more converters 124 (e.g., a DC/DC converter and/or an AC/DC converter). One or more power sources may be removable from ventilation system 12. For example, an AC or DC power source or may be plugged into and/or unplugged from ventilation system 12 via one or more power source connections 120. As another example, one or more rechargeable batteries 50 may be inserted into and/or removed from ventilation system 12. In some embodiments, ventilation system 12 may be configured for one or more "swappable" or "hot swappable" batteries 50. In the example embodiment discussed below with reference to FIG. 6, power system 30 may include a lithium battery 50, a connection 120a for an external 110/220V AC power source, a connection 120b for an external 24V DC power source, a battery charger 124, and a power supply switchover 126 for switching between the battery 50 and an external AC or DC power source.

In some embodiments including a battery 50, power system 30 may include a battery security system 52 for ensuring that only compliant or authorized batteries may be used in ventilation system 12 and/or a battery age management system 70 for recording and displaying age data regarding a battery 50, e.g., the number of charge and discharge cycles the battery 50 has experienced.

Battery security system 52 may include a data read device 55, a battery identification module 56, and approval data 60 stored in memory 62 or otherwise accessible by battery identification module 56. Battery security system 52 is generally operable to read battery identification data 54 from battery 50 and determine, based on such data 54, whether battery 50 is approved for use in ventilation system 12. For example, battery security system 52 may compare battery identification data 54 read from a battery 50 with approval data 60 to determine whether the battery 50 is approved.

Battery identification data 54 may be stored in battery 50 (e.g., stored in memory), marked on battery 50 (e.g., a scannable bar code), or otherwise associated with battery 50. In some embodiments, battery identification data 54 may be stored in memory 58 in battery 50. Memory 58 may comprise any type of tangible memory device configured to store electronic data (e.g., RAM, DRAM, ROM, EPROM, Flash memory, or any other memory or storage device). In an example embodiment, memory 58 may comprise a single pin memory configuration such that read and write operations occur through the same pin.

Battery identification data 54 may include any data that may be used for determining whether battery 50 is compliant or authorized, e.g., a product ID number, data identifying the battery manufacturer, data identifying production data (e.g., a date code), data identifying the battery type, data identifying the storage capacity, etc. Battery identification data 54 may or may not be encrypted. In particular embodiments, battery identification data 54 is not encrypted such that neither battery 50 nor system 12 includes encoders and/or decoders for such data.

Approval data 60 may include, for example, approved product ID numbers, approved battery manufacturer(s), approved production data (e.g., approved date codes), approved battery type(s), and/or approved storage capacity(ies). Approval data may be stored in memory 62, which may comprise any type of tangible memory device configured to store electronic data (e.g., RAM, DRAM, ROM, EPROM, Flash memory, or any other memory or storage device).

Data read device 55 may comprise any device configured to read data from battery 50. In particular, data read device 55 may read battery identification data 54 from memory 58 in battery 50.

Battery identification module 56 is generally operable to determine, based on battery identification data 54 read by data read device 55, whether battery 50 is compliant or authorized for use in ventilation system 12. For example, battery identification module 56 may compare battery identification data 54 read from battery 50 with approval data 60 to determine whether the battery 50 is approved.

If battery identification module 56 determines, based on battery identification data 54 read from a battery 50 and/or approval data 60, that a battery 50 inserted in ventilation system 12 is compliant or authorized, module 56 will allow the battery 50 to provide power to system 12 and not trigger an alarm. However, if battery identification module 56 determines that a battery 50 inserted in ventilation system 12 is not compliant or not authorized, module 56 may prevent battery 50 from providing power to system 12 and/or may generate a signal to trigger an alarm 64 to notify the user to remove the non-compliant/unauthorized battery. Alarm 64 may comprise any notification that may be sensed by a user, e.g., audible alarm or a visible alarm displayed to the user. A visible alarm may be displayed in any suitable manner, e.g., an image or text displayed on display 28 or an LED or other light or visible device separate from display 28.

Battery security system 52 may perform such battery authorization process discussed above at any suitable time(s), e.g., upon a triggering event, such as the insertion of battery 50 into system 12 or system 12 being turned on, or in response to a manual user request to check the battery. In some embodiments, battery security system 52 may also automatically perform the battery authorization process periodically, e.g., every hour.

As discussed above, power system 30 may include a battery age management system 70 for recording and displaying age data regarding a battery 50. Battery age management system 70 may include a data read/write device 76 configured to write data to and/or read data from memory 58, including battery age data 72. Battery age data 72 may be stored in memory 58. In alternative embodiments, battery age data 72 and battery identification data 54 may be stored in separate memory devices in battery 50.

Battery age data 72 may include any data regarding the age or usage of a battery 50, e.g., the usage time (e.g., total hours of use), the total number of charge/discharge cycles the battery 50 has experienced, the usage time since the last charge, the effective usage time for the previous charge before needing recharge, etc.

Battery age data 72 may be stored and/or updated in memory 58 in battery 50 in any suitable manner. For example, data read/write device 76 may write battery age data 72 to memory 58 and/or update battery age data 72 stored in memory 58. Updating battery age data 72 may include storing updated data over existing stored data, or storing updated data in addition to existing stored data. Data read/write device 76 may write any type of battery age data 72 to memory 58. Data read/write device 76 may write such data at any suitable time, e.g., periodically or upon a triggering event, such as the beginning or completion of a charge or discharge of battery 50, ventilation system 12 being turned on or off, or ventilation system 12 being plugged into or unplugged from an external power source. Data read/write device 76 may include or have access to a clock or timer 77.

Data read/write device 76 may also read any type of battery age data 72 from memory 58 in battery 50. Data read/write device 76 may read such data at any suitable time, e.g., periodically or upon a triggering event, such as the beginning or completion of a charge or discharge of battery 50, ventilation system 12 being turned on or off, ventilation system 12 being plugged into or unplugged from an external power source, or in response to a user request.

Data read/write device 76 may be configured to display or generate signals for displaying any type of battery age data 72 from memory 58. For example, data read/write device 76 may be generate signals for displaying the total number of charge/discharge cycles the battery 50 has experienced on display 28. In an example embodiment, GUI 40 provides a user interface for accessing various types of battery age data 72 (e.g., using buttons, menus, or other interfaces for selecting the desired battery age data 72).

In other embodiments, battery 50 itself may include processing resources, software or firmware, and/or a clock or timer configured to store and/or update battery age data 72 in memory 50. For example, battery 50 may use such resources to generate and store/update any type of battery age data 72 in memory 50 periodically or upon a triggering event, e.g., the beginning or completion of a charge or discharge of battery 50, ventilation system 12 being turned on or off, or ventilation system 12 being plugged into or unplugged from an external power source. Such triggering events may be detected by battery 50 itself, or via signals communicated from battery age management system 70.

Battery 50 may also include a temperature sensor 74 for monitoring the temperature of battery 50, In some embodiments, temperature sensor 74 is not electrically connected to memory 58.

As shown in FIG. 3, battery 50 may have four contacts: (1) a positive terminal 66, (2) a negative terminal 67, (3) a memory contact 68, and (4) a temperature sensor contact 69. Positive and negative terminals 66, 67 are connected to circuitry within system 12 to provide power to system loads. Memory contact 68 may be connected to data read device 55 of battery security system 52 and/or data read/write device 76 of battery age management system 70, allowing read device 55 and/or data read/write device 76 to communicate data (e.g., battery ID data 54 and/or battery age data 72) to/from memory 58. Temperature sensor contact 69 may provide an interface for communicating battery temperature measurements to one or more components of system 12, e.g., a security system configured to determine whether battery 50 is overheating and respond accordingly.

$O_2$ Safety System $O_2$ safety system 38 is generally configured to slow or stop supplemental oxygen flow when gas delivery system 20 (e.g., a blower) is overheating and/or not running properly. $O_2$ safety system 38 may receive signals from one or more of (a) a temperature sensor 83 configured to measure a temperature of gas delivery system 20 (e.g., a blower); (b) a speed sensor 84 configured to measure an operational speed of a component (e.g., a motor, blower, turbine) of gas delivery system 20; and/or (c) a power monitor 85 configured to measure the power drawn by a component (e.g., a motor, blower, turbine) of gas delivery system 20. If $O_2$ safety system 38 determines an overheat or a danger condition, $O_2$ safety system 38 may generate a command to close an $O_2$ shut-off valve (e.g., O2 safety valve shown in FIGS. 4A, 4B, and 5) to slow or stop the flow of supplemental oxygen.

Figure 4A:
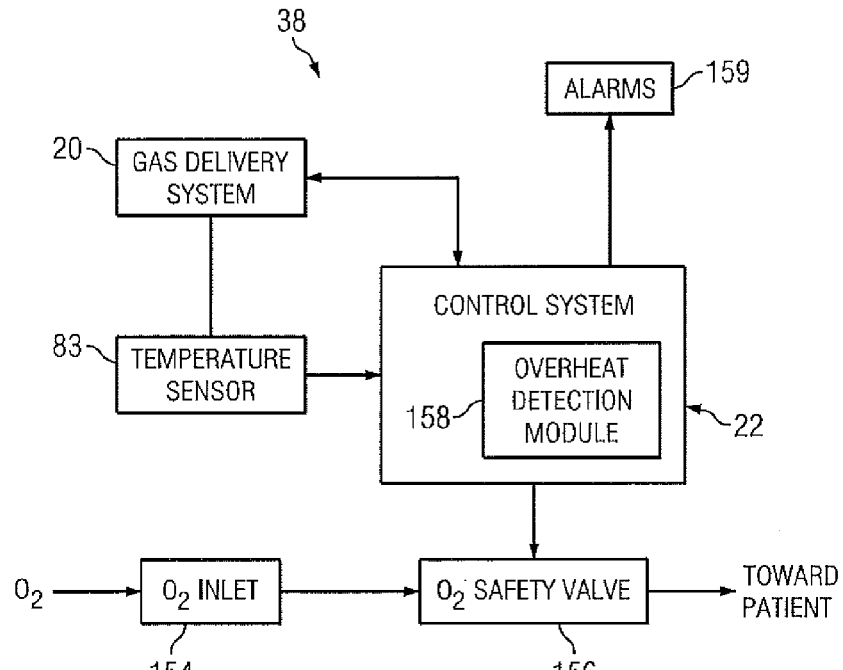
FIGS. 4A and 4B illustrate example $O_2$ safety systems for use with a ventilation system, according to certain embodiments of the present disclosure.
Figure 4B:
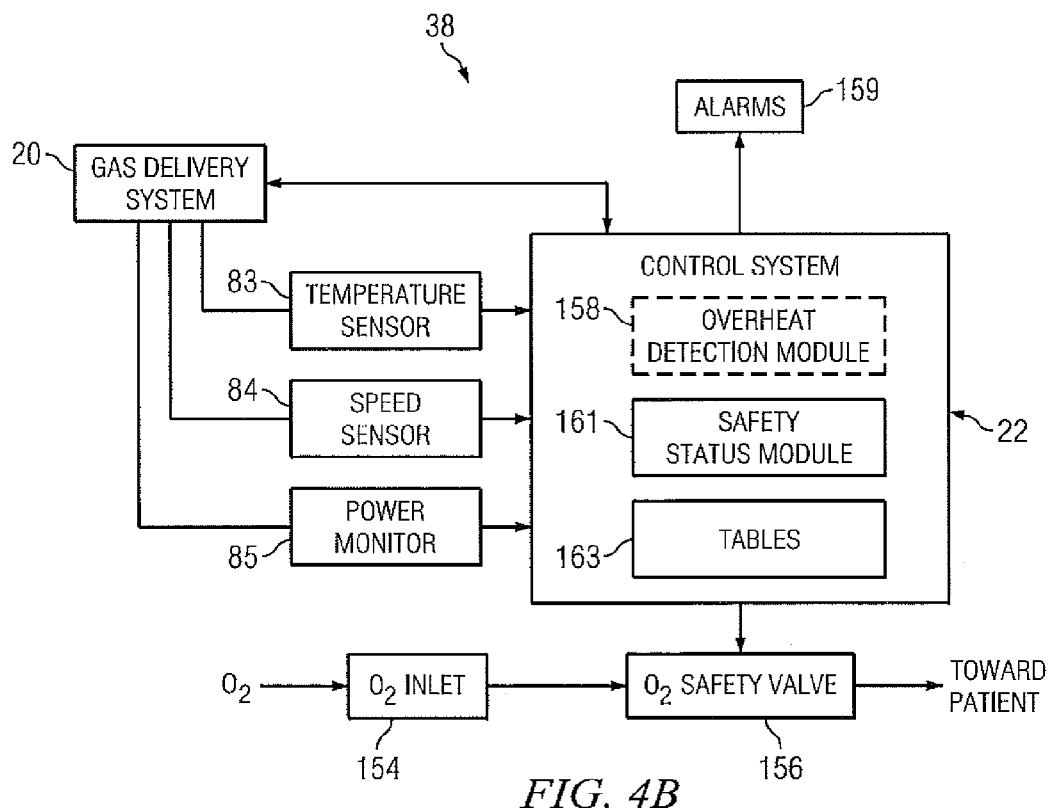

FIGS. 4A and 4B illustrate an example $O_2$ safety system 38 for use with ventilation system 12, according to certain embodiments of the present disclosure. As discussed above, $O_2$ safety system 38 is generally configured to slow or stop a supplemental oxygen flow when gas delivery system 20 (e.g., a blower) is overheating and/or not running properly. As used herein, supplemental oxygen refers to any oxygen-rich gas used to supplement the main gas flow (e.g., air) delivered to a patient 11. For example, supplemental oxygen may include pure oxygen or any other gas having an oxygen concentration greater than air. As used herein, reference to slowing or stopping a supplemental oxygen flow may refer to slowing or stopping the flow of supplemental oxygen from the supplemental oxygen supply (e.g., a tank, a concentrator, or a line from the wall) to the patient 11. For example, slowing or stopping a supplemental oxygen flow may refer to slowing or stopping a flow of supplemental oxygen into ventilation system 12 via a supplemental oxygen inlet (e.g., $O_2$ inlet 154) or through a valve of ventilation system 12 (e.g., $O_2$ safety valve 156). As another example, slowing or stopping a supplemental oxygen flow may refer to opening a release or vent valve to allow supplemental oxygen to flow out and/or away from ventilation system 12.

FIG. 4A illustrates an example $O_2$ safety system 38 in which the supplemental oxygen flow may be controlled based on temperature measurements, e.g., to slow or stop the supplemental oxygen flow in the event of an detected overheat condition. As shown in FIG. 4A, $O_2$ safety system 38 may include a temperature sensor 83, an overheat detection module 158, an O2 safety valve 156, and/or logic associated with gas delivery control system 31.

Temperature sensor 83 is configured to measure the temperature of one or more components of gas delivery system 20 (e.g., a component of a turbine-based blower). Temperature sensor 83 may take temperature measurements at any suitable time and/or frequency, e.g., substantially continuously, periodically (e.g., every 30 seconds), or in response to an event (e.g., a request received from a user).

Overheat detection module 158 is generally configured to determine whether gas delivery system 20 is overheating by monitoring readings from temperature sensor 83. For example, overheat detection module 158 may compare readings from temperature sensor 83 with threshold temperature(s) to determine whether gas delivery system 20 is overheating. Such threshold temperature(s) may be constant or may change over time. For example, a threshold temperature may be determined using an algorithm or look-up table relating the threshold value to one or more other parameters, e.g., the current pressure or flow rate of gas delivered by delivery system 20, or the current speed of a turbine (in embodiments in which gas delivery system 20 comprises a turbine-based blower). Thus, for example, an algorithm may be used to increase the threshold temperature in proportion to the flow rate or turbine speed, as higher temperatures are expected with higher flow rates or turbine speeds.

As another example, different threshold temperatures may be used for different ventilation modes or conditions. For example, different threshold temperatures may be used for SIMV ventilation, Assist/Control ventilation, and CPAP ventilation. As another example, different threshold temperatures may be used for adult vs. pediatric ventilation, as higher temperatures are expected with adult ventilation (e.g., due to higher flow rates or turbine speeds).

Threshold temperatures may be pre-programmed into overheat detection module 158 and/or gas delivery control system 31. Alternatively, threshold temperatures may be set or modified by a user, e.g., an authorized technician. Threshold temperatures may be determined based on empirical data, data regarding various system components (e.g., a maximum temperature that a blower motor can support), based on industry regulations, or determined in any other suitable manner.

In some embodiments, overheat detection module 158 may determine two different overheat levels based on different threshold temperatures—a first overheat level that triggers control of O2 safety valve and a second overheat level that triggers control of gas delivery system 20. The first overheat level may be lower than, higher than, or the same as the second overheat level. For example, overheat detection module 158 may determine a first overheat level for triggering control of O2 safety valve) if the measured temperature exceeds a first threshold temperature $T_1$, and a second overheat level (for triggering control of gas delivery system 20) if the measured temperature exceeds a second threshold temperature $T_2$, where $T_2 > T_1$. Thus, while operating between $T_1$ and $T_2$, gas delivery system 20 may continue to ventilate patient 11 after O2 safety valve has been closed to slow or stop the flow of supplemental oxygen.

In some embodiments, overheat detection module 158 may determine additional overheat levels for triggering control of different components of system 10 based on various threshold temperatures. Each threshold temperature $T_1$, $T_2$, etc. may be determined in any suitable manner, e.g., as discussed above.

Overheat detection module 158 may determine that gas delivery system 20 is overheating based on any number of readings from temperature sensor 83. For example, overheat detection module 158 may determine an overheat condition in response to a single sensor reading above the relevant threshold temperature. As another example, overheat detection module 158 may determine an overheat condition based on a predetermined number (e.g., 5) of consecutive sensor readings above the relevant threshold temperature, based on sensor readings remaining above the relevant threshold temperature for a predetermined duration (e.g., 10 seconds). As another example, overheat detection module 158 may determine an overheat condition based on an average of sensor readings for a predetermined number of readings or over a predetermined duration.

In response to determining an overheat condition in gas delivery system 20, overheat detection module 158 may send an overheat notification signal to gas delivery control system 31. Based on such signal, gas delivery control system 31 may control O2 safety valve and/or gas delivery system 20 accordingly. For example, gas delivery control system 31 may partially or fully close O2 safety valve to slow or stop the flow of supplemental oxygen. O2 safety valve may comprise any suitable type of valve. O2 safety valve may be separate from, or integrated with, $O_2$ inlet 154.

In addition, in some embodiments, gas delivery control system 31 may control gas delivery system 20 in response to an overheat condition. For example, where gas delivery system 20 includes a blower, gas delivery control system 31 may slow or stop the blower in order to reduce the temperature of gas delivery system 20.

In some embodiments, gas delivery control system 31 may control both O2 safety valve and gas delivery system 20 based on a single overheat notification signal. In embodiments using a first overheat level for triggering control of O2 safety valve and a second overheat level for triggering control of gas delivery system 20, gas delivery control system 31 may control O2 safety valve and gas delivery system 20 separately according to the relevant overheat signals received from overheat detection module 158.

In some embodiments, gas delivery control system 31 may control (e.g., close) O2 safety valve based on either of the following input: (a) an overheat notification signal from overheat detection module 158 or (b) a notification of an event regarding gas delivery system 20, e.g., that gas delivery system 20 is not delivering gas (e.g., turned off or in standby mode) or is not operating properly. Thus, for example, the flow of supplemental oxygen may be slowed or stopped if gas delivery system 20 is overheating, turned off, in standby mode, or not operating properly.

Overheat detection module 158 and/or gas delivery control system 31 may generate any suitable alarm(s) 159 regarding overheat conditions and/or the closing of O2 safety valve to slow or stop the flow of supplemental oxygen, An alarm 159 may comprise any notification that may be sensed by a user, e.g., audible alarm or a visible alarm displayed to the user. A visible alarm may be displayed in any suitable manner, e.g., an image or text displayed on display 28 or an LED or other light or visible device separate from display 28.

Overheat detection module 158 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Overheat detection module 158 may be partially or fully integrated with, or may be distinct from, gas delivery control system 31.

FIG. 4B illustrates an example $O_2$ safety system 38 in which the supplemental oxygen flow may be controlled based on any combination of temperature measurements, speed measurements related to gas delivery system 20 (e.g., the speed of a blower motor), and the power drawn by gas delivery system 20 (e.g., the power drawn by a blower motor). The $O_2$ safety system 38 of FIG. 4B may be particularly suitable for embodiments of ventilation system 12 in which gas delivery system 20 includes a motor, e.g., for a blower or turbine.

As shown in FIG. 4B, $O_2$ safety system 38 may include a temperature sensor 83, a speed sensor 84, a power monitor 85, a safety status module 161, an $O_2$ safety valve 156, and/or logic associated with gas delivery control system 31.

Temperature sensor 83 is generally discussed above regarding FIG. 4A. Speed sensor 84 may comprise any system or device configured to measure an operational speed of a motor, blower, turbine, or other component of gas delivery system 20. Power monitor 85 may comprise any system or device configured to measure the power drawn by a motor, blower, turbine, or other component of gas delivery system 20.

Safety status module 161 is generally configured to analyze the operational safety status of gas delivery system 20, including determining conditions regarding gas delivery system 20 (e.g., overheating of a blower motor) that call for controlling $O_2$ safety valve 156. Such conditions are referred to herein as "danger conditions." Safety status module 161 may analyze the operational safety status of gas delivery system 20, including determining danger conditions, based on any combination of some or all of the following types of data, referred to herein as "$O_2$ safety data":

(a) temperature measurements at one or more locations of ventilation system 12;

(b) speed measurements related to gas delivery system 20 (e.g., the speed of a blower motor, fan, or turbine); and/or (c) measurements of the power drawn by gas delivery system 20 or certain component(s) thereof (e.g., the power drawn by a blower motor).

In some embodiments, safety status module 161 may calculate a safety factor using one or more algorithms relating different types of measured $O_2$ safety data, and compare the calculated safety factor to a danger condition threshold value to determine whether a danger condition is present.

In other embodiments, safety status module 161 may access look-up tables 163 relating different types of measured $O_2$ safety data to determine whether a danger condition is present. For example, for an embodiment using temperature measurements and speed measurements as $O_2$ safety data, look-up tables 163 may include a table indicating whether a danger condition is present for various combinations of temperature measurements and speed measurements.

As another example, for an embodiment using temperature measurements and power measurements as $O_2$ safety data, look-up tables 163 may include a table indicating whether a danger condition is present for various combinations of temperature measurements and power measurements.

As another example, for an embodiment using speed measurements and power measurements as $O_2$ safety data, look-up tables 163 may include tables indicating whether a danger condition is present for various combinations of speed measurements and power measurements.

As another example, for an embodiment using temperature measurements, speed measurements, and power measurements as $O_2$ safety data, look-up tables 163 may include tables indicating whether a danger condition is present for various combinations of temperature measurements, speed measurements, and power measurements.

Look-up tables 163 may be stored in any suitable storage medium associated with ventilation system 12. Look-up tables 163 may be generated in any suitable manner, e.g., using mathematical algorithms or based on empirical testing.

In other embodiments, safety status module 161 may determine whether a danger condition is present by comparing individual types of $O_2$ safety data to corresponding threshold values. In some embodiments, the danger condition determination may include a series of two or more threshold comparisons.

For example, for an embodiment using temperature measurements and speed measurements as $O_2$ safety data, safety status module 161 may identify a danger condition where (a) a current temperature measurement surpasses (e.g., is higher than) a temperature threshold value and (b) a current speed measurement surpasses (e.g., is lower than) a speed threshold value.

As another example, for an embodiment using temperature measurements and power measurements as $O_2$ safety data, safety status module 161 may identify a danger condition where (a) a current temperature measurement surpasses a temperature threshold value and (b) a current power measurement surpasses a power threshold value.

As another example, for an embodiment using speed measurements and power measurements as $O_2$ safety data, safety status module 161 may identify a danger condition where (a) a current speed measurement surpasses (e.g., is lower than) a speed threshold value and (b) a current power measurement surpasses (e.g., is higher than) a power threshold value.

As another example, for an embodiment using temperature measurements, speed measurements, and power measurements as $O_2$ safety data, safety status module 161 may identify a danger condition where (a) a current temperature measurement surpasses a temperature threshold value, (b) a current speed measurement surpasses a speed threshold value, and (c) a current power measurement surpasses a power threshold value.

As used herein, the term "surpassed" may refer to a measurement rising above a threshold value or to a measurement falling below a threshold value, depending on the particular embodiment and the particular setting for the threshold value. For example, in certain applications, a motor speed threshold value of 1,000 rpm may be surpassed when the motor speed increases above 1,000 rpm, while in other applications the motor speed threshold value may be surpassed when the motor speed falls below 1,000 rpm.

Each of the threshold values used by safety status module 161 (e.g., temperature threshold values, speed threshold values, and/or power threshold values) may be determined in any suitable manner and may be constant or may change over time. For example, a particular threshold value may be determined using an algorithm or look-up table relating the threshold value to one or more other parameters, e.g., the current pressure or flow rate of gas delivered by delivery system 20, or the current speed of a turbine (in embodiments in which gas delivery system 20 comprises a turbine-based blower).

As another example, different threshold values may be used for different ventilation modes or conditions. For example, different threshold values may be used for SIMV ventilation, Assist/Control ventilation, and CPAP ventilation. As another example, different threshold values may be used for adult vs. pediatric ventilation, as higher temperatures are expected with adult ventilation (e.g., due to higher flow rates or turbine speeds).

One or more threshold values may be pre-programmed into overheat detection module 158 and/or gas delivery control system 31. Alternatively, one or more threshold values may be set or modified by a user, e.g., an authorized technician. One or more threshold values may be determined based on empirical data, data regarding material properties of various system components, based on industry regulations, or determined in any other suitable manner.

In embodiments in which safety status module 161 compares temperature measurements to a temperature threshold value, safety status module 161 may cooperate with an overheat detection module 158, which may provide any of the functionality discussed above with respect to FIG. 4A, e.g., using different threshold temperatures for determining different overheat levels for triggering control of different components of system 10 based on various threshold temperatures.

Safety status module 161 may identify a danger condition based on any number of readings from temperature sensor 83, speed sensor 84, and/or power monitor 85. For example, in an embodiment using temperature sensor 83 and speed sensor 84, safety status module 161 may identify a danger condition based on a single reading from each of temperature sensor 83 and speed sensor 84. As another example, safety status module 161 may identify a danger condition based on a predetermined number (e.g., 5) of consecutive readings from sensors 83 and 84 indicate a danger condition, or where consecutive sensor readings indicate a danger condition for more than a predetermined duration (e.g., 10 seconds), or where an average of sensor readings for a predetermined number of readings or over a predetermined duration indicate a danger condition.

In response to determining a danger condition in gas delivery system 20, safety status module 161 may send a danger condition notification signal to gas delivery control system 31. Based on such signal, gas delivery control system 31 may control O2 safety valve and/or gas delivery system 20 accordingly. For example, gas delivery control system 31 may partially or fully close $O_2$ safety valve to slow or stop the flow of supplemental oxygen. O2 safety valve may comprise any suitable type of valve. O2 safety valve may be separate from, or integrated with, $O_2$ in let 154.

In addition, in some embodiments, gas delivery control system 31 may control gas delivery system 20 in response to a danger condition. For example, where gas delivery system 20 includes a blower, gas delivery control system 31 may slow or stop the blower in order to reduce the temperature of gas delivery system 20.

In some embodiments, gas delivery control system 31 may control both O2 safety valve and gas delivery system 20 based on a single danger condition notification signal. In some embodiments, gas delivery control system 31 may control O2 safety valve and gas delivery system 20 separately according to different danger condition threshold levels.

In some embodiments, gas delivery control system 31 may control (e.g., close) O2 safety valve based on either of the following input: (a) a danger condition notification signal from safety status module 161 or (b) a notification of an event regarding gas delivery system 20, e.g., that gas delivery system 20 is not delivering gas (e.g., turned off or in standby mode) or is not operating properly. Thus, for example, the flow of supplemental oxygen may be slowed or stopped if gas delivery system 20 is overheating, turned off, in standby mode, or not operating properly.

Safety status module 161 and/or gas delivery control system 31 may generate any suitable alarm(s) 159 regarding danger conditions and/or the closing of O2 safety valve to slow or stop the flow of supplemental oxygen. An alarm 159 may comprise any notification that may be sensed by a user, e.g., audible alarm or a visible alarm displayed to the user. A visible alarm may be displayed in any suitable manner, e.g., an image or text displayed on display 28 or an LED or other light or visible device separate from display 28.

Safety status module 161 may include or have access to one or more controllers, processors, memory devices, and any other suitable hardware, software, and/or firmware for providing any of the various functionality discussed herein. Such memory device(s) may store instructions (e.g., any suitable software, algorithms, or other logic or instructions that may be executed by one or more processors) for providing such functionality. Safety status module 161 may be partially or fully integrated with, or may be distinct from, gas delivery control system 31.

Although the discussion herein focuses on safety systems for a supplemental supply of oxygen, the various techniques discussed herein may similarly be used for providing a safety system for a supply of any other type of gas or gas mixture (e.g., an oxygen-rich mixture).

Example Ventilation Systems

FIG. 5 illustrates a flow path diagram showing various components and gas flow paths in an example embodiment of ventilation system 12, indicated as ventilation system 12a, according to one embodiment of the present disclosure. The particular set of components, and arrangement of such components, shown in ventilation system 12a represent only an example embodiment ventilation system 12; in other embodiments ventilation system 12 may include different components and/or a different arrangement of components.

An example dual-limb breathing circuit 16 is shown connected to ventilation system 12a. However, a different type of dual-limb breathing circuit, or a single-limb breathing circuit, may be connected to ventilation system 12a.

Ventilation system 12a provides a first flow path for air flow and a second, optional flow path for supplemental oxygen. Air flow path may include an air inlet filter 140, an inlet silencer 150, a turbine-based blower 20, and an outlet silencer 152. Air inlet filter 140 may be any filter suitable for filtering or cleaning air before entering turbine 20. For example, air inlet filter 140 may comprise a double material filter, e.g., including a fine particulate portion and a rough foam portion. Turbine 20 may comprise a high-speed, low-inertia air compressor configured to control the air flow and/or pressure through the mainstream pathway toward inspiration flow outlet 130. Silencers 150 and 152 may comprise any noise devices for suppressing noise from the inlet or outlet interfaces of turbine 20. For example, silencers 150 and 152 may comprise any suitable materials that provide noise damping, absorbing, and/or insulating, e.g., foams and other materials such as those provided by PINTA ENAC S.A.S. (http:/www.pinta-enac.com/index_eng.html). In addition, such foams or other noise controlling materials may be configured to form a labyrinth or other convoluted or tortuous path to provide additional noise control.

The supplemental oxygen flow path may include an O2 inlet 154 and an O2 safety valve, after which the path may combine with the air flow path at a union 128. Oxygen inlet 154 may comprise a low-pressure oxygen inlet interface for connecting to a supplemental oxygen source (e.g., a tank, compressor, or line-in from a wall). It may include a safety coupling valve for preventing leakage during disconnection of the oxygen source. O2 safety valve may close oxygen inlet 154 when ventilation system 12a is turned off or otherwise not providing ventilation, e.g., as discussed above regarding O2 safety system 38.

The combined paths may then continue toward an inspiration flow outlet 130, to which an inspiration limb 90 of breathing circuit 16 may be connected. An over-pressure pressure relief valve 160, an inspiration flow sensor 82a, and an outlet pressure sensor 80a may be connected between union 128 and inspiration flow outlet 130. Over-pressure pressure relief valve 160 may comprise any known pressure relief valve. Relief valve 160 may be configured to protect the patient from dangerous over-pressure situations. Other embodiments may not include relief valve 160, and may utilize an over-pressure safety system using pressure measurements from sensors 80a and/or 80b and gas delivery control system 31 to control turbine 20, e.g., as discussed above regarding over-pressure security system 32. Flow sensor 82a may monitor the flow delivered toward the patient, and outlet pressure sensor 80a may monitor the pressure at the outlet of ventilation system 12a, e.g., to provide safety back-up pressure measurement when proximal pressure line 100 is not connected, An exhalation limb 90 of breathing circuit 16 may be connected to an exhalation flow inlet 132, which may be directed toward an exhalation flow outlet 134 leading out of ventilation system 12a. An exhalation flow sensor 82b may be located between exhalation flow inlet 132 and exhalation flow outlet 134 to measure the exhalation flow.

Ventilation system 12a may also include an exhalation valve control system for controlling exhalation valve 96. Such exhalation valve control system may include a pilot valve 102 and an exhalation valve pressure sensor 80c positioned along a flow line 138 from blower 20 (e.g., such line directly output from blower 20 or branching off of the main flow line directed toward inspiration flow outlet 130). The flow line 138 may lead to an exhalation valve interface 134 for connecting an exhalation valve control line 98 used for controlling exhalation valve 96.

Ventilation system 12a may also include a proximal pressure sensor 80b connected to a proximal pressure interface 136 configured for connecting a proximal pressure line 100, which may run along limb 90 or 92 of breathing circuit 16. Proximal pressure sensor 80b may monitor the gas pressure delivered toward the patient when proximal pressure line 100 is connected to ventilation system 12.

Any of the various sensors and/or valves of system 12a may communicate signals to gas delivery control system 31, which may process such signals and control the speed of turbine 20 accordingly. Gas delivery control system 31 may also communicate control signals to control the operation of any of the valves of system 12a.

FIG. 6 illustrates an example arrangement of various components of example ventilation system 12a, according to one embodiment of the present disclosure. Beginning at the air intake pathway, ventilation system 12a may include air inlet filter 140 leading to first silencer 150 of a turbine-based blower module. Intake air may then be compressed by turbine 20 and delivered through second silencer 152 and along the main flow line 190 toward the connection interface 130 for the inhalation limb of a breathing circuit 16.

A check valve 160 may be located along main flow line 190. Check valve 160 may comprise a mechanical (e.g., spring-based) or pneumatic relief valve configured to automatically open in the event of an overpressure situation. Some embodiment may not include check valve 160. Inhalation flow sensor 82a and inhalation pressure sensor 80a may also be located along main flow line 190, and configured to measure the flow rate and pressure in main flow line 190.

An O$_2$ inlet 154 may be configured for connecting a supplemental oxygen source. An O$_2$ safety valve 156 may be located along O$_2$ flow line 192, and configured to slow or stop the flow of supplemental oxygen in certain situations, e.g., as discussed above regarding FIGS. 4A and 4B. O$_2$ flow line 192 may lead to a mixing chamber or area such that the supplemental oxygen may mix with the output air from turbine 20 and continue toward patient 11 along main flow line 190 inhalation limb connection interface 130 as an air-O$_2$ mixture.

An exhalation limb connection interface 132 provides an interface for connecting an exhalation limb of a breathing circuit 16, and leads to an exhalation flow line 194. An exhalation flow sensor 82b for measuring the exhalation flow rate is located along exhalation flow line 194 before the flow is directed out of and away from system 12.

An exhalation valve control line interface 134 provides an interface for connecting an exhalation valve control line for controlling an exhalation valve in a breathing circuit 16. Exhalation valve control line interface 134 is connected to the turbine-based blower module via a pressurized control line 196 such that pressurized gas can be applied to the exhalation valve in order to control the exhalation valve. A pilot valve 102 (e.g., a solenoid) may control the pressure within control line 196. Pilot valve 102 may be controlled by signals from CPU 22, which may be generated based on pressure measurements from a pressure sensor 80c located along control line 196.

A user interface module 40 may include a display (e.g., an LCD or other screen) and a keypad 42 including any number and/or type of keys, buttons, switches, or other manual interfaces. CPU 22 may include any one or more processor configured to communicated with and/or control any of the various components of system 12a. CPU 22 may include or may have access to any software, firmware, algorithms, or other logic or instructions for performing any of the various control functions discussed herein.

Various components may be physically located on a circuit board. In this example, CPU, sensors 80a, 80c, 82a, and 82b, and user interface module 40 are located on a circuit board 198.

CPU 22 may control a turbine control device 200 configured to control the operation of turbine 20. Turbine control device 200 may be configured to provide any suitable performance characteristics, as desired. For instance, in an example embodiment, turbine control device 200 is designed according to the following performance characteristics:

The device drives from 0 to 45,000 rpm a 3-phase brushless motor with position or motor speed sensors;

The device transfers signals from a Motor position or motor speed sensor;

The device transfers signals from a motor temperature sensor;

The device allows the motor supply to be cut by an external control;

The device allows breaking of the motor by an external source;

The inrush current of the device is less than 3 A; and

The power supply current is less than 3 A.

CPU 22 may control turbine control device 200 based on any suitable data, e.g., data from one or more sensors and/or data input by a user via user interface module 40.

One or more data ports 206 may provide a connection interface for communicating data to and/or from system 12 (e.g., CPU 22). Each data port 206 may comprise any suitable type of data port, e.g., a USB, Ethernet, FireWire, or RS-232 port.

A repeater interface 202 provides an interface for connecting a wireless notification module 44 for wirelessly communicating data (e.g., alarms and/or other data) to wireless receiving devices via one or more wireless repeaters. Such system is discussed below with reference to FIG. 7.

An FiO2 socket 204 for connecting a FiO2 sensor (e.g., oxygen cell) for providing measurements of the oxygen concentration (or percent oxygen) of the gas delivered toward patient 11. Ventilation system 12 may use such measurements for monitoring the oxygen concentration in the patient air flow, e.g., for triggering Low and High FiO2 alarms based on Low and High FiO2 thresholds (which may be set by a user via GUI 40, automatically determined by system 12, or otherwise determined).

A power system 30 may include a battery 50, an AC/DC power supply and battery charger 124, and a power switchover 126, e.g., as discussed above with reference to FIG. 3. An AC/DC source interface 210 and an on/off switch 212 may be connected to AC/DC power supply and battery charger 124.

Wireless Notification System

Figure 7:
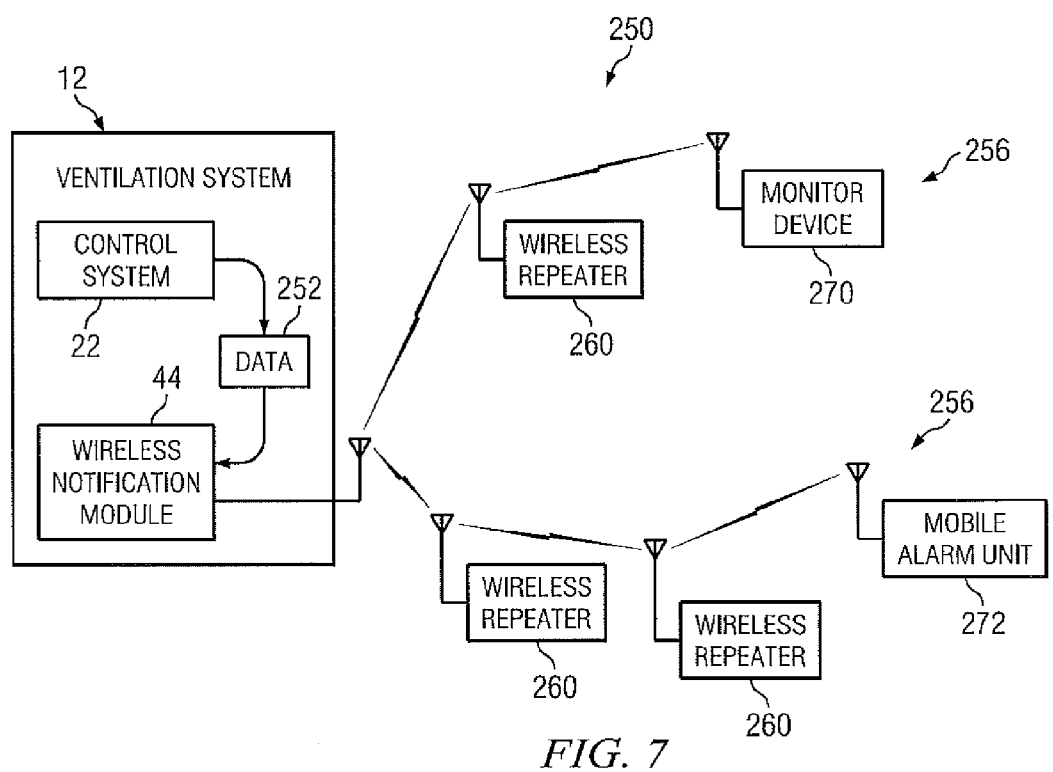
FIG. 7 illustrates an example wireless notification system configured to communicate wireless notifications (e.g., alarms) from a ventilation system to one or more receiving devices, according to certain embodiments of the present disclosure.

FIG. 7 illustrates an example wireless notification system 250 configured to communicate wireless notifications (e.g., alarms generated by control system 22) from ventilation system 12 to one or more receiving device, e.g., a remote monitor or a mobile alarm unit carried by a user (e.g., a caretaker). In some embodiments, wireless notification system 250 may include a wireless notification module 44 included in or coupled to ventilation system 12, one or more wireless repeaters 260, and one or more wireless receiving devices 256. In general, wireless notification module 44 may be configured to wirelessly transmit alarms or other data to wireless receiving devices 256, either directly or via one or more wireless repeaters 260.

Wireless notification module 44 may be included in or coupled to ventilation system 12. For example, module 44 may be integrated with ventilation system 12. Alternatively, module 44 may be a separate module that may be connected to an interface of ventilation system 12 via any suitable wireline or wireless interface, e.g., USB, Ethernet, or Bluetooth connection. In the example embodiment shown in FIG. 6, module 44 may be configured to connection to ventilation system 12 via repeater interface 202. Wireless notification module 44 may include any hardware, software, firmware, etc. for communicating with components of ventilation system 12 (e.g., control system 22) and wirelessly communicating data 252 from such components of ventilation system 12 to one or more wireless receiving devices 256, either directly or via one or more wireless repeaters 260. In an example embodiment, wireless notification module 44 may include an RF modem configured to transmit and/or receive wireless signals.

Each wireless repeater 260 may comprise any type of known repeater for wirelessly relaying data 252 between two devices (e.g., between a computing device and a wireless access point). More particularly, each wireless repeaters 260 may relay data (a) between wireless notification module 44 and a receiving device 256, (b) between wireless notification module 44 and another wireless repeater 260, and (c) between two other wireless repeaters 260. In this manner, wireless repeaters 260 facilitate communication of data 252 between wireless notification module 44 and receiving devices 256.

Wireless notification system 250 may include any number of wireless repeater 260 positioned and at any suitable locations. For example, wireless repeaters 260 may be aligned in a row to provide wireless coverage for a distance in one direction, or may be arranged in an array to provide wireless coverage over a desired area. In some embodiments, wireless repeaters 260 may be located in multiple rooms throughout a building to provide wireless coverage throughout the building.

Wireless receiving devices 256 may include any one or more types of devices configured to (a) wirelessly receive data 252 from wireless notification module 44, either directly or via one or more wireless repeaters 260 and (b) communicate the received data 252 to a person (e.g., a caretaker) remote from ventilation system 12. A wireless receiving devices 256 may communicate data 252 to a person in any suitable manner, e.g., (a) visually displaying the data via a visible display device (e.g., a screen, monitor, LEDs, etc.), (b) generating various audible sounds or voice messages via a speaker or other suitable device, (c) vibrating, or (d) any combination of the above.

Wireless receiving devices 256 may include one or more monitor devices 270 and mobile alarm units 272. A monitor device 270 may comprise any device having a monitor or screen for visually displaying data 252. For example, monitor device 270 may comprise a monitor or screen of a computer, a television, or a stand-alone monitor device. Mobile alarm units 272 may include any mobile device that may be carried by a person, e.g., a hand-held device or a device that may be attached to the person's clothing. Mobile alarm units 272 may include devices having other functionality not related to wireless notification system 250 (e.g., a mobile phone, PDA, or portable computer) and/or devices specifically designed for wireless notification system 250. For certain device (e.g., mobile phone, PDA, or portable computers having other, unrelated functionality), software may be installed onto such devices in order to provide the relevant functionality (e.g., data communication, processing, and display functionality) of a wireless receiving devices 256 for use in wireless notification system 250.

Data 252 may include any type of data regarding the condition of patient 11 and/or the operation of breathing assistance system 10. In some embodiments, data 252 includes alarm data, e.g., notifications of alarms generated by any of the sub-systems of control system 22 (including, for example, any of the various alarms discussed herein). Some alarms may indicate any fault or malfunction regarding the operation of any one or more sub-system or component of breathing assistance system 10. Other alarms may indicate a dangerous or potentially dangerous physiological condition of patient 11.

In other embodiments, data 252 includes alarm data as well as other data regarding patient 11 and/or breathing assistance system 10, e.g., ventilator settings, sensor readings (e.g., pressure, flow, and temperature data), and/or physiological measurements regarding patient 11. In some embodiments, data 252 (e.g., ventilator settings, sensor readings, and/or physiological measurements) may be continuously or substantially continuously communicated to wireless receiving devices 256 such that the data may be continuously or substantially continuously displayed and updated by the wireless receiving devices 256.

Data 252 may also include data identifying the particular ventilation system 12 and/or the particular patient 11. In some configurations, data 252 may include "heartbeat" signals or other signals for indicating the presence and/or operational status of the communicating device.

As discussed above, in some embodiments or configurations, wireless notification module 44 may communicate data 252 to wireless receiving devices 256 continuously or substantially continuously. Such communications may include alarms and/or other data.

In other embodiments or configurations, wireless notification system 250 is essentially a remote alarm system, designed mainly for communicating alarms. In some such embodiments, wireless notification module 44 may maintain continuous (or frequent) communications with wireless receiving devices 256, e.g., my "heartbeat" signals or other signals indicating the presence and/or operational status (e.g., "powered on") of each wireless receiving device 256. When an alarm condition occurs in system 10, wireless notification module 44 may interrupt the continuous (or frequent) communications with wireless receiving devices 256; in response to the interrupt in communications, each wireless receiving device 256 may generate an alarm. Each wireless receiving device 256 may also generate an alarm if it moves outside the range for receiving communications from wireless notification module 44 (e.g., if device 256 cannot communicate with wireless notification module 44 or any wireless repeater 260).

Alternatively, when an alarm condition occurs in breathing assistance system 10, wireless notification module 44 may transmit an alarm signal (as data 252) to wireless receiving devices 256 (again, either directly or via one or more repeaters 260), and in response, each wireless receiving device 256 may generate an alarm (e.g., an audible or visible alarm). In some embodiments, wireless receiving device 256 may generate a first type of alarm when it receives an alarm signal transmitted by wireless notification module 44, and a second first type of alarm when communications with wireless notification module 44 are interrupted (e.g., due to moving outside the range of communication with wireless notification module 44 or any wireless repeater 260, or due to a fault associated with any component of wireless notification module 44.

Components of wireless notification system 250 (e.g., wireless notification module 44, wireless repeaters 260, and wireless receiving devices 256) may be powered in any suitable manner, e.g., by battery or from an electrical power grid (e.g., via an A/C wall outlet). For example, in some embodiments, wireless notification module 44 may be powered by power system 30 of ventilation system 12, wireless repeaters 260 may plugged into a wall outlet or powered by battery, and wireless receiving devices 256 may be powered by rechargeable battery. In some embodiments, components of wireless notification system 250 operating on battery power may generate a low battery alarm when appropriate. Such alarm may notify the user to replace or recharge the battery.

In some embodiments, wireless notification system 250 may utilize power management techniques for reducing power used by various system components (e.g., wireless notification module 44, wireless repeaters 260, and wireless receiving devices 256). For example, various system components may enter a low power mode (e.g., a sleep, standby, or low power mode) when not communicating data, in order to conserve power. System components may be awakened or enter a full power or powered up mode as appropriate in order to transmit and/or receive data. For example, one system component (e.g., wireless notification module 44) may communicate a "wakeup" signal to wireless repeaters 260 and/or wireless receiving devices 256 in order to awaken such components for receiving and/or transmitting data. Such "wakeup" signals may be communicated periodically or at any other time for communicating data 252. Alternatively, various system components may be synchronized and awaken themselves in a synchronized manner in order to communicate data 252. In such embodiments, each system component may maintain a clock, and synchronization signals may be communicated among the system components periodically in order to keep the component clocks synchronized.

Any of the components of wireless notification system 250 (e.g., wireless notification module 44, wireless repeaters 260, and wireless receiving devices 256) may include any hardware, software, and/or firmware for transmitting and/or receiving wireless communications of data (e.g., data 252). For example, components of wireless notification system 250 may include any suitable wireless transmitters, wireless receivers, and/or wireless transceivers. In some embodiments, each of wireless notification module 44, wireless repeaters 260, and wireless receiving devices 256 include both transmitters and receivers (or transceivers) such that data may be communication in both directions between wireless notification module 44 and wireless receiving devices 256.

The wireless communications between the various components of wireless notification system 250 may use any known protocol or standard. Examples of wireless communication protocols that may be used include, but are not limited to, personal area networks (PAN) (e.g., BLUETOOTH), local area networks (LAN), wide area networks (WAN), narrowband personal communications services (PCS), broadband PCS, circuit switched cellular, cellular digital packet data (CDPD), radio frequencies, such as the 800 MHz, 900 MHz, 1.9 GHz and 2.4 GHz bands, infra-red and laser.

In some embodiments, wireless notification system 250 may fixed-frequency communications. In other embodiments, wireless notification system 250 may spread-spectrum communications, e.g., by means of frequency-hopping, direct sequence, or any other known techniques.

In some embodiments, wireless receiving devices 256 may communicate data to wireless notification module 44. For example, each wireless receiving device 256 may communicate identification data and/or location data to wireless notification module 44 at any suitable time, for example, substantially continuously, periodically, or in response to some triggering event (e.g., wireless receiving device 256 being turned on or preparing to communicate a control signal to wireless notification module 44, for example, to remotely change a ventilation setting).

In some embodiments, wireless notification system 250 may include an identification or security system to ensure that only authorized devices are communicating in system 250. Some or all system components may store identification data that may be communicated to other system components for authentication of system components. For example, in order to enter a communication session with wireless notification module 44, the wireless receiving device 256 may communicate identification data to module 44 at any suitable time, for example, periodically, upon powering up device 256, module 44, or ventilation system 12, or in response to a request by module 44. Thus, wireless notification module 44 may manage the authentication process. In other embodiments, wireless repeaters 260 may be configured to manage the authentication process.

Example Methods of Operation

Figure 8:
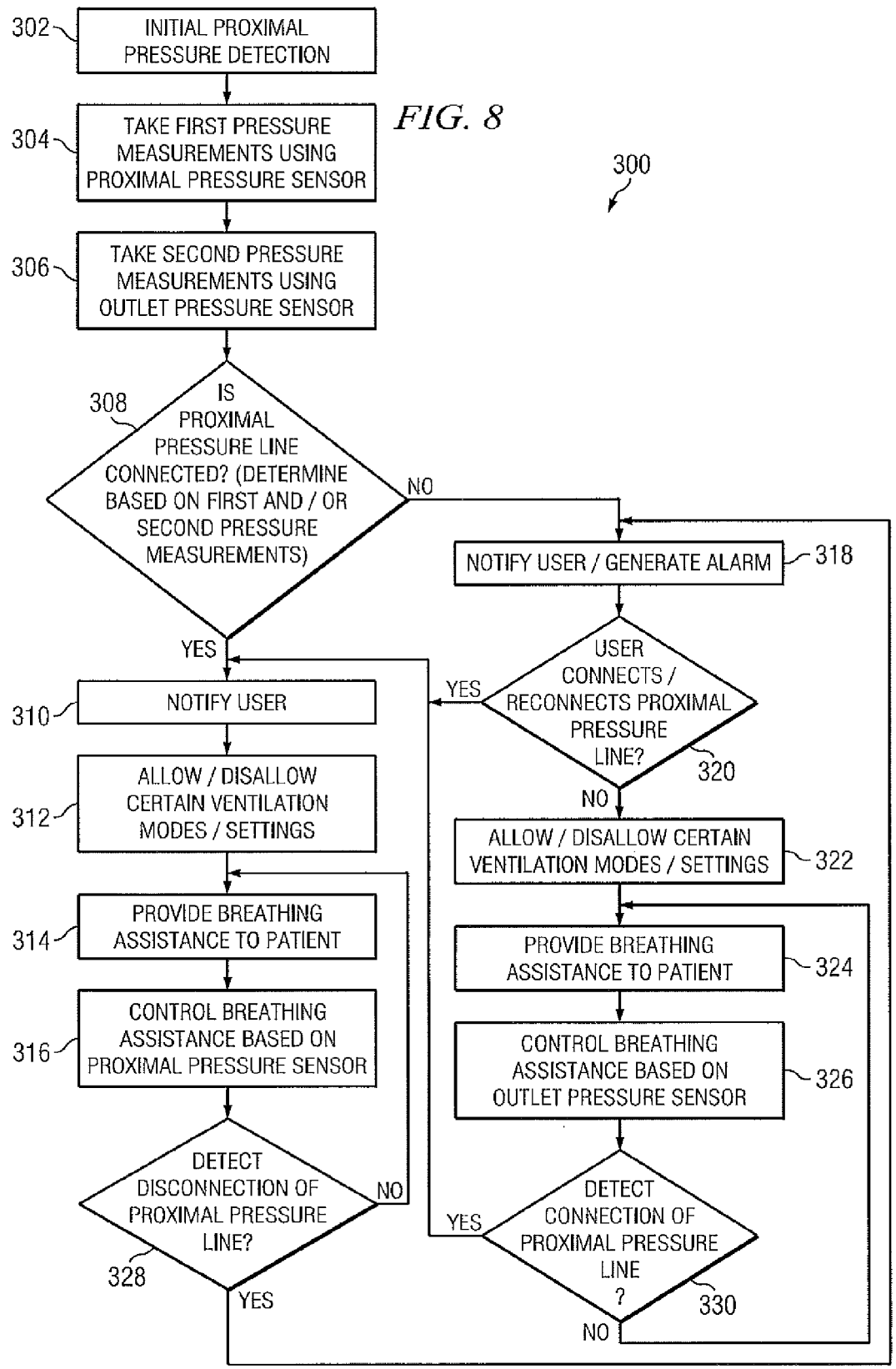
FIG. 8 illustrates an example method of using multiple pressure sensors for managing control of a ventilation system, according to certain embodiments of the present disclosure.

FIG. 8 illustrates an example method 300 of using multiple pressure sensors for managing control of a ventilation system 12, according to certain embodiments of the present disclosure. The example method 300 uses two pressure sensors for managing control of ventilation system 12. In particular, in the discussion below, the two pressure sensors are outlet pressure sensor 80a and proximal pressure sensor 80b. However, method 300 may similarly apply to other pairs of pressure sensors provided in breathing assistance system 10, depending on the specific embodiment. Such pair of pressure sensors may be positioned at any location in breathing assistance system 10, and may be configured to measure pressure at any different locations within breathing assistance system 10, e.g., any locations along a conduit of ventilation system 12 and/or connection system 14. In addition, although example method 300 uses two pressure sensors for managing control of ventilation system 12, similar techniques may be used for managing control of ventilation system 12 using more than two (e.g., 3 or more) pressure sensors.

At step 302, a proximal pressure detection process is initiated. Such process may be initiated automatically upon a triggering event (e.g., turning on ventilation system 12, user or automatic selection of a particular ventilation mode or setting, or execution of a start-up test) or based on a user-initiated request. In general, as discussed below, the proximal pressure detection process determines whether a proximal pressure line 100 is connected to ventilation system 12 such that proximal pressure sensor 80b may effectively measure the proximal pressure (e.g., pressure in connection system 14 near patient 11) for use in controlling the operation of ventilation system 12 (e.g., whether proximal pressure sensor 80b may be used by gas delivery control system 31 may control the pressure and/or flow of gas delivered toward patient 11).

At step 304, proximal pressure sensor 80b may take and communicate one or more pressure measurements to proximal pressure detection system 36. Proximal pressure sensor 80b may communicate a single pressure measurement or multiple pressure measurements over any suitable time period.

At step 306, outlet pressure sensor 80a may take and communicate one or more pressure measurements to proximal pressure detection system 36. Outlet pressure sensor 80a may communicate a single pressure measurement or multiple pressure measurements over any suitable time period. Steps 304 and 306 may be performed in any order and/or substantially simultaneously.

At step 308, proximal pressure detection system 36 may determine whether a proximal pressure line 100 is connected to ventilation system 12 such that proximal pressure sensor 80b may effectively measure the proximal pressure (e.g., the pressure in connection system 14 near patient 11). Proximal pressure detection system 36 may determine whether a proximal pressure line 100 is connected based at least on (a) pressure measurements from proximal pressure sensor 80b at step 304, (b) pressure measurements from outlet pressure sensor 80a at step 306, or (c) both.

For example, proximal pressure detection system 36 may compare measurement(s) from proximal pressure sensor 80b with measurement(s) from outlet pressure sensor 80a, and determine that a proximal pressure line 100 is connected if the proximal pressure sensor 80b measurement(s) is/are greater than the outlet pressure sensor 80a measurement(s), and that a proximal pressure line 100 is not connected if the proximal pressure sensor 80b measurement(s) is/are less than or equal to than the outlet pressure sensor 80a measurement(s), As another example, proximal pressure detection system 36 may determine that a proximal pressure line 100 is connected if the proximal pressure sensor 80b measurement(s) is/are greater than the outlet pressure sensor 80a measurement(s), but by an amount within a threshold pressure difference (e.g., determined based on empirical data). In such embodiments, such threshold pressure difference may be selected from a set or range of predetermined threshold pressure difference based on the particular flow rate at which the outlet pressure sensor 80a measurement(s) were taken. Such set or range of predetermined threshold pressure difference may be used to account for the fact that, in certain configurations, the expected difference in pressure measurements between outlet pressure sensor 80a and proximal pressure sensor 80b (e.g., due to pressure drop within connection system 14) depends on the flow rate through connection system 14. Thus, the higher the flow rate through connection system 14 during the pressure measurements at steps 304 and/or 306, the higher the expected difference between proximal pressure sensor 80b measurement(s) and outlet pressure sensor 80a measurement(s), and thus the higher the threshold pressure difference that should be used.

Note that these two examples assume positive direction flow (i.e., toward patient 11); for negative direction flow (i.e., away from patient 11), the analysis would be reversed.

As another example, proximal pressure detection system 36 may compare the proximal pressure sensor 80b measurement(s) to a threshold pressure value (e.g., determined based on empirical data), and determine that a proximal pressure line 100 is connected if the proximal pressure sensor 80b measurement(s) is/are greater than the threshold pressure value, and that a proximal pressure line 100 is not connected if the proximal pressure sensor 80b measurement(s) is/are less than or equal to the threshold pressure value.

As another example, proximal pressure detection system 36 may compare the proximal pressure sensor 80b measurement(s) to a predetermined expected pressure value (e.g., determined based on empirical data), and determine that a proximal pressure line 100 is connected if the proximal pressure sensor 80b measurement(s) do not differ from the predetermined expected pressure value by more than a predetermined threshold value.

In other embodiments, proximal pressure detection system 36 may analyze (a) proximal pressure sensor 80b measurement(s), (b) outlet pressure sensor 80a measurement(s), or (e) both, in any other manner to determine whether a proximal pressure line 100 is connected to ventilation system 12.

If proximal pressure detection system 36 determines at step 308 that a proximal pressure line 100 is connected to ventilation system 12, the method may advance to step 310. At step 310, system 36 may generate and/or display to the user a notification that a proximal pressure line 100 is connected and/or that proximal pressure sensor 80b measurements) will or may be used for controlling aspects of ventilation system 12.

At step 312, control system 31 may allow or disallow particular ventilation modes or settings based on the determination that a proximal pressure line 100 is connected to ventilation system 12 (and that proximal pressure sensor 80b measurement(s) may be used for controlling ventilation system 12). For example, control system 31 may allow user or automatic selection of, and/or automatic switching to, certain ventilation modes or settings that require accurate patient pressure readings that may be provided by proximal pressure sensor 80b but not by outlet pressure sensor 80a. As discussed below at step 322, one or more of such ventilation modes or settings may be disallowed if it is determined that a proximal pressure line 100 is not connected to ventilation system 12.

At step 314, ventilation system 12 may provide breathing assistance to patient 11 according to ventilation settings (e.g., a ventilation mode and/or parameter settings) selected manually by a user and/or automatically by control system 31. One or more of such ventilation settings may be determined by the determination at step 312.

At step 316, control system 22 may control operational aspects of ventilation system 12 based at least on proximal pressure measurements from proximal pressure sensor 80b. For example, gas delivery control system 31 may control the pressure and/or flow rate of gas delivered toward patient 11 based on proximal pressure measurements from sensor 80b. As another example, if an exhalation valve 96 is connected to system 12, control system 22 may control exhalation valve 96 (e.g., by controlling pilot valve 102) based on proximal pressure measurements from sensor 80b.

Alternatively, if proximal pressure detection system 36 determines at step 308 that a proximal pressure line 100 is not connected to ventilation system 12, the method may advance to step 318. At step 318, system 36 may generate and/or display to the user a notification or alarm that a proximal pressure line 100 is not connected and/or that proximal pressure sensor 80b measurement(s) will not be used (or that for outlet pressure sensor 80a measurement(s) will be used) for controlling aspects of ventilation system 12.

At step 320, proximal pressure detection system 36 may allow the user to respond to the alarm displayed at step 318 before beginning or continuing breathing assistance to patient 11. For example, system 36 may display a user-selectable option to connect a proximal pressure line 100 or to continue without a proximal pressure line 100. If the user connects a proximal pressure line 100, the method may advance to step 312. If the user selects to continue without a proximal pressure line 100, the method may advance to step 322. In some embodiments, step 320 may be excluded, wherein the method may automatically advance from step 318 to step 322.

At step 322, control system 31 may allow or disallow particular ventilation modes or settings based on the determination that a proximal pressure line 100 is not connected to ventilation system 12 (and that proximal pressure sensor 80*b* measurement(s) may not be used for controlling ventilation system 12). For example, control system 31 may disallow user or automatic selection of, and/or automatic switching to, certain ventilation modes or settings that require accurate patient pressure readings that may be provided by proximal pressure sensor 80*b* but not by outlet pressure sensor 80*a*.

At step 324, ventilation system 12 may provide breathing assistance to patient 11 according to ventilation settings (e.g., a ventilation mode and/or parameter settings) selected manually by a user and/or automatically by control system 31. One or more of such ventilation settings may be determined by the determination at step 322.

At step 326, control system 22 may control operational aspects of ventilation system 12 based at least on outlet pressure measurements from outlet pressure sensor 80*a*. For example, gas delivery control system 31 may control the pressure and/or flow rate of gas delivered toward patient 11 based on outlet pressure measurements from sensor 80*a*. As another example, if an exhalation valve 96 is connected to system 12, control system 22 may control exhalation valve 96 (e.g., by controlling pilot valve 102) based on outlet pressure measurements from sensor 80*a*. In some embodiments, outlet pressure measurements from sensor 80*a* may be "corrected" (e.g., to compensate for pressure drop within connection system 14) using any suitable technique, e.g., any of the techniques disclosed in pending EP Patent Application EP 08006240.9, filed on Mar. 31, 2008, and entitled "Systems and Methods for Compensating for Pressure Drop in a Breathing Assistance System."

While providing breathing assistance to patient 11, proximal pressure detection system 36 may continue to determine whether a proximal pressure line 100 is connected to system 12 periodically, continuously, in response to a detected event or user request, or at any other time. In this manner, control system 22 may adjust to a connection or disconnection of a proximal pressure line 100 while system 12 is providing breathing assistance to patient 11. Such detection may include, for example, the techniques discussed above at steps 304-308.

As shown at step 328, if ventilation system 12 is providing breathing assistance using proximal pressure sensor 80*b* measurements for controlling various operational aspects, and system 36 detects disconnection of proximal pressure line 100, the method may advance to steps 318-326 to switch from proximal pressure sensor 80*b* measurement to outlet pressure sensor 80*a* measurements. Thus, for example, system 36 may generate a user alarm indicating disconnection of proximal pressure line 100 (at step 318), allow the user to re-connect proximal pressure line 100 or continue without proximal pressure line 100 (at step 320), allow or disallow particular ventilation modes or settings based on the determination that proximal pressure line 100 is not connected (at step 322), provide breathing assistance according to the now relevant ventilation settings (at step 324), and control operational aspects of ventilation system 12 based on outlet pressure sensor 80*a* measurements (at step 326).

Similarly, as shown at step 330, if ventilation system 12 is providing breathing assistance using outlet pressure sensor 80*a* measurements for controlling various operational aspects, and system 36 detects connection (or reconnection) of a proximal pressure line 100, the method may advance to steps 310-316 to switch from outlet pressure sensor 80*a* measurements to proximal pressure sensor 80*b* measurements. Thus, for example, system 36 may generate a user notification indicating connection of proximal pressure line 100 (at step 310), allow or disallow particular ventilation modes or settings based on the determination that proximal pressure line 100 is connected (at step 312), provide breathing assistance according to the now relevant ventilation settings (at step 314), and control operational aspects of ventilation system 12 based on proximal pressure sensor 80*a* measurements (at step 316).

Figure 9:
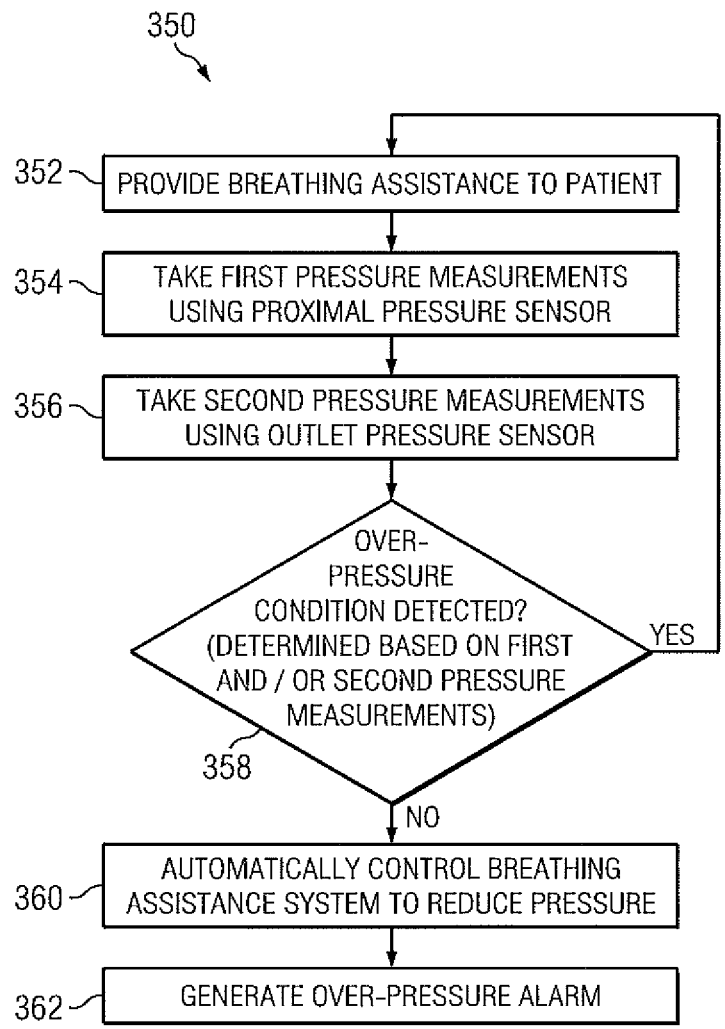
FIG. 9 illustrates an example method for detecting and managing an over-pressure condition in a breathing assistance system, according to certain embodiments of the present disclosure.

FIG. 9 illustrates an example method 350 for detecting and managing an over-pressure condition in a breathing assistance system 10, according to certain embodiments of the present disclosure. For example, method 350 may be used for detecting an over-pressure condition in connection system 14 (e.g., in breathing circuit 16) based on pressure signals received from one or more pressure sensors 24 and managing a detected over-pressure condition.

The example method 350 uses two pressure sensors, either separately or in combination, for detecting an over-pressure condition in breathing assistance system 10. In particular, in the discussion below, the two pressure sensors are outlet pressure sensor 80*a* and proximal pressure sensor 80*b*. However, method 350 may similarly apply to other pairs of pressure sensors provided in breathing assistance system 10, depending on the specific embodiment. Such pair of pressure sensors may be positioned at any location in breathing assistance system 10, and may be configured to measure pressure at any different locations within breathing assistance system 10, e.g., any locations along a conduit of ventilation system 12 and/or connection system 14. In addition, although example method 350 uses two pressure sensors for detecting an over-pressure condition in breathing assistance system 10, similar techniques may be used for detecting an over-pressure condition using more than two (e.g., 3 or more) pressure sensors, either separately or in combination.

At step 352, ventilation system 12 may provide breathing assistance to patient 11, e.g., according to ventilation settings (e.g., a ventilation mode and/or parameter settings) selected manually by a user and/or automatically by control system 31.

At step 354, proximal pressure sensor 80*b* may take and communicate one or more pressure measurements to proximal pressure detection system 36. Proximal pressure sensor 80*b* may communicate a single pressure measurement or multiple pressure measurements over any suitable time period. In some embodiments or configurations, proximal pressure sensor 80*b* may be configured to measure a proximal pressure near patient 11 via a proximal pressure line 100 connected at one end to ventilation system 12 and extending along a limb of breathing circuit 16.

At step 356, outlet pressure sensor 80*a* may take and communicate one or more pressure measurements to proximal pressure detection system 36. Outlet pressure sensor 80*a* may communicate a single pressure measurement or multiple pressure measurements over any suitable time period. In some embodiments or configurations, outlet pressure sensor 80*a* may be located at or near a main gas outlet of ventilation system 12 (e.g., at or near an outlet of gas delivery system 20) to measure the pressure of gas flow exiting ventilation system 12 or gas delivery system 20, or the pressure of gas flow entering connection system 14. The two sensors 80*a* and 80*b* may detect different pressure levels, e.g., due to pressure drop inherent in breathing circuit 16.

Steps 354 and 356 may be performed in any order and/or substantially simultaneously.

At step 358, over-pressure security system 32 may determine whether an over-pressure condition is present in system 10 (e.g., in connection system 14). For example, overpressure security system 32 may compare pressure measurements received from sensors 80*a* and 80*b* to one or more threshold pressure values to automatically detect an over-pressure condition. Pressure measurements from both sensors 80*a* and 80*b* may each be compared to a single pressure threshold value, or each sensor's measurements may be compared to a separate corresponding pressure threshold value. Such pressure threshold value(s) may be determined in any suitable manner, and may be manually or automatically adjusted over time.

In some embodiments, over-pressure security system 32 may compare pressure measurements received from sensors 80*a* and 80*b* to different pressure threshold values to account for differences between expected pressure measurements from sensors 80*a* and 80*b*, e.g., due to pressure drop in connection system 14. The pressure threshold values for comparing pressures from each of sensors 80*a* and 80*b* may be determined in any suitable manner (e.g., stored values based on empirical data).

In some embodiments, one or both of threshold pressure values may be selected (e.g., using an algorithm or look-up table) based on the particular flow rate at which such measurements by sensors 80*a* and/or 80*b* were taken. Thus, one or both of threshold pressure values may be selected from a range of values to account for the fact that, in certain configurations, the expected difference in pressure measurements from sensor 80*a* and sensor 80*b* (e.g., due to pressure drop within connection system 14) depends on the flow rate through connection system 14.

In some embodiments, over-pressure security system 32 may determine that an over-pressure condition is present if either (a) the pressure measured by proximal pressure sensor 80*a* exceeds its corresponding threshold value or (b) the pressure measured by proximal pressure sensor 80*a* exceeds its corresponding threshold value (which may be the same as, or different from, the corresponding threshold value for proximal pressure sensor 80*a* measurements, as discussed above). In such embodiments, using both sensors 80*a* and 80*b* may provide a level of redundancy for protecting against over-pressure situations.

In other embodiments, over-pressure security system 32 may determine that an over-pressure condition is present only if both (a) the pressure measured by proximal pressure sensor 80*a* exceeds its corresponding threshold value and (b) the pressure measured by proximal pressure sensor 80*a* exceeds its corresponding threshold value (which may be the same as, or different from, the corresponding threshold value for proximal pressure sensor 80*a* measurements, as discussed above).

If over-pressure security system 32 does not determine an over-pressure condition at step 358, the method may return to steps 352-358 to continue providing breathing assistance, take pressure measurements, and determine whether an over-pressure condition arises. Steps 354-358 may be repeated at any time interval, e.g., substantially continuously, periodically, or in response to some triggering event.

Alternatively, if over-pressure security system 32 determines an over-pressure condition at step 358, system 32 may manage the over-pressure condition at step 360. For example, over-pressure security system 32 may notify gas delivery control system 31 such that system 31 controls gas delivery system 20 to end the over-pressure condition, e.g., by (a) reducing the pressure or flow rate produced by gas delivery system 20 (e.g., to a pressure at or just below a threshold pressure value, or to a lower pressure) or (b) shutting down gas delivery system 20. For example, in embodiments in which gas delivery system 20 includes a blower (e.g., a turbine-based blower), gas delivery control system 31 may reduce the speed of the blower.

At step 362, over-pressure security system 32 may generate an over-pressure alarm. The alarm may comprise any notification that may be sensed by a user, e.g., an audible alarm or a visible alarm displayed to the user, e.g., via display 28 or separate device (e.g., an LED).

In some configurations, monitoring signals from both sensors 80*a* and 80*b* as discussed above may provide redundancy to account for situations in which 80*a* or 80*b* is not providing useful data, e.g., where one of sensors 80*a* and 80*b* is damaged or not working properly, or where a proximal pressure line 100 is not used or is blocked.

Figure 10:
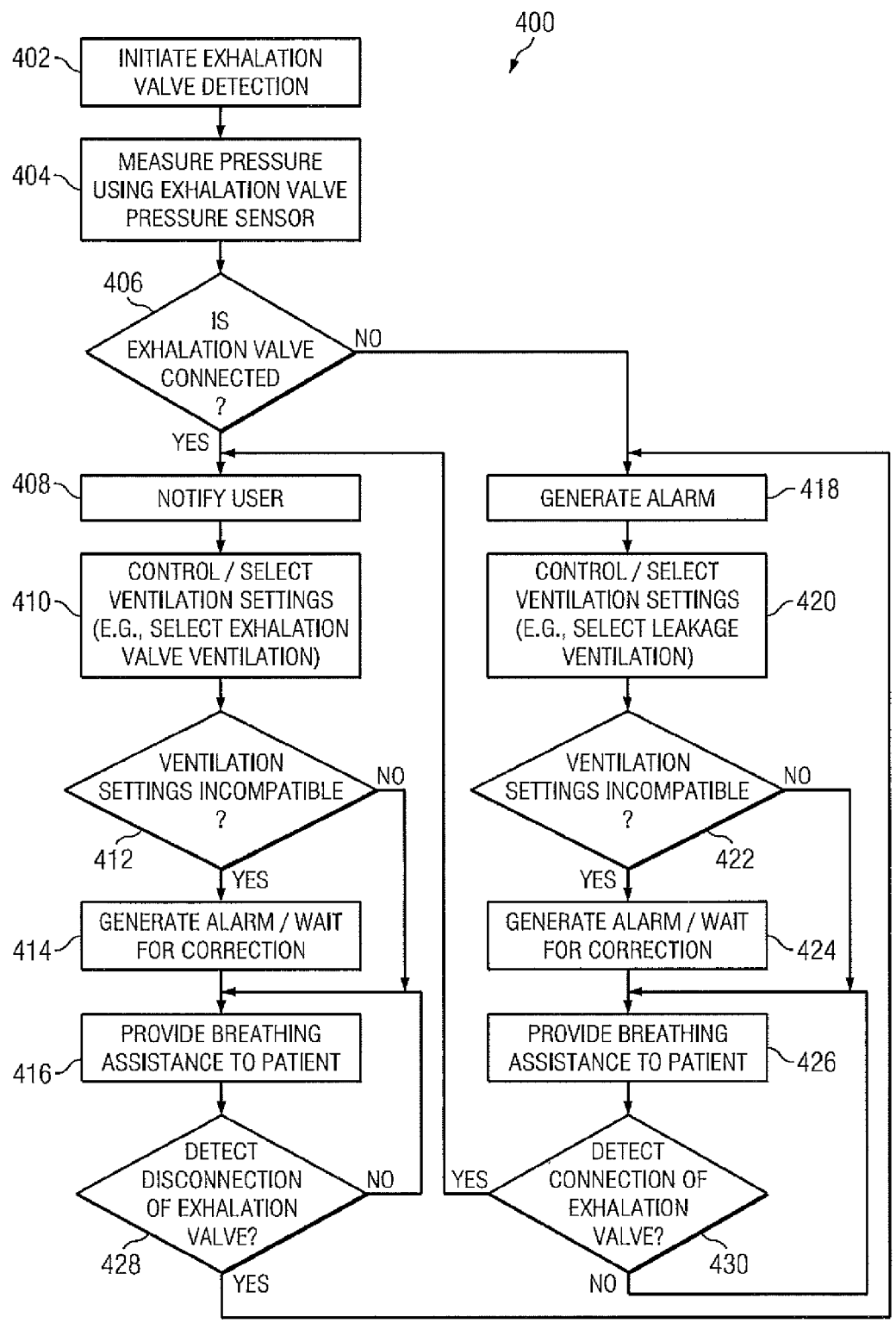
FIG. 10 illustrates an example method for determining whether an exhalation valve is connected to a ventilation system, and controlling the ventilation system accordingly, according to certain embodiments of the present disclosure.

FIG. 10 illustrates an example method 400 for determining whether an exhalation valve 96 is connected to ventilation system 12, and controlling ventilation system 12 accordingly, according to certain embodiments of the present disclosure.

At step 402, an exhalation valve detection process is initiated. Such process may be initiated automatically upon a triggering event (e.g., turning on ventilation system 12, user or automatic selection of a particular ventilation mode or setting, or execution of a start-up test) or based on a user-initiated request. In general, as discussed below, the exhalation valve detection process determines whether an exhalation valve 96 is connected to ventilation system 12 (e.g., via an exhalation valve control line 98) such that ventilation system 12 may control exhalation valve 96 while providing breathing assistance to patient 11.

At step 404, exhalation valve sensor 80*c* may take and communicate one or more pressure measurements to exhalation valve detection system 34. Exhalation valve sensor 80*c* may communicate a single pressure measurement or multiple pressure measurements over any suitable time period.

At step 406, exhalation valve detection system 34 may determine whether an exhalation valve 96 is connected to ventilation system 12 (e.g., via an exhalation valve control line 98) based at least on pressure measurements from exhalation valve sensor 80*c*. For example, exhalation valve detection system 34 may compare measurement(s) from exhalation valve sensor 80*c* to a threshold pressure value to automatically determine whether an exhalation valve 96 is connected. Generally, if no exhalation valve 96 is connected, the connection port for exhalation valve control line 98 may remain open, and thus the pressure measured by exhalation valve sensor 80*c* may remain low (e.g., below the threshold pressure value). However, if an exhalation valve 96 is connected via an exhalation valve control line 98 connected to ventilation system 12, the pressure measured by exhalation valve sensor 80*c* may increase (e.g., above the threshold pressure value). The threshold pressure value may be determined in any suitable manner (e.g., stored value(s) based on empirical data), and may be manually or automatically adjusted over time.

If exhalation valve detection system 34 determines that an exhalation valve 96 is connected to ventilation system 12, the method may proceed to step 408. Otherwise, the method may proceed to step 418.

At step 408, exhalation valve detection system 34 may generate and display a user notification that an exhalation valve 96 is connected and/or being used for controlling breathing assistance.

At step 410, gas delivery control system 31 may automatically select between different ventilation modes or settings or otherwise control one or more ventilation parameters (e.g., flow and/or pressure) based on the determination that an exhalation valve 96 is connected to ventilation system 12. For example, in some embodiments in which ventilation system 12 can provide either leakage ventilation or exhalation valve ventilation, gas delivery control system 31 may automatically select or switch to exhalation valve ventilation based on the determination that an exhalation valve 96 is connected to ventilation system 12.

In addition, gas delivery control system 31 may allow or disallow particular ventilation modes or settings based on the determination that an exhalation valve 96 is connected to ventilation system 12. For example, control system 31 may allow user or automatic selection of, and/or automatic switching to, certain ventilation modes or settings that require control of an exhalation valve 96.

At step 412, in example configurations in which ventilation system 12 selects or switches to exhalation valve ventilation (at step 410), gas delivery control system 31 may determine whether any selected ventilation settings are incompatible with exhalation valve ventilation. If so, gas delivery control system 31 may trigger an alarm at step 414 and wait for the user to adjust the selected settings to become compatible before beginning ventilation of patient 11. The alarm may comprise any notification that may be sensed by a user, e.g., an audible alarm or a visible alarm displayed to the user, e.g., via display 28 or separate device (e.g., an LED). If not, the method may continue to step 416.

At step 416, ventilation system 12 may provide breathing assistance to patient 11 according to a ventilation mode and/or settings (e.g., exhalation valve ventilation) determined at steps 410-414.

Returning to the decision at step 406, if exhalation valve detection system 34 determines that an exhalation valve 96 is not connected to ventilation system 12, the method may proceed to step 418.

At step 418, exhalation valve detection system 34 may generate and display a user notification or alarm that an exhalation valve 96 is not connected and may not be used for controlling breathing assistance. System 34 may provide the user an opportunity to connect an exhalation valve 96, or to select to continue without an exhalation valve 96, or alternatively the method may automatically continue to step 420.

At step 420, gas delivery control system 31 may automatically select between different ventilation modes or settings or otherwise control one or more ventilation parameters (e.g., flow and/or pressure) based on the determination that an exhalation valve 96 is not connected to ventilation system 12. For example, in some embodiments in which ventilation system 12 can provide either leakage ventilation or exhalation valve ventilation, gas delivery control system 31 may automatically select or switch to leakage ventilation based on the determination that an exhalation valve 96 is not connected to ventilation system 12.

In addition, gas delivery control system 31 may allow or disallow particular ventilation modes or settings based on the determination that an exhalation valve 96 is not connected to ventilation system 12. For example, control system 31 may disallow user or automatic selection of, and/or automatic switching to, certain ventilation modes or settings that require control of an exhalation valve 96.

At step 422, in example configurations in which ventilation system 12 selects or switches to leakage ventilation (at step 410), gas delivery control system 31 may determine whether any selected ventilation settings are incompatible with leakage ventilation. If so, gas delivery control system 31 may trigger an alarm at step 424 and wait for the user to adjust the selected settings to become compatible before beginning ventilation of patient 11. The alarm may comprise any notification that may be sensed by a user, e.g., an audible alarm or a visible alarm displayed to the user, e.g., via display 28 or separate device (e.g., an LED). If not, the method may continue to step 426.

At step 426, ventilation system 12 may provide breathing assistance to patient 11 according to a ventilation mode and/or settings (e.g., leakage ventilation) determined at steps 420-424.

While providing breathing assistance to patient 11, exhalation valve detection system 34 may continue to determine whether an exhalation valve 96 is connected to system 12 periodically, continuously, in response to a detected event or user request, or at any other time. In this manner, control system 22 may adjust to a connection or disconnection of an exhalation valve 96 while system 12 is providing breathing assistance to patient 11. Such detection may include, for example, the techniques discussed above at steps 402-406.

As shown at step 428, if exhalation valve detection system 34 detects a disconnection of exhalation valve 96 while ventilation system 12 is providing breathing assistance, the method may advance to steps 418-416 to account for the disconnection. This may include, e.g., generating a user alarm and automatically adjusting one or more ventilation settings (e.g., switching from exhalation valve ventilation to leakage ventilation).

Similarly, as shown at step 430, if exhalation valve detection system 34 detects a connection/re-connection of exhalation valve 96 while ventilation system 12 is providing breathing assistance, the method may advance to steps 408-416 to account for the connection/re-connection. This may include, e.g., generating a user notification and automatically adjusting one or more ventilation settings (e.g., switching from leakage ventilation to exhalation valve ventilation).

Figure 11:
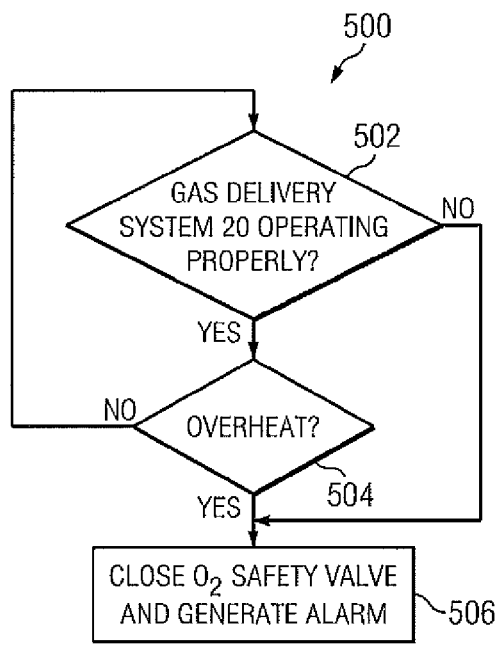
FIG. 11 illustrates an example method for managing a supplemental gas supply (e.g., supplemental oxygen supply) in a breathing assistance system, according to certain embodiments of the present disclosure.

FIG. 11 illustrates an example method 500 for managing a supplemental gas supply (e.g., supplemental oxygen supply) in a breathing assistance system 10 configured to provide breathing assistance to a patient 11, according to certain embodiments of the present disclosure. In particular, method 500 may provide security for a supplemental gas supply when a gas delivery system 20 of breathing assistance system 10 is overheating or not operating properly (e.g., not running). For example, $O_2$ safety system 38 may stop or slow the flow of the supplemental gas (e.g., by closing a safety valve) in such situations. Although the discussion focuses on a supplemental oxygen supply, the same techniques may be used for any other type of supplemental gas supply.

At step 502, $O_2$ safety system 38 may determine whether gas delivery system 20 is operating properly (e.g., not running or running improperly). For example, $O_2$ safety system 38 may communicate with gas delivery control system 31 to obtain data regarding the operation of gas delivery system 20. If $O_2$ safety system 38 determines that gas delivery system 20 is not operating properly, the method may proceed to step 506. Otherwise, if $O_2$ safety system 38 determines that gas delivery system 20 is operating properly, the method may proceed to step 504.

At step 504, $O_2$ safety system 38 (e.g., an overheat detection module 158 of system 38) may determine whether gas delivery system 20 is overheating by monitoring readings from a temperature sensor 83 configured to measure the temperature of gas delivery system 20 or a component thereof. For example, overheat detection module 158 may compare readings from temperature sensor 83 with threshold temperature(s) to determine whether gas delivery system 20 is overheating. If $O_2$ safety system 38 determines that gas delivery system 20 is overheating, the method may proceed to step 506. Otherwise, if O₂ safety system 38 determines that gas delivery system 20 is not overheating, the method may return to step 502.

Steps 502 and 504 may be performed in any order and/or substantially simultaneously. Steps 502 and 504 may be performed at any time, e.g., substantially continuously, periodically, or in response to a triggering event.

At step 506, in response to determining that gas delivery system 20 is not operating properly (at step 502) or that gas delivery system 20 is overheating (at step 504), overheat detection module 158 may send an overheat notification signal to gas delivery control system 31. Based on such signal, gas delivery control system 31 may control O2 safety valve and/or gas delivery system 20 accordingly. For example, gas delivery control system 31 may partially or fully close O2 safety valve to slow or stop the flow of supplemental oxygen.

Figure 12:
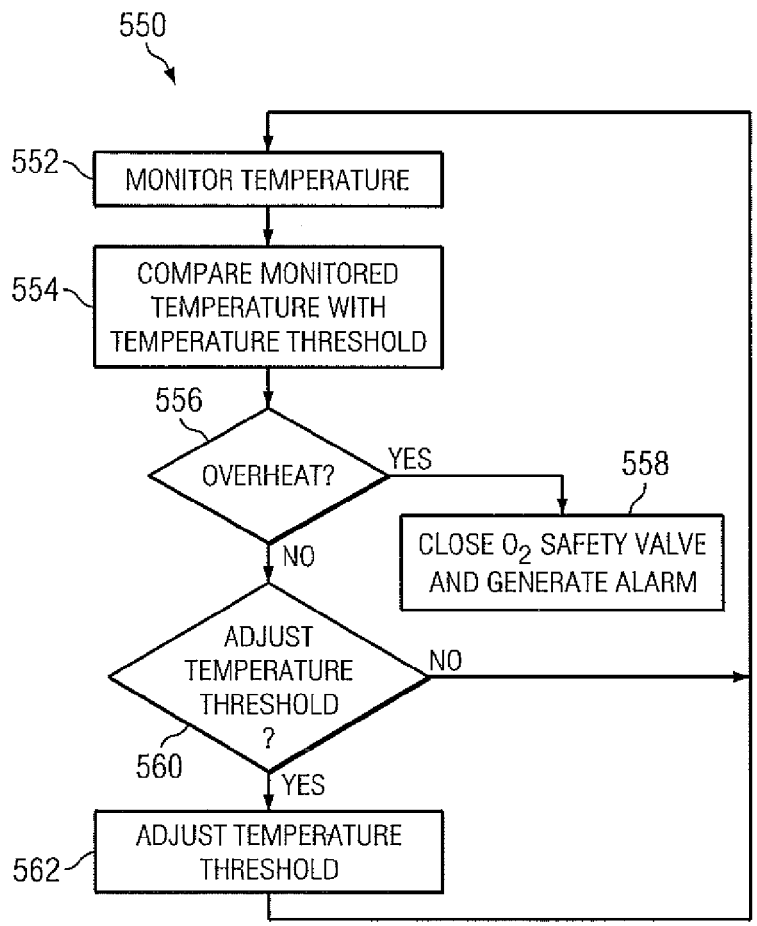
FIG. 12 illustrates an example method for determining an overheat condition in a breathing assistance system and managing a supplemental gas flow (e.g., supplemental oxygen flow) using an $O_2$ safety system as shown in FIG. 4A, according to certain embodiments of the present disclosure.

FIG. 12 illustrates an example method 550 for determining an overheat condition in a breathing assistance system 10 and managing a supplemental gas flow (e.g., supplemental oxygen flow) accordingly, according to certain embodiments of the present disclosure. In general, method 550 is an example embodiment of steps 504 and 506 of method 500 shown in FIG. 11. More particularly, method 550 may monitor for an overheat condition in a gas delivery system 20, and in response to detecting an overheat condition, stop or slow the flow of the supplemental gas (e.g., by closing a safety valve). Again, although the discussion focuses on a supplemental oxygen supply, the same techniques may be used for any other type of supplemental gas supply.

At step 552, overheat detection module 158 may monitor temperature readings from temperature sensor 83 configured to measure the temperature of gas delivery system 20 or a component thereof. Temperature sensor 83 may take and communicate measurement signals to overheat detection module 158 at any time, e.g., substantially continuously, periodically, or in response to a triggering event.

At step 552, overheat detection module 158 may compare temperature readings from temperature sensor 83 with a threshold temperature to determine whether gas delivery system 20 is overheating. Such threshold temperature may be constant or may change over time. For example, a threshold temperature may be determined using an algorithm or look-up table relating the threshold value to one or more other parameters, e.g., the current pressure or flow rate of gas delivered by delivery system 20, or the current speed of a turbine (in embodiments in which gas delivery system 20 comprises a turbine-based blower). Thus, for example, an algorithm may be used to increase the threshold temperature in proportion to the flow rate or turbine speed, as higher temperatures are expected with higher flow rates or turbine speeds.

As another example, the threshold temperature may be selected based on the current ventilation mode or settings. For example, different threshold temperatures may be used for SIMV ventilation, Assist/Control ventilation, and CPAP ventilation. As another example, different threshold temperatures may be used for adult vs. pediatric ventilation, as higher temperatures are expected with adult ventilation (e.g., due to higher flow rates or turbine speeds).

At step 556, overheat detection module 158 may determine whether gas delivery system 20 is overheating based on any number of temperature readings and comparisons performed at steps 552 and 554. For example, overheat detection module 158 may determine an overheat condition in response to a single sensor reading above the relevant threshold temperature. As another example, overheat detection module 158 may determine an overheat condition based on a predetermined number (e.g., 5) of consecutive sensor readings above the relevant threshold temperature, based on sensor readings remaining above the relevant threshold temperature for a predetermined duration (e.g., 10 seconds). As another example, overheat detection module 158 may determine an overheat condition based on an average of sensor readings for a predetermined number of readings or over a predetermined duration.

If overheat detection module 158 detects an overheat condition at step 556, the method may proceed to step 558. At step 558, control system 22 may control (e.g., reduce or stop) the supplemental gas flow and generate an alarm, in response to detecting an overheat condition at step 556. For example, overheat detection module 158 may send an overheat notification signal to gas delivery control system 31, which may in turn control O2 safety valve 156 and/or gas delivery system 20 accordingly. For example, gas delivery control system 31 may partially or fully close O2 safety valve 156 to slow or stop the flow of supplemental oxygen.

Overheat detection module 158 and/or gas delivery control system 31 may generate any suitable alarm(s) 159 regarding the overheat condition and/or the closing of O2 safety valve 156. An alarm 159 may comprise any notification that may be sensed by a user, e.g., audible alarm or a visible alarm displayed to the user.

If overheat detection module 158 does not detect an overheat condition at step 556, the method may proceed to step 560. At step 560, overheat detection module 158 may determine to adjust the temperature threshold used at step 554. For example, the threshold temperature may be adjusted (e.g., using an algorithm or look-up table) at step 562 according to one or more current ventilation parameters (e.g., the current pressure or flow rate of gas delivered by delivery system 20, or the current speed of a turbine). Thus, for example, overheat detection module 158 automatically increase the temperature threshold (according to an algorithm or look-up table) in response to an increase in the current flow rate or turbine speed, as higher temperatures are expected with higher flow rates or turbine speeds.

As another example, overheat detection module 158 may automatically adjust the temperature threshold based on a change in the current ventilation mode or settings. For example, module 158 may adjust the temperature threshold in response to a switch from Assist/Control ventilation to CPAP ventilation.

Figure 13A:
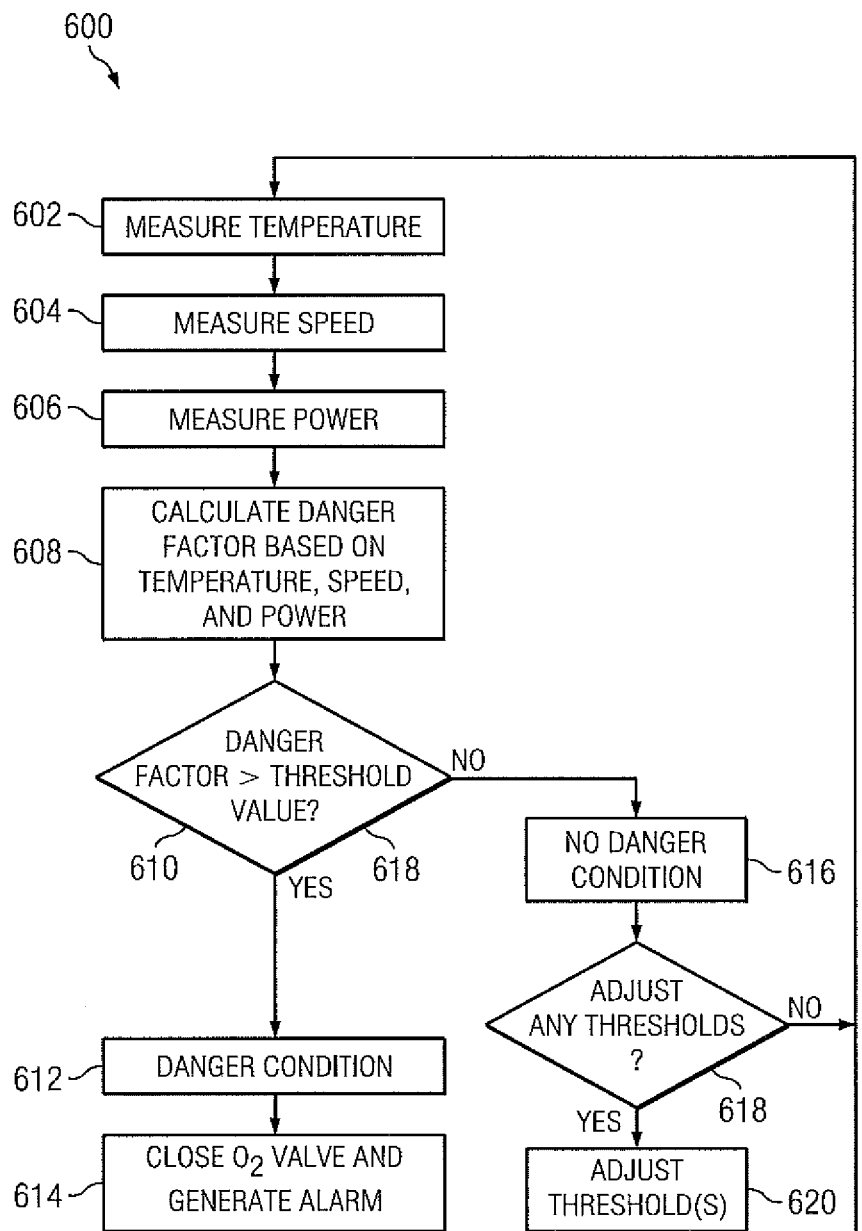
FIGS. 13A and 13B illustrate example methods for determining an overheat condition in a breathing assistance system and managing a supplemental gas flow (e.g., supplemental oxygen flow) using an $O_2$ safety system as shown in FIG. 4B, according to certain embodiments of the present disclosure.
Figure 13B:
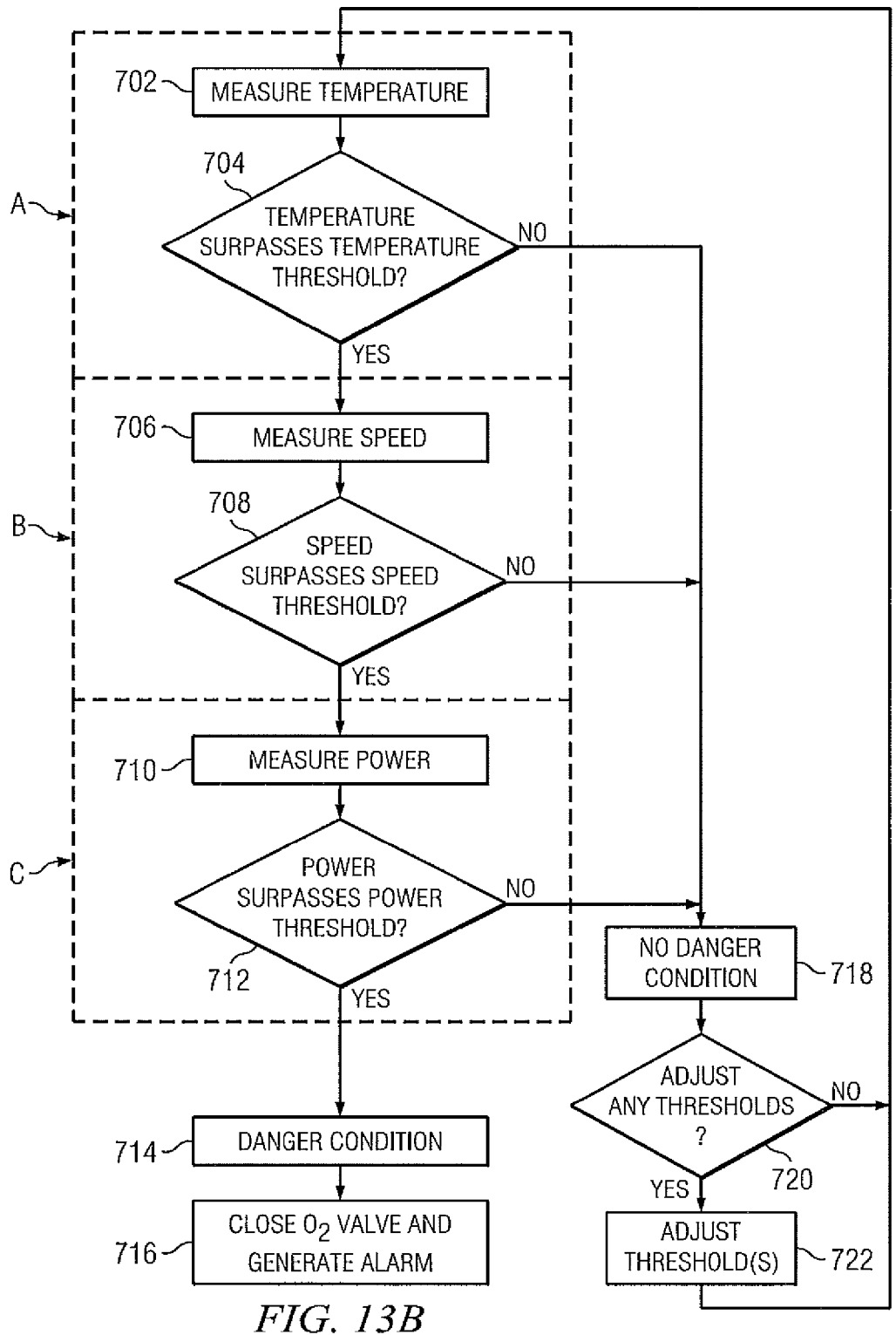

FIGS. 13A and 13B illustrate example methods 600 and 700 for determining a danger condition in a breathing assistance system and managing a supplemental gas flow (e.g., supplemental oxygen flow) using an O₂ safety system as shown in FIG. 4B, according to certain embodiments of the present disclosure.

Referring to FIG. 13A, method 600 may be performed at any time during the operation of ventilation system 12. At step 602, a temperature of gas delivery system 20 (e.g., a blower motor) may be measured, e.g., using temperature sensor 83. At step 604, an operational speed of a component (e.g., a motor, blower, turbine) of gas delivery system 20 may be measured, e.g., using a speed sensor 84. At step 606, the power drawn by a component (e.g., a motor, blower, turbine) of gas delivery system 20 may be measured, e.g., using a power monitor 85. Steps 602-606 may be performed in any order, and each step may be performed at any suitable time and frequency. In addition, in some embodiments, at least one of steps 602-606 may be excluded, e.g., in embodiments in which O₂ safety system is controlled using temperature and speed measurements, but not power measurements.

At step 608, a danger factor may be calculated based on the data obtained at steps 602-606. For example, safety status module 161 may calculate a safety factor using one or more algorithms relating the different types of measurements obtained at steps 602-606.

At step 610, safety status module 161 may compare the calculated safety factor to a danger condition threshold value to determine whether a danger condition is present. If it is determined that a danger condition is present (see step 612), control system 22 may slow or stop the supplemental oxygen flow (e.g., by controlling O2 safety valve 156) and generate an alarm at step 614.

Alternatively, if it is determined that a danger condition is not present (see step 616), the method may advance to step 618. At step 618, safety status module 161 may determine to adjust the danger factor threshold value used at step 610. For example, the threshold value may be adjusted (e.g., using an algorithm or look-up table) at step 620 according to the current ventilation mode or current ventilation parameters. The method may then return to steps 602-606 for continued measurements.

Referring to FIG. 13B, method 700 may be performed at any time during the operation of ventilation system 12. At step 702, a temperature of gas delivery system 20 (e.g., a blower motor) may be measured, e.g., using temperature sensor 83. At step 704, safety status module 161 may compare the measured temperature to a temperature threshold value. If the measured temperature does not surpass the temperature threshold value, there is no danger condition present, and the method may continue to step 718.

However, if the measured temperature does surpass the temperature threshold value, the method continues to step 706 for further analysis to determine whether a danger condition is present. At step 706, an operational speed of a component (e.g., a motor, blower, turbine) of gas delivery system 20 may be measured, e.g., using a speed sensor 84. At step 708, safety status module 161 may compare the measured speed to a speed threshold value. If the measured speed does not surpass the speed threshold value, there is no danger condition present, and the method may continue to step 718.

However, if the measured speed does surpass the speed threshold value, the method continues to step 710 for further analysis to determine whether a danger condition is present. At step 710, the power drawn by a component (e.g., a motor, blower, turbine) of gas delivery system 20 may be measured, e.g., using a power monitor 85. If the measured power does not surpass the power threshold value, there is no danger condition present, and the method may continue to step 718.

However, if the measured power does surpass the power threshold value (in combination with the temperature and speed surpassing their corresponding threshold values, as described above), a danger condition is identified at 714. In response to identifying the danger condition, control system 22 may slow or stop the supplemental oxygen flow (e.g., by controlling O2 safety valve 156) and generate an alarm at step 716.

As discussed above, if any of the measured temperature, speed, or power do not surpass their corresponding thresholds, there is no danger condition present, as indicated at step 718. At step 720, safety status module 161 may determine to adjust one or more threshold values used at steps 704, 708, and/or 712. For example, the speed threshold value may be adjusted (e.g., using an algorithm or look-up table) at step 722 according to the current ventilation mode or current ventilation parameters. The method may then return to step 702.

Certain steps may be eliminated from method 700 depending on which of temperature, speed, and power measurements are used for controlling O₂ safety system, according to the particular embodiment. Thus, any of the method modules "A", "B", or "C" shown in FIG. 13B may be removed from method 700, depending on the particular embodiment. For example, in embodiments in which temperature and speed measurements, but not power measurements, are used for controlling O₂ safety system, steps 710 and 712 indicated as method module "C" may be removed from method 700. As another example, in embodiments in which speed and power measurements, but not temperature measurements, are used for controlling O₂ safety system, steps 702 and 704 indicated as method module "A" may be removed from method 700.

It should be understood that various changes, substitutions and alterations can be made herein without departing from the spirit and scope of the disclosure as illustrated by the following claims.

What is claimed is:

1. A method for controlling a breathing assistance system configured to provide breathing assistance to a patient, comprising:
    providing the breathing assistance system;
    automatically determining whether a proximal pressure line having an associated proximal pressure sensor is connected to the breathing assistance system; and
    automatically determining whether or not to use signals from the proximal pressure sensor for controlling a subsequent operation of the breathing assistance system based on the determination of whether the proximal pressure line is connected to the breathing assistance system.

2. A method according to claim 1, wherein controlling the subsequent operation of the breathing assistance system comprises adjusting at least one of a pressure and flow rate of gas delivered toward the patient.

3. A method according to claim 1, comprising:
    based at least on the determination of whether the proximal pressure line is connected to the breathing assistance system, selecting either the proximal pressure sensor or another pressure sensor at a different location for use in controlling the breathing assistance provided to the patient; and
    controlling the breathing assistance provided to the patient based at least on signals from the selected pressure sensor.

4. A method according to claim 3, wherein the proximal pressure sensor is located downstream toward the patient relative to the another pressure sensor.

5. A method according to claim 4, wherein:
    the breathing assistance system includes a ventilation system, and a patient connection system between the ventilation system and the patient;
    the proximal pressure sensor is configured to measure gas pressure near a first end of the patient connection system proximate the patient; and
    the another pressure sensor is configured to measure gas pressure near a second end of the patient connection system generally opposite the first end.

6. A method according to claim 1, comprising:
    if the proximal pressure line is determined to be connected to the breathing assistance system, controlling the subsequent operation of the breathing assistance system, based at least on signals from a first set of one or more sensors including the proximal pressure sensor; and if the proximal pressure line is determined to be disconnected from the breathing assistance system, controlling the subsequent operation of the breathing assistance system, based at least on signals from a second set of one or more sensors excluding the proximal pressure sensor.

7. A method according to claim 6, wherein:
the first set of one or more sensors includes the proximal pressure sensor and at least one other pressure sensor; and
the second set of one or more sensors includes the at least one other pressure sensor and excludes the proximal pressure sensor.

8. A method according to claim 1, comprising:
in addition to determining whether the proximal pressure line is connected to the breathing assistance system, determining whether the associated proximal pressure sensor is operating properly; and
automatically determining whether or not to use the signals from the proximal pressure sensor for controlling the subsequent operation of the breathing assistance system based on (a) the determination of whether the proximal pressure line is connected to the breathing assistance system and (b) the determination of whether the proximal pressure sensor is operating properly.

9. A method according to claim 1, comprising:
in response to determining that the proximal pressure line is not connected to the breathing assistance system, automatically determining to disallow at least one particular breathing assistance mode or setting;
selecting a breathing assistance mode or setting based at least on the determination to disallow the at least one particular breathing assistance mode or setting; and
providing the breathing assistance to the patient according to the selected breathing assistance mode or setting.

10. A method according to claim 1, comprising automatically determining whether the proximal pressure line having the associated proximal pressure sensor is connected to the breathing assistance system based on the signals received from the proximal pressure sensor.

11. A method according to claim 1, wherein automatically determining whether the proximal pressure line having the associated proximal pressure sensor is connected to the breathing assistance system comprises:
comparing one or more pressure sensor measurements by the proximal pressure sensor with a predefined threshold pressure; and
determining that the proximal pressure line is connected to the breathing assistance system if one or more pressure sensor measurements by the proximal pressure sensor are greater than the predefined threshold pressure.

12. A method according to claim 1, wherein automatically determining whether the proximal pressure line having the associated proximal pressure sensor is connected to the breathing assistance system comprises:
comparing one or more pressure sensor measurements by the proximal pressure sensor with an expected pressure value; and
determining that the proximal pressure line is connected to the breathing assistance system if one or more pressure sensor measurements by the proximal pressure sensor differ from the expected pressure value by less than a predefined threshold value.

13. A method according to claim 1, wherein automatically determining whether the proximal pressure line having the associated proximal pressure sensor is connected to the breathing assistance system comprises:
receiving one or more first pressure sensor signals from the proximal pressure sensor;
receiving one or more second pressure sensor signals from another pressure sensor; and
comparing the one or more first pressure sensor signals with the one or more second pressure sensor signals.

14. A method according to claim 13, wherein:
the one or more first pressure sensor signals from the proximal pressure sensor indicate a first pressure level;
the one or more second pressure sensor signals from the another pressure sensor indicate a second pressure level; and
automatically determining whether the proximal pressure line having the associated proximal pressure sensor is connected to the breathing assistance system further comprises determining that the proximal pressure line is connected to the breathing assistance system if the indicated first pressure level is higher than the indicated second pressure level.

15. A method according to claim 13, wherein:
the one or more first pressure sensor signals from the proximal pressure sensor indicate a first pressure level;
the one or more second pressure sensor signals from the another pressure sensor indicate a second pressure level; and
automatically determining whether the proximal pressure line having the associated proximal pressure sensor is connected to the breathing assistance system further comprises determining that the proximal pressure line is connected to the breathing assistance system if the indicated first pressure level is higher than the indicated second pressure level but by an amount within a threshold pressure difference.

16. A method for controlling a breathing assistance system configured to provide breathing assistance to a patient, comprising:
providing the breathing assistance system;
automatically determining whether a proximal pressure line having an associated proximal pressure sensor is connected to the breathing assistance system;
automatically determining to allow or disallow at least one particular breathing assistance mode or setting based on whether the proximal pressure line is determined to be connected to the breathing assistance system; and
selecting a particular breathing assistance mode or setting based at least on the determination to allow or disallow the at least one particular breathing assistance mode or setting; and
providing the breathing assistance to the patient according to the selected breathing assistance mode or setting.

17. A method according to claim 16, comprising determination whether the proximal pressure line is connected to the breathing assistance system while providing the breathing assistance to the patient.

18. A method according to claim 16, comprising:
providing the breathing assistance to the patient according to a first breathing assistance mode or setting;
while providing the breathing assistance to the patient according to the first breathing assistance mode or setting, performing the determination of whether the proximal pressure line is connected to the breathing assistance system;

in response to determining that the proximal pressure line is not connected to the breathing assistance system, automatically:

disallowing the first breathing assistance mode or setting; and switching to the particular breathing assistance mode or setting.

19. A method according to claim 16, comprising:

automatically disallowing at least one breathing assistance mode or setting in response to determining that the proximal pressure line is not connected to the breathing assistance system; and preventing user selection of the at least one disallowed breathing assistance mode or setting.

20. A method for controlling a breathing assistance system configured to provide breathing assistance to a patient, comprising:

providing the breathing assistance system;

automatically identifying that a first pressure sensor of the breathing assistance system is not currently usable; and in response to determining that the first pressure sensor is not currently usable, automatically switching from a first, currently selected breathing assistance mode to a different, second breathing assistance mode predefined for use with signals from a second pressure sensor; and automatically implementing the second breathing assistance mode and controlling at least one parameter of the breathing assistance system based on the signals from the second pressure sensor.

21. The method of claim 20, wherein the second pressure sensor is selected from a following group: an outlet pressure sensor, a proximal pressure sensor, and a valve pressure sensor.

22. The method of claim 20, wherein the first pressure sensor is selected from a following group: an outlet pressure sensor, a proximal pressure sensor, and a valve pressure sensor.

23. The method of claim 20, wherein the first pressure sensor is not usable because the first pressure sensor is not working properly.

24. The method of claim 20, wherein the second pressure sensor is capable of measuring negative flow.

25. The method of claim 20, wherein the first pressure sensor is capable of measuring negative flow.

* * * * *